US012672936B2

(12) United States Patent
Pichler et al.

(10) Patent No.: US 12,672,936 B2
(45) **Date of Patent: \*Jul. 7, 2026**

(54) SUPPORT ARM FOR MEDICAL DEVICE SUPPORT SYSTEM

(71) Applicant: American Sterilizer Company, Mentor, OH (US)

(72) Inventors: Jerime Pichler, Willoughby, OH (US); Nicholas Grant Puterbaugh, Mentor on the Lake, OH (US)

(73) Assignee: American Sterilizer Company, Mentor, OH (US)

( * ) Notice: Subject to any disclaimer, the term of this patent is extended or adjusted under 35 U.S.C. 154(b) by 947 days.

This patent is subject to a terminal disclaimer.

(21) Appl. No.: 16/702,932

(22) Filed: Dec. 4, 2019

(65) Prior Publication Data

US 2020/0246109 A1      Aug. 6, 2020

Related U.S. Application Data

(60) Provisional application No. 62/799,100, filed on Jan. 31, 2019, provisional application No. 62/799,096, (Continued)

(51) Int. Cl.
A61B 90/50 (2016.01)
A61B 34/00 (2016.01)
(Continued)

(52) U.S. Cl.
CPC .............. A61B 90/50 (2016.02); A61B 90/35 (2016.02); F16M 13/022 (2013.01); A61B 34/71 (2016.02);
(Continued)

(58) Field of Classification Search
None
See application file for complete search history.

(56) References Cited

U.S. PATENT DOCUMENTS 4,082,244 A * 4/1978 Groff ..................... A61G 15/16
                                                248/281.11
4,494,177 A * 1/1985 Matthews ............... F21V 21/26
                                                362/402

(Continued)

FOREIGN PATENT DOCUMENTS

WO        0145627 A1      6/2001
WO     2001056490 A1      8/2001

OTHER PUBLICATIONS

"Secure, v." OED Online, Oxford University Press, Mar. 2023, www.oed.com/view/Entry/174648. Accessed Mar. 12, 2023. (Year: 2023).*

(Continued)

*Primary Examiner* — Christopher Koharski
*Assistant Examiner* — Farouk A Bruce
(74) *Attorney, Agent, or Firm* — Renner, Otto, Boisselle & Sklar, LLP

(57) ABSTRACT

A support arm for a medical device support system. The support arm includes a proximal hub, a distal hub, and an intermediate beam between the proximal hub and the distal hub. The intermediate beam having a cavity. A tension member extends through the cavity of the intermediate beam and is secured at opposite ends to the proximal hub and the distal hub to secure the proximal hub, the distal hub, and the intermediate beam together.

20 Claims, 46 Drawing Sheets

Related U.S. Application Data filed on Jan. 31, 2019, provisional application No. 62/799,202, filed on Jan. 31, 2019, provisional application No. 62/799,113, filed on Jan. 31, 2019.

(51) Int. Cl.

| | |
|---|---|
| *A61B 90/35* | (2016.01) |
| *F16D 65/06* | (2006.01) |
| *F16M 13/02* | (2006.01) |

(52) U.S. Cl.
CPC . *A61B 2034/715* (2016.02); *A61B 2090/5025* (2016.02); *A61B 2090/506* (2016.02); *A61B 2090/508* (2016.02); *F16D 65/065* (2013.01); *F16M 2200/022* (2013.01); *F16M 2200/041* (2013.01); *F16M 2200/066* (2013.01)

(56) References Cited

U.S. PATENT DOCUMENTS

| | | | |
|---|---|---|---|
| 5,460,894 A | 10/1995 | Muench et al. | |
| 5,845,885 A | 12/1998 | Carnevali | |
| 6,012,693 A * | 1/2000 | Voeller | F16M 11/048 248/920 |
| 7,004,437 B2 | 2/2006 | Bauer et al. | |
| 7,142,415 B2 | 11/2006 | Hillman et al. | |
| 7,551,432 B1 * | 6/2009 | Bockheim | F16M 11/2014 361/679.07 |
| 2003/0056382 A1 * | 3/2003 | Stahl, III | F16M 11/08 33/333 |
| 2004/0188578 A1 | 9/2004 | Turner | |
| 2005/0132935 A1 * | 6/2005 | Lahmann | A47B 23/00 108/49 |
| 2006/0023324 A1 * | 2/2006 | Otsuka | A61B 90/50 359/871 |
| 2008/0237414 A1 * | 10/2008 | Lien | F16M 11/10 248/125.2 |
| 2011/0303812 A1 * | 12/2011 | Rothschild | A47B 91/02 248/297.31 |

OTHER PUBLICATIONS

International Search Report and Written Opinion for corresponding International Application PCT/US2019/064390 mailed Mar. 17, 2020.

* cited by examiner

1700

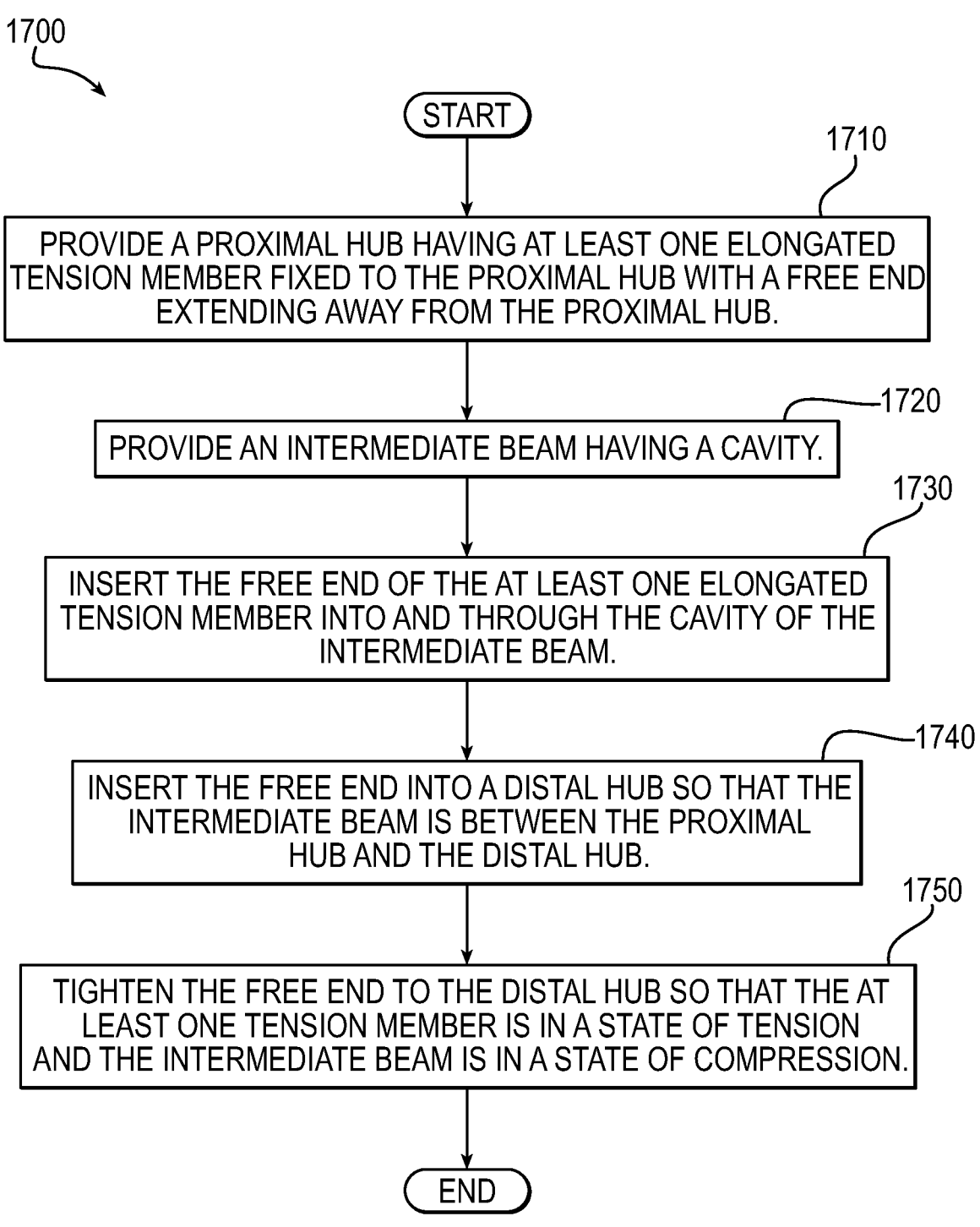

START

1710

PROVIDE A PROXIMAL HUB HAVING AT LEAST ONE ELONGATED TENSION MEMBER FIXED TO THE PROXIMAL HUB WITH A FREE END EXTENDING AWAY FROM THE PROXIMAL HUB.

1720

PROVIDE AN INTERMEDIATE BEAM HAVING A CAVITY.

1730

INSERT THE FREE END OF THE AT LEAST ONE ELONGATED TENSION MEMBER INTO AND THROUGH THE CAVITY OF THE INTERMEDIATE BEAM.

1740

INSERT THE FREE END INTO A DISTAL HUB SO THAT THE INTERMEDIATE BEAM IS BETWEEN THE PROXIMAL HUB AND THE DISTAL HUB.

1750

TIGHTEN THE FREE END TO THE DISTAL HUB SO THAT THE AT LEAST ONE TENSION MEMBER IS IN A STATE OF TENSION AND THE INTERMEDIATE BEAM IS IN A STATE OF COMPRESSION.

END

FIG. 57

SUPPORT ARM FOR MEDICAL DEVICE SUPPORT SYSTEM

This application claims priority to U.S. Patent Application No. 62/799,096 filed Jan. 31, 2019; U.S. Patent Application No. 62/799,100 filed Jan. 31, 2019; U.S. Patent Application No. 62/799,113 filed Jan. 31, 2019; and U.S. Patent Application No. 62/799,202 filed Jan. 31, 2019. These prior applications are incorporated herein by reference.

FIELD OF INVENTION

This application relates generally to a support arm for a medical device support system or carry system for use in, for example, a hospital examination room, a clinic, a surgery room or an emergency room, and more particularly to a support arm that is more compact and lighter in weight.

BACKGROUND

Medical device support systems, also referred to as suspension systems and carry systems, are used in health treatment settings such as hospital examination rooms, clinics, surgery rooms and emergency rooms. These systems may suspend or support any variety of medical devices or components including surgical lights, supply consoles, patient monitors, camera detector heads, medical instruments, ventilator systems, suction devices, among others. The support systems typically include a central shaft or support column that is suspended from the ceiling or mounted to a wall, one or more generally horizontal extension arms mounted for rotational movement about the shaft, and one or more load balancing arms, also known as counterbalancing arms, that enable positioning of a medical device to a proper orientation relative to for example a patient operating table and healthcare professionals in the operating room. The extension arms and load balancing arms each include a support arm structure or housing, or more generally a support arm.

For support arms in some medical device support systems or carry systems, there remain various shortcomings, drawbacks, and disadvantages relative to certain applications. A support arm may include a proximal hub, a distal hub, and an intermediate beam between the proximal hub and distal hub. The proximal hub and distal hub connect to the intermediate beam by means of bolts. The mounting structure in the intermediate beam may consist of a plurality of threaded hole bosses on an inward facing wall of the intermediate beam, and the mounting structure in the proximal hub and distal hub may consist of a plurality of clearance hole bosses on an inward facing wall of the hubs. The bolts pass through the clearance holes of the hub bosses and thread into the threaded bosses of the intermediate beam thereby to fasten the hubs to the intermediate beam.

One problem is that the bolts and their mounting structure, such as the bosses on the inward facing walls of the components, can occupy a significant amount of space. The space footprint ultimately affects the overall profile of the support arm. Generally, the larger the space occupied by the mounting structure, the larger is the profile of the support arm. This is undesirable not only in terms of aesthetics but also in terms of industry demands to provide smaller more streamlined medical device support systems in health treatment facilities. A larger mounting structure and thus larger profile support arm also is more obstructive of laminar flow in the operating theater, making reduced volume components more desirable.

The mounting structure also contributes to the overall weight of the support arm. For example, the intermediate beam of the support arm requires material for drilling and tapping. Further, the material in the corresponding proximal hub and distal hub must have a thickness that is at least wide enough to support the head of the fastening member. Where the intermediate beam is an extruded member the material of the mounting structure, for example the bosses, may extend the entire length of the intermediate beam. A lighter weight support arm is desirable for several reasons. Lighter weight support arms are easier for healthcare professionals to manipulate. They are also easier for technicians to assemble and service.

A further problem with some mounting structures is that their mounting fasteners may be visible. Increasingly, the industry has sought to minimize the quantity of visible fasteners.

Accordingly, there remains a need for further contributions in this area of technology.

SUMMARY OF INVENTION

The application relates to a support arm, such as an extension arm or load balancing arm, for a medical device support system, in which the support arm utilizes a tension member that holds its structure together and allows for a more compact and lighter weight support arm than what was heretofore provided, and a support arm that has no visible fasteners.

According to one aspect of the invention, a support arm for a medical device support system, includes a proximal hub and a distal hub; an intermediate beam between the proximal hub and the distal hub, the intermediate beam having a cavity; and, at least one tension member extending through the cavity of the intermediate beam and secured at opposite ends to the proximal hub and the distal hub, the tension member securing the proximal hub, the distal hub, and the intermediate beam together.

Embodiments of the invention may include one or more of the following additional features separately or in combination.

The at least one tension member may be in a state of tension and the intermediate beam may be in a state of compression.

The at least one tension member may not contact or engage the intermediate beam.

The at least one tension member may comprise any quantity of tension members, such as four tension members.

The at least one tension member may comprise at least two tension members that have different lengths.

The proximal hub may include at least one threaded hole and the at least one tension member may be a threaded tension member that threads into the at least one threaded hole.

The distal hub may include at least one clearance hole and the least one tension member may pass through the at least one clearance hole such that an end of the at least one tension member is exposed.

The at least one tension member may be a threaded tension member, and the support arm may further include a retainer that threads onto the exposed end and abuts a flat of the distal hub.

The retainer may comprise a cylindrical nut.

The at least one tension member may be selected from the group consisting of a threaded rod, a steel cable, and a plastic cable.

The proximal hub may include a noncircular tubular end wall that fits into a corresponding shape end wall of the intermediate beam such that the noncircular tubular end wall overlaps with the corresponding shape end wall.

The noncircular tubular end wall may have a shoulder and the corresponding shape end wall of the intermediate beam may have a stop face that abuts the shoulder.

The proximal hub may include an end wall with a shoulder and the intermediate beam may include an end wall with a stop face that abuts the shoulder.

The intermediate beam may have a noncircular tubular shape in axial cross section.

The proximal hub may include upper and lower plugs that fit into respective upper and lower receptacles of the intermediate beam.

The intermediate beam may be an extruded member.

The proximal hub may be a cast member.

According to another aspect of the invention, there is provided a method of assembling a support arm of a medical device support system, including providing a proximal hub having at least one elongated tension member fixed to the proximal hub with a free end extending away from the proximal hub; providing an intermediate beam having a cavity; inserting the free end of the at least one elongated tension member into and through the cavity of the intermediate beam; inserting the free end into a distal hub so that the intermediate beam is between the proximal hub and the distal hub; and, tightening the free end to the distal hub so that the at least one tension member is in a state of tension and the intermediate beam is in a state of compression.

Embodiments of the invention may include one or more of the following additional features separately or in combination.

The free end of the at least one tension member may be a threaded end and the tightening may include tightening a threaded nut onto the threaded end.

The inserting the free end into the distal hub may include inserting the free end into a clearance hole inside the distal hub.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention.

4

Figure 2:
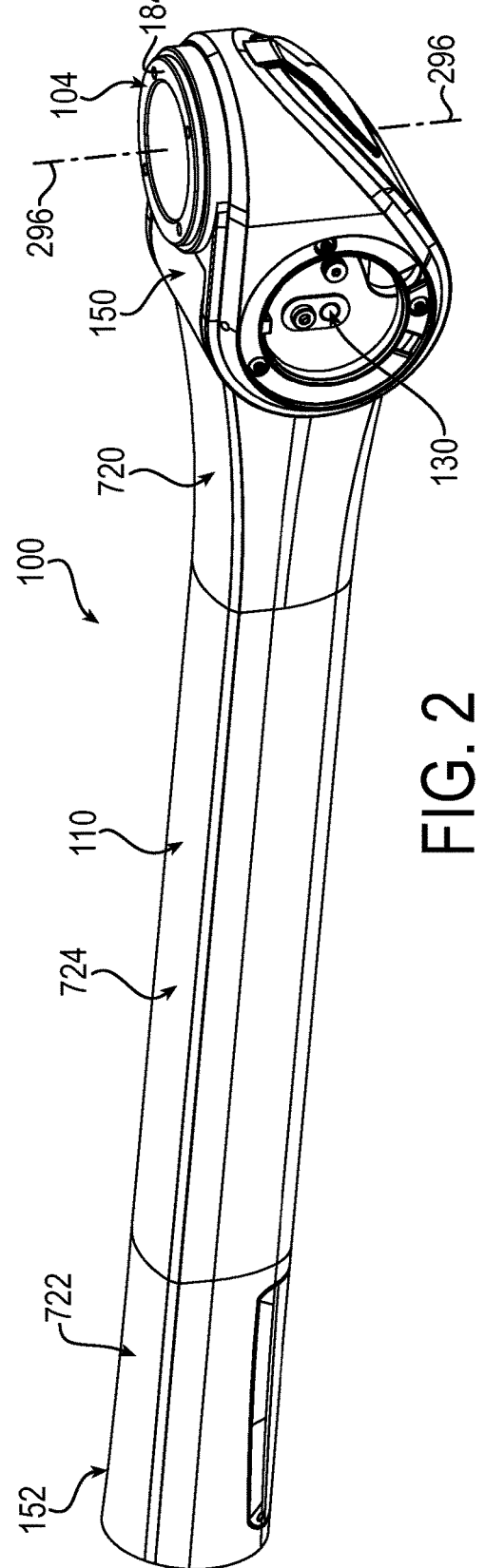
FIG. 2 is a side perspective view of a load balancing arm in accordance with an embodiment of the invention.
Figure 4:
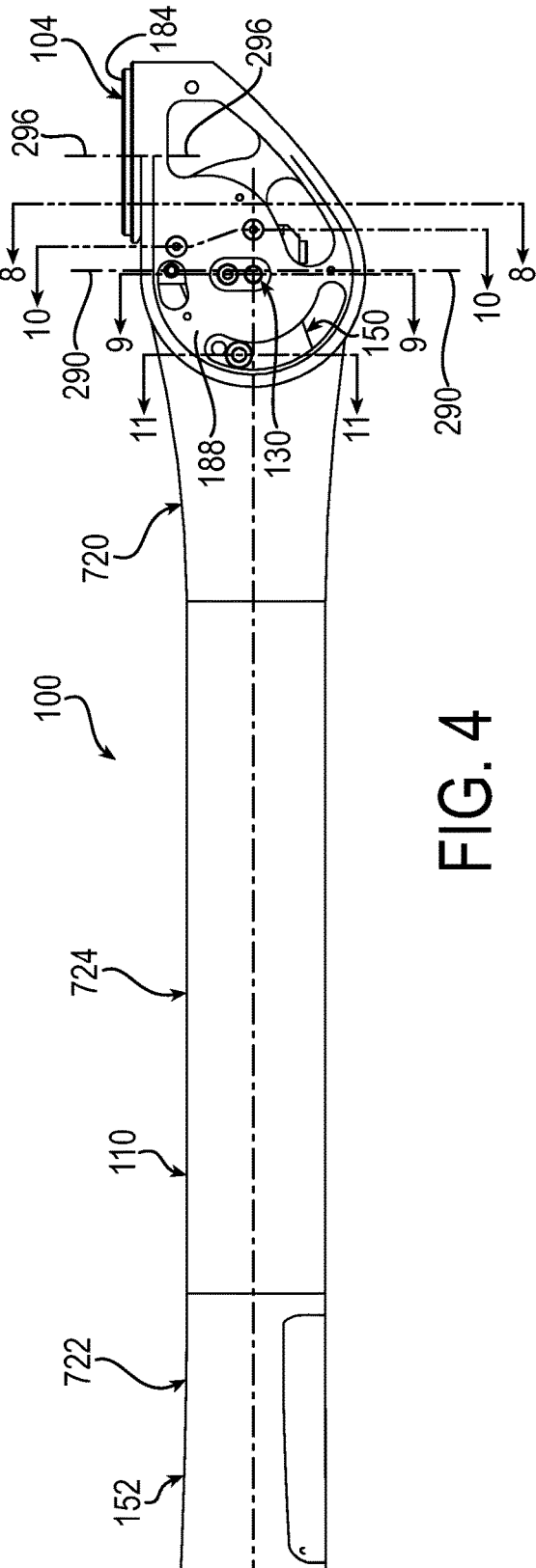
FIG. 4 is a side view of the FIG. 2 load balancing arm.
Figure 8:
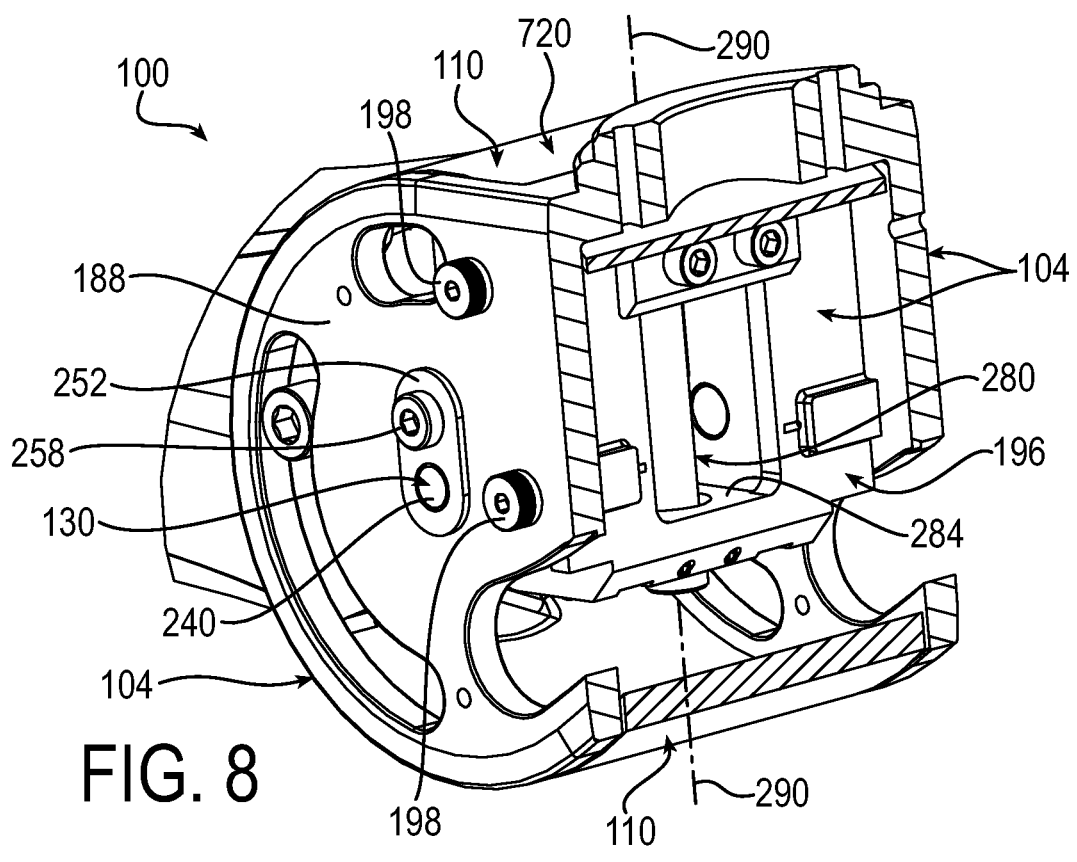

FIG. 8 is a cross section view of the FIG. 2 load balancing arm as viewed from the plane 8-8 in FIG. 4.

Figure 9:
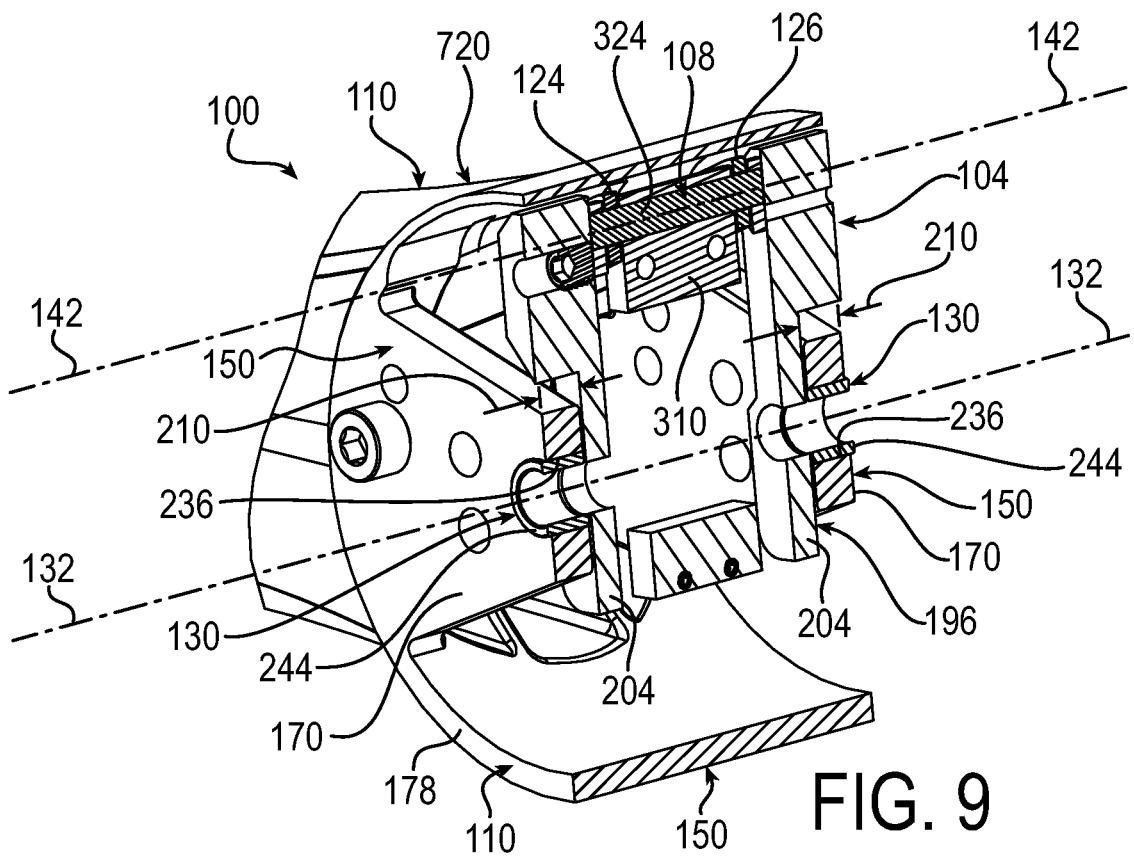

FIG. 9 is a cross section view of the FIG. 2 load balancing arm as viewed from the plane 9-9 in FIG. 4, without the proximal hub to show internal components of the load balancing arm.

Figure 10:
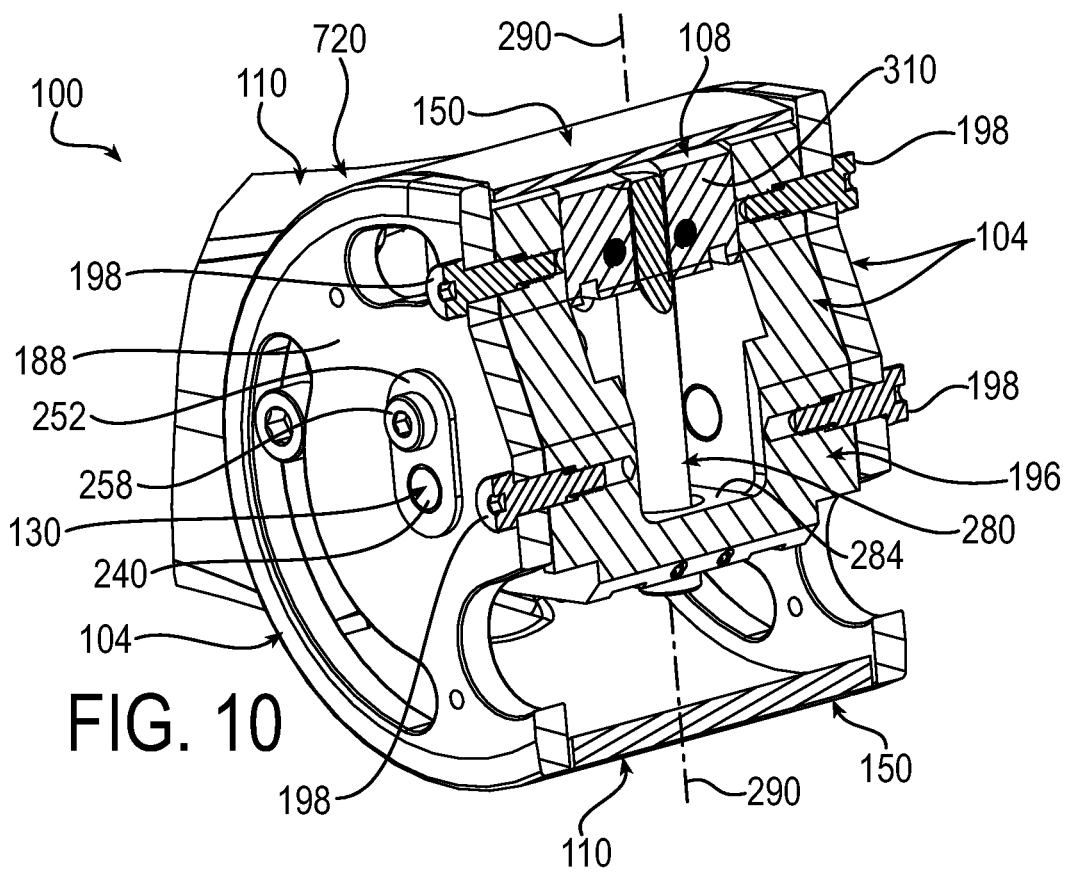

FIG. 10 is a cross section view of the FIG. 2 load balancing arm as viewed from the plane 10-10 in FIG. 4.

Figure 11:
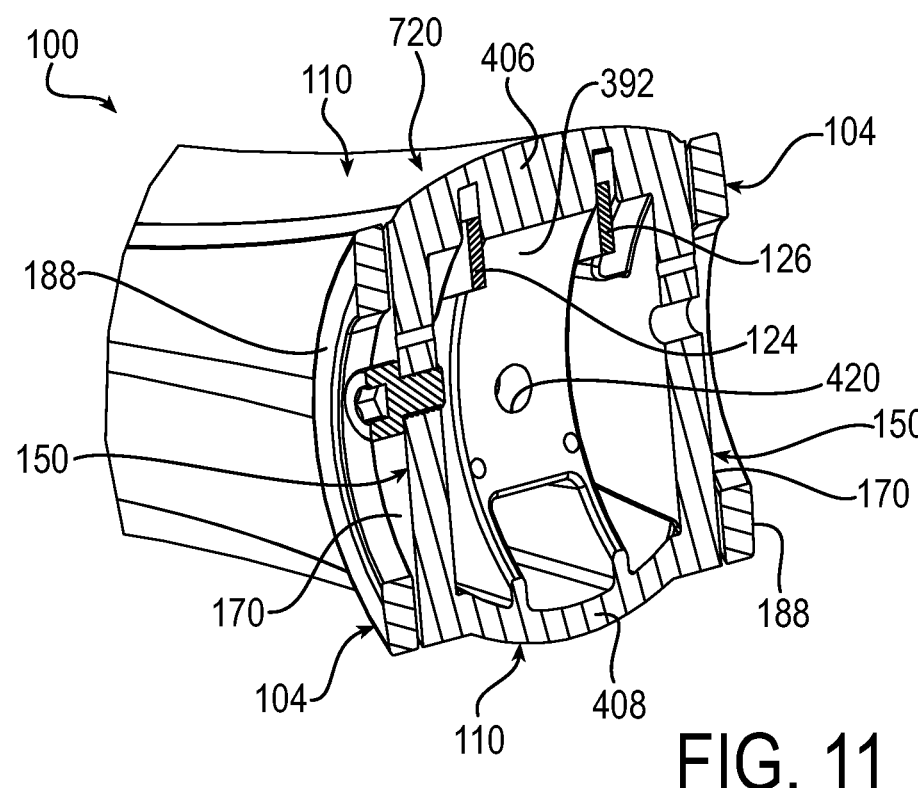

FIG. 11 is a cross section view of the FIG. 2 load balancing arm as viewed from the plane 11-11 in FIG. 4.

Figure 12:
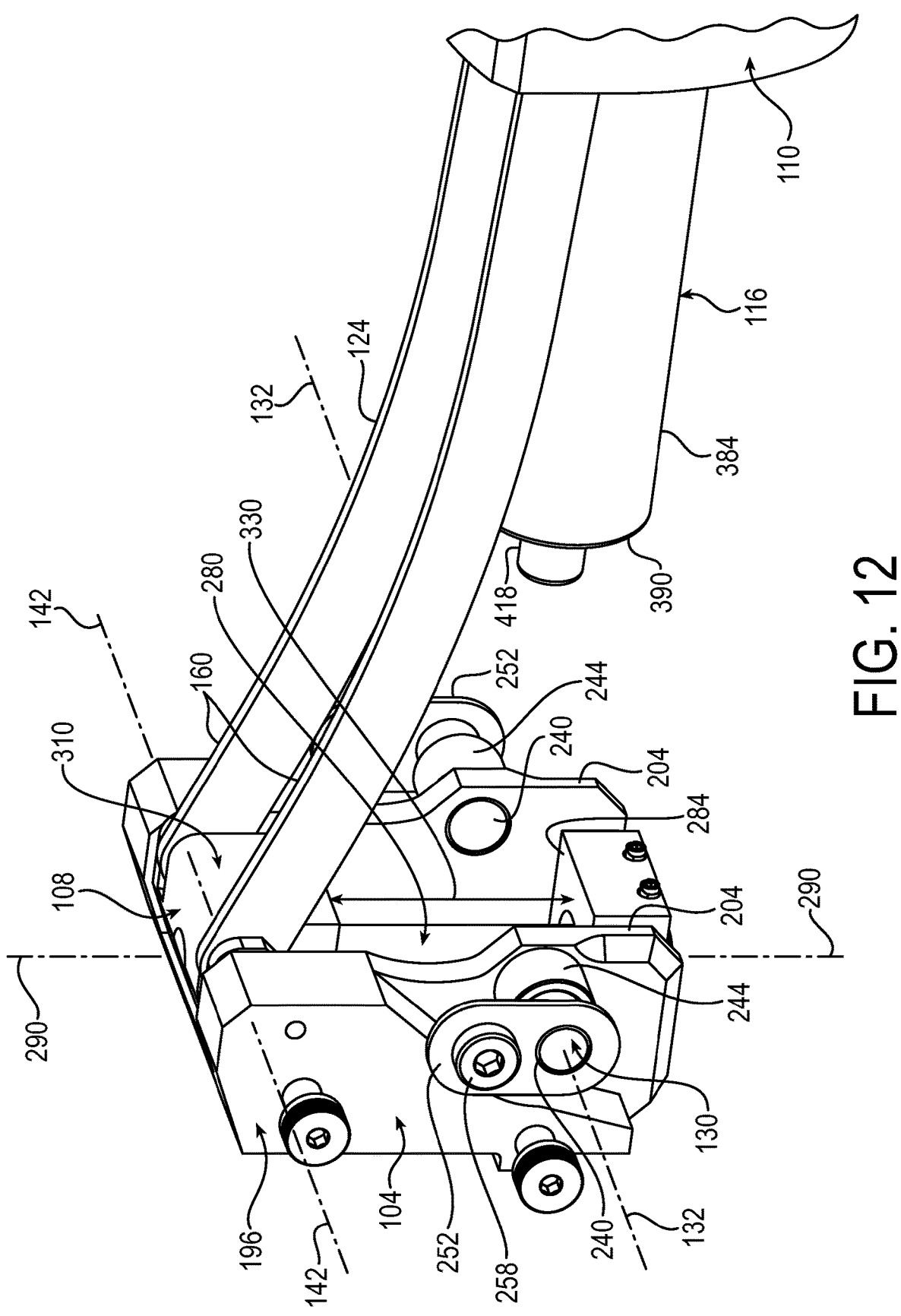

FIG. 12 is a perspective view of a proximal end of the load balancing arm, showing internal components of the load balancing arm.

Figure 13:
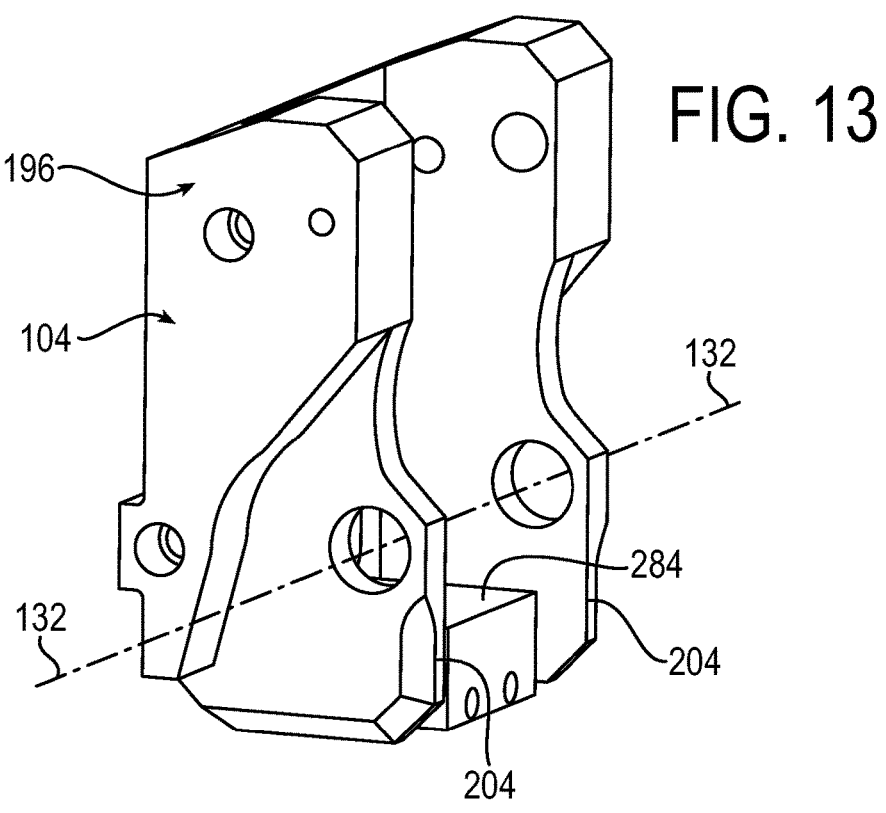

FIG. 13 is a side perspective view of a load adjustment block of a proximal hub of the FIG. 2 load balancing arm.

Figure 14:
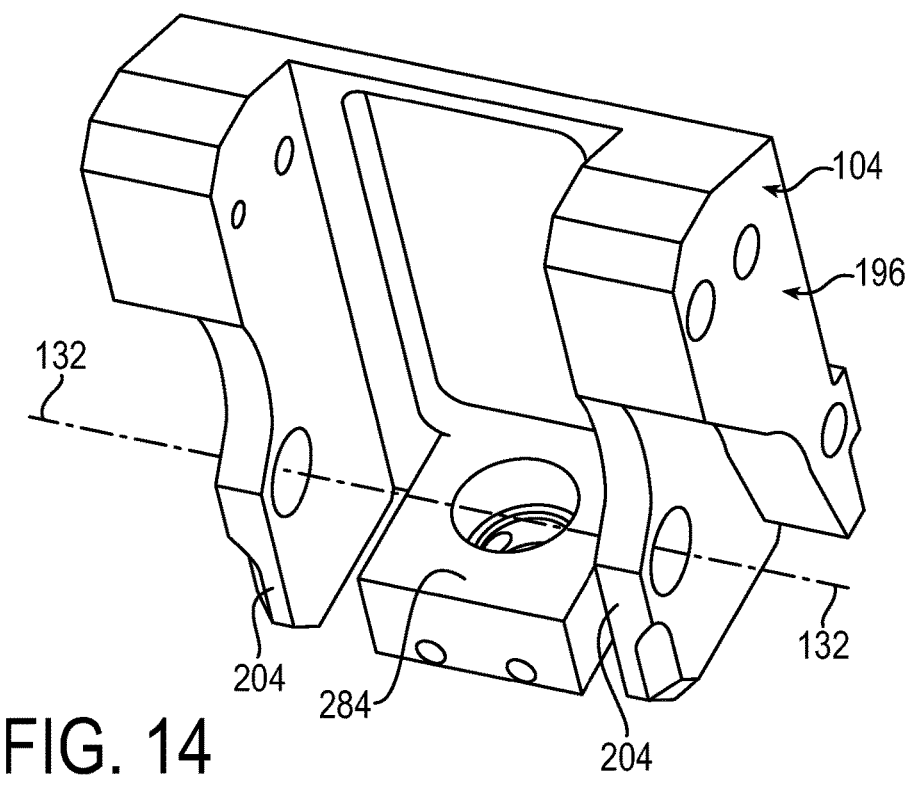

FIG. 14 is a top perspective view of the load adjustment block of the proximal hub of the FIG. 2 load balancing arm.

Figure 15:
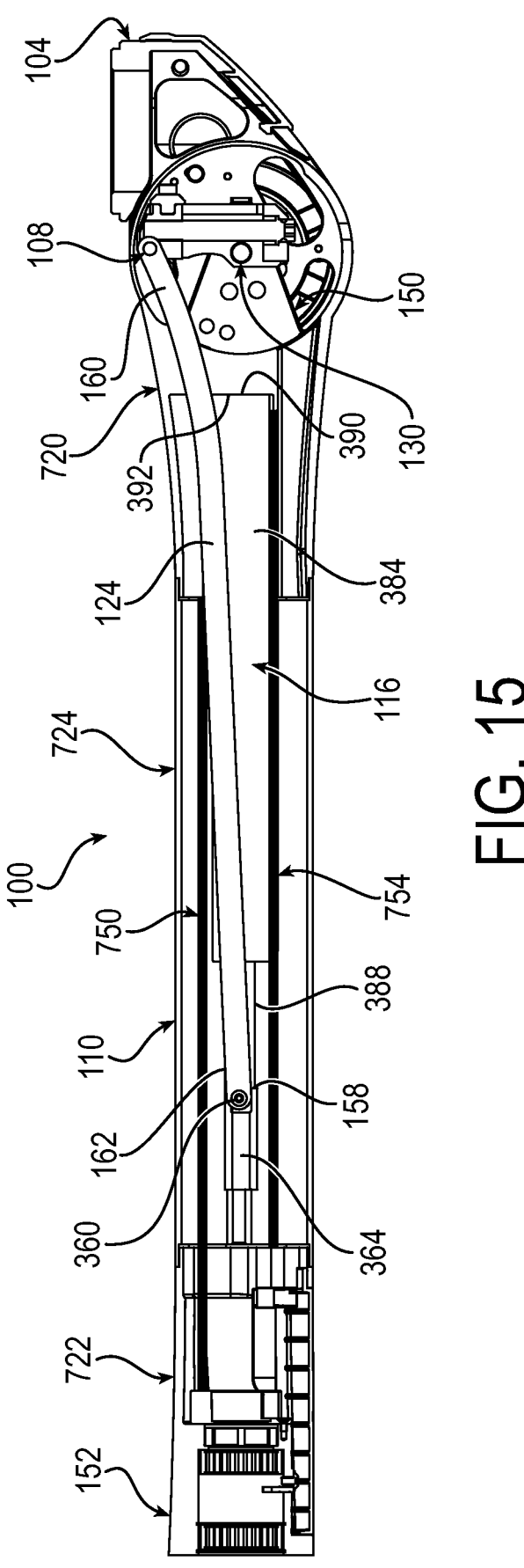

FIG. 15 is a side cross section view of the FIG. 2 load balancing arm in a substantially horizontal position, showing internal components of the load balancing arm.

Figure 16:
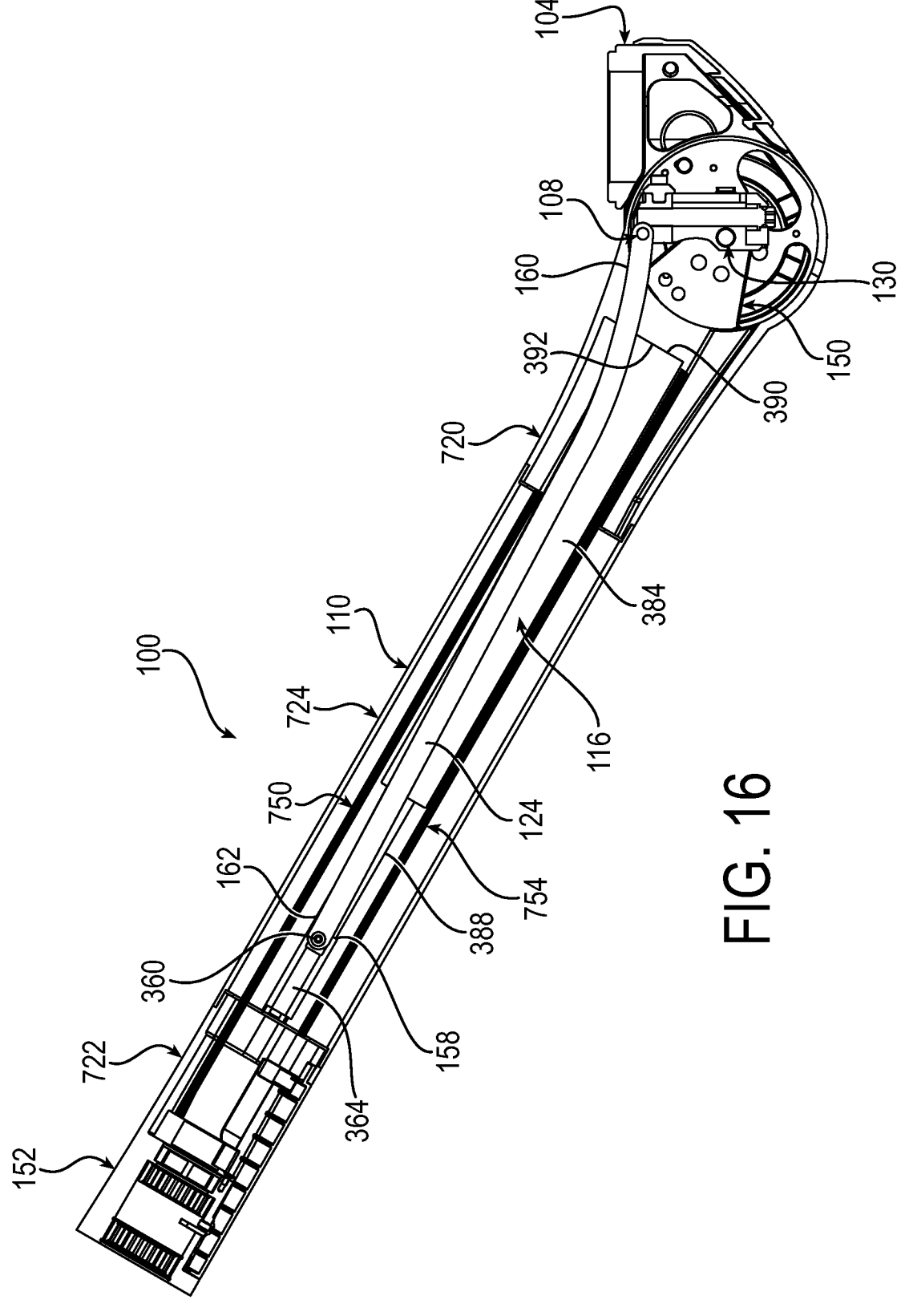

FIG. 16 is a side cross section view of the FIG. 2 load balancing arm in a position upward from horizontal, showing internal components of the load balancing arm.

Figure 17:
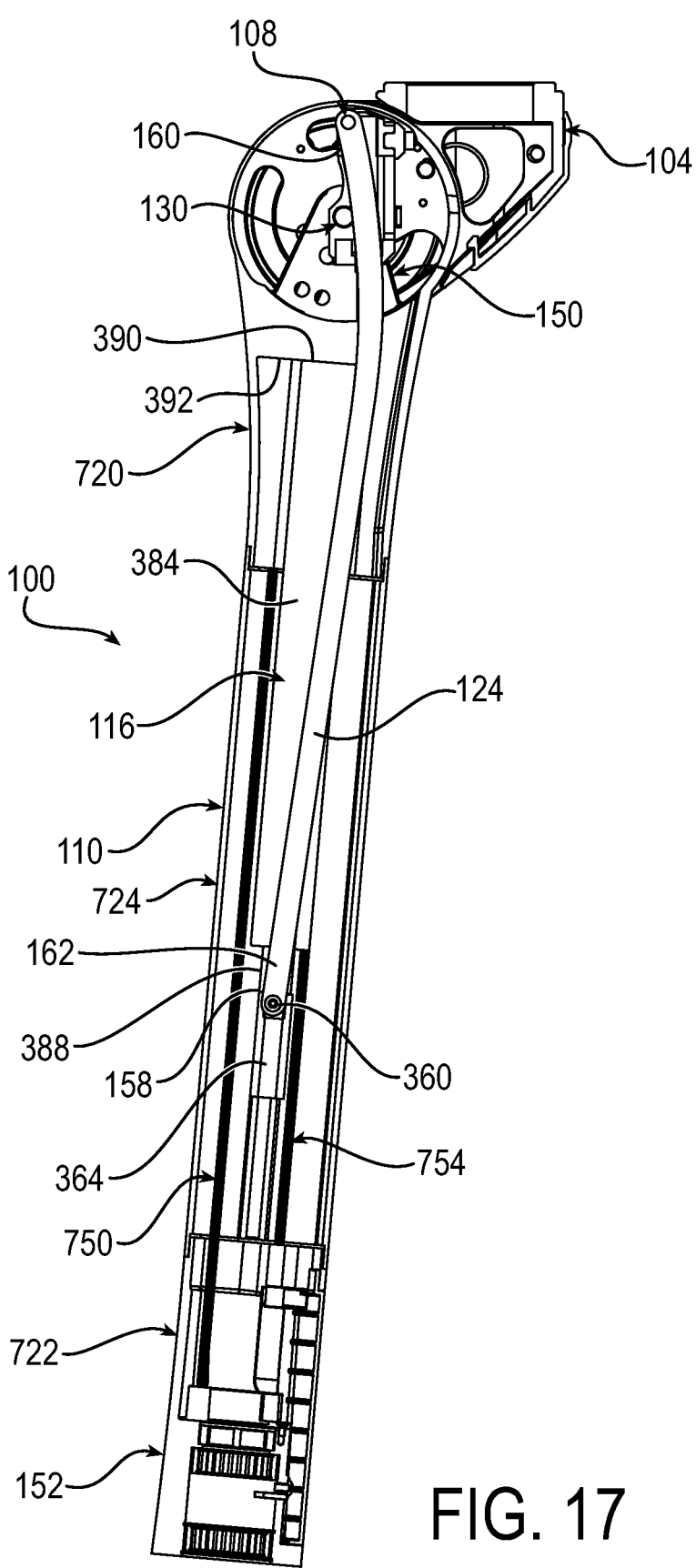

FIG. 17 is a side cross section view of the FIG. 2 load balancing arm in a position downward from horizontal, showing internal components of the load balancing arm.

Figure 18:
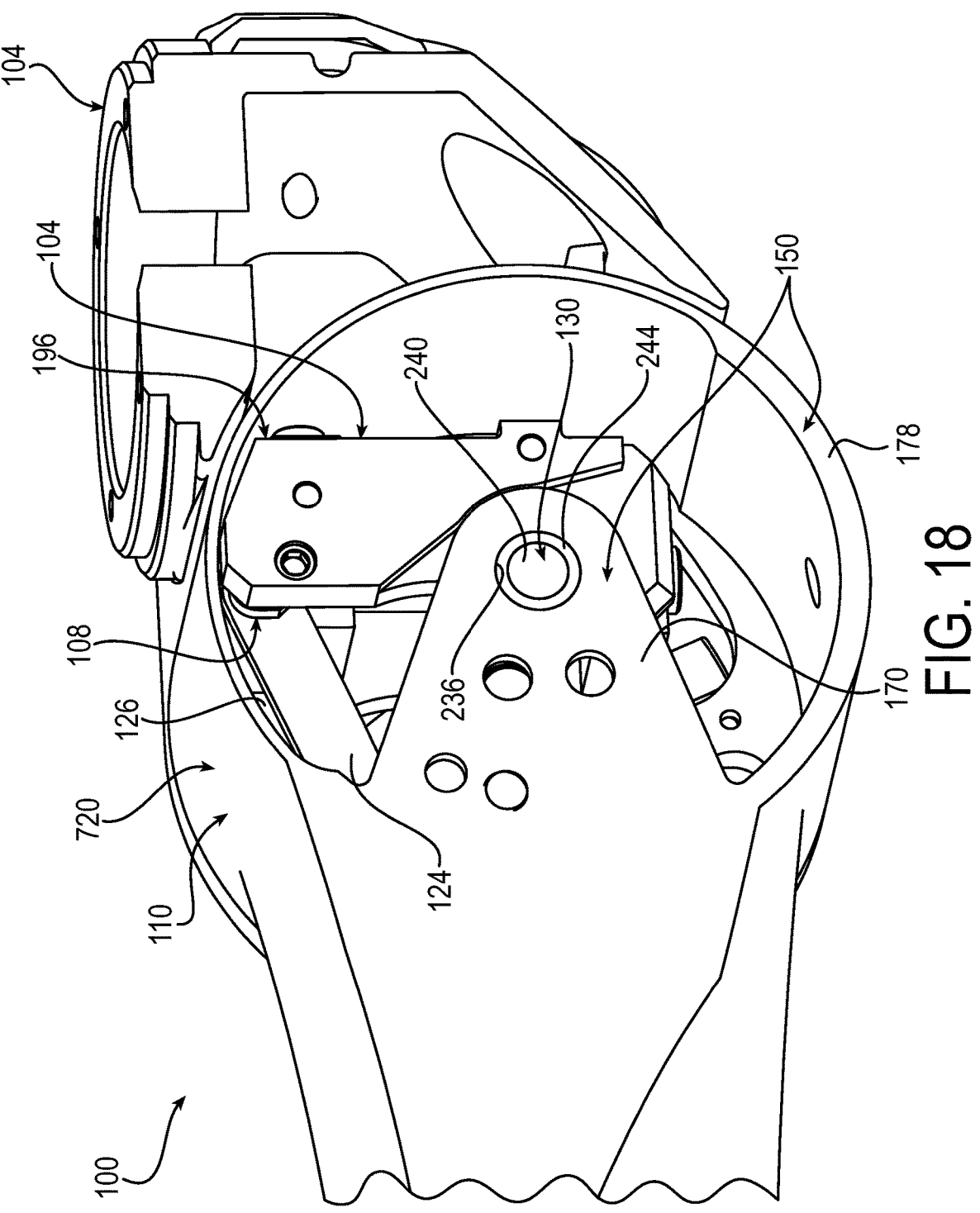

FIG. 18 is a perspective view of the proximal end of the FIG. 2 load balancing arm in a substantially horizontal position, with a cover removed to show internal components of the load balancing arm.

Figure 19:
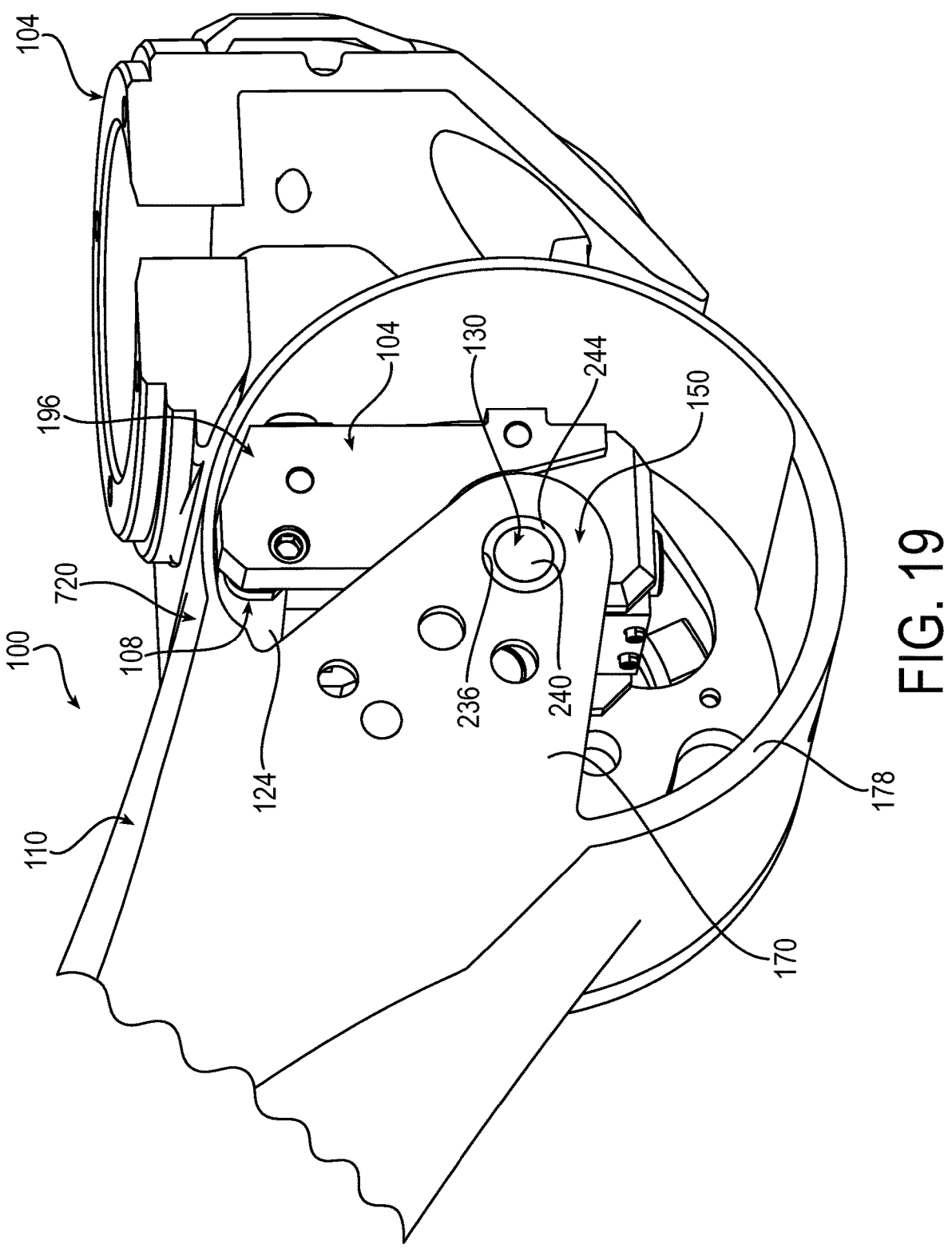

FIG. 19 is a perspective view of the proximal end of the FIG. 2 load balancing arm in a position upward from horizontal, with a cover removed to show internal components of the load balancing arm.

Figure 20:
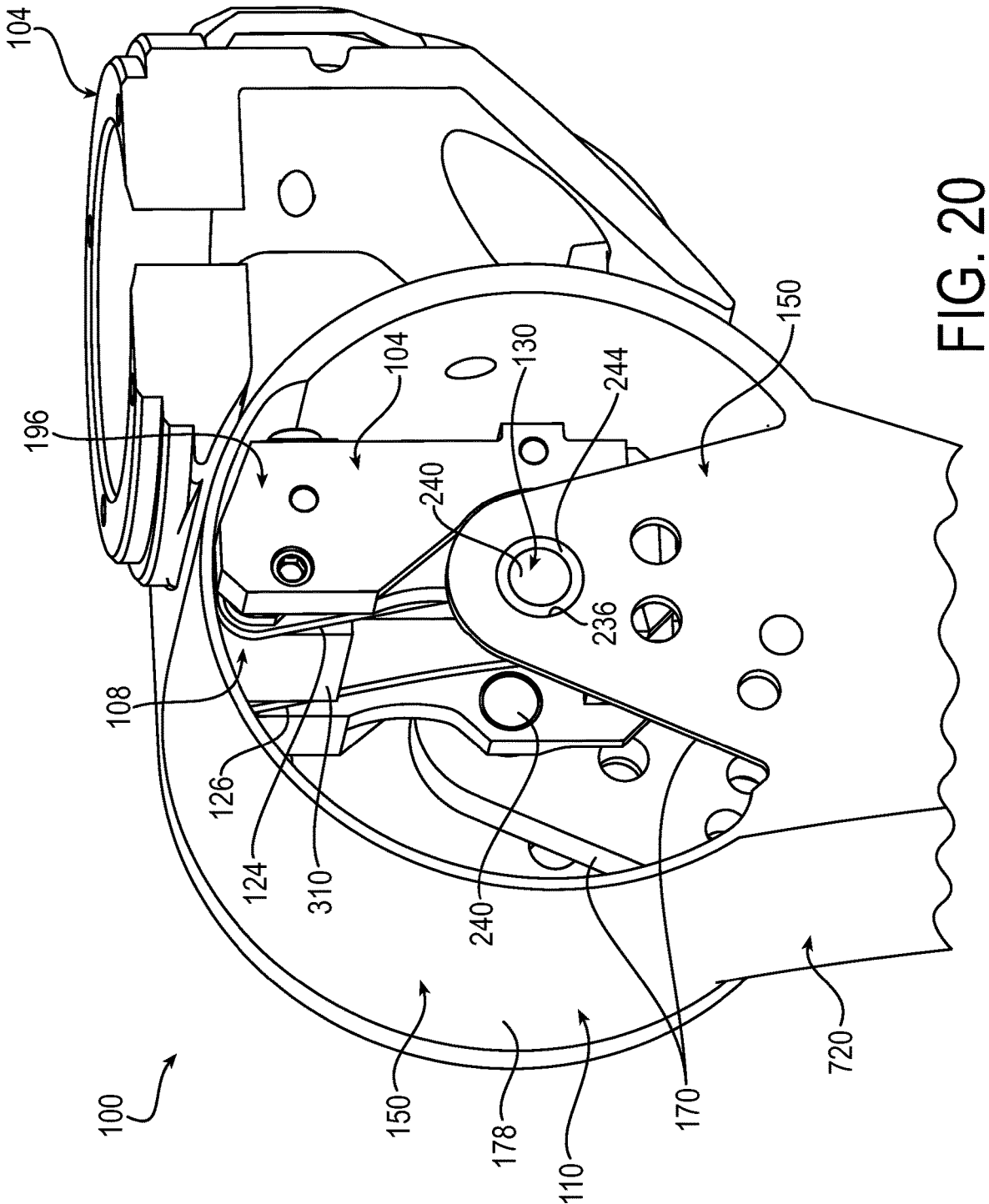

FIG. 20 is a perspective view of the proximal end of the FIG. 2 load balancing arm in a position downward from horizontal, with a cover removed to show internal components of the load balancing arm.

Figure 21:
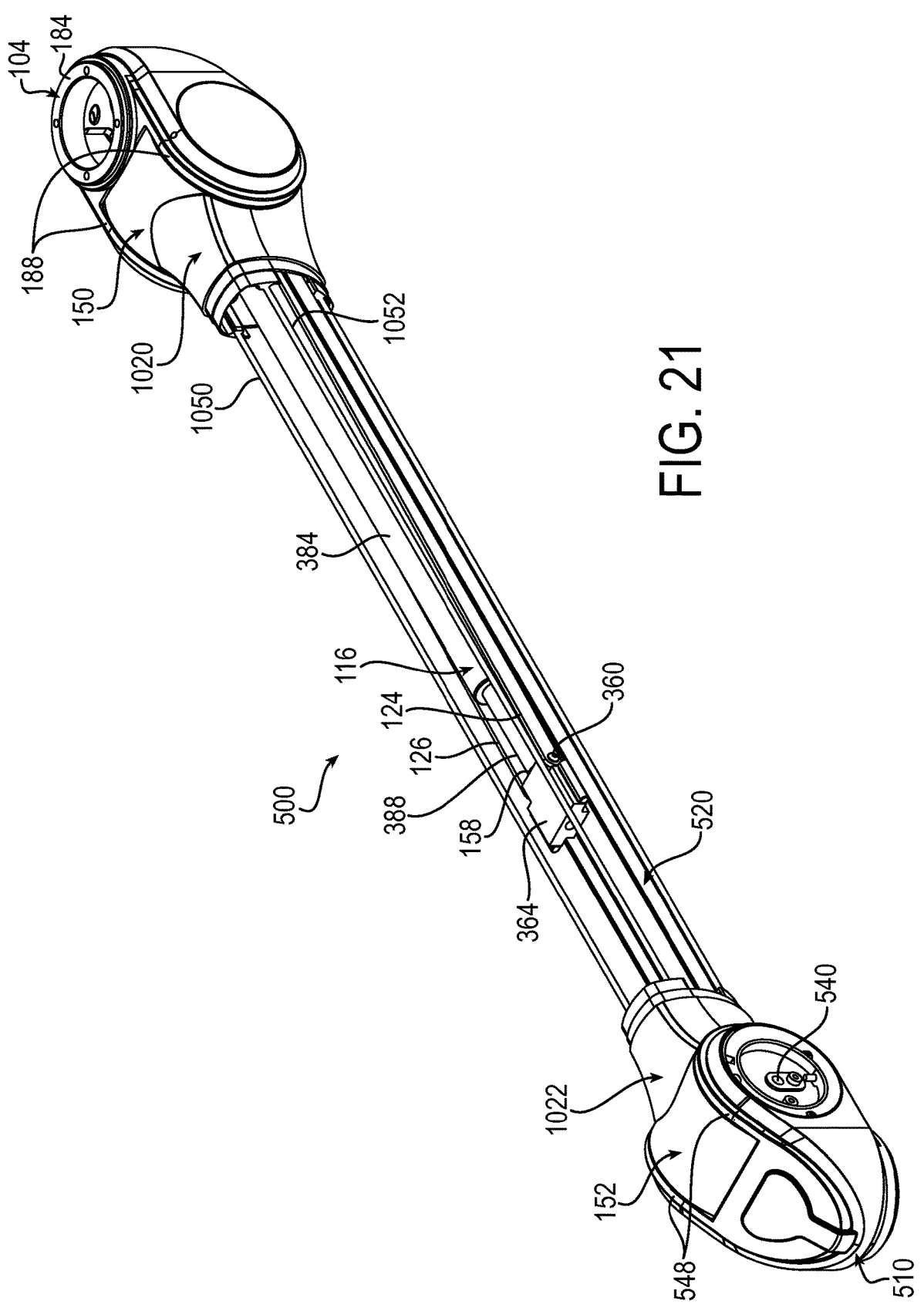

FIG. 21 is a top perspective view of a load balancing arm in accordance with another embodiment of the invention, with a support arm structure removed to show internal components of the load balancing arm.

Figure 22:
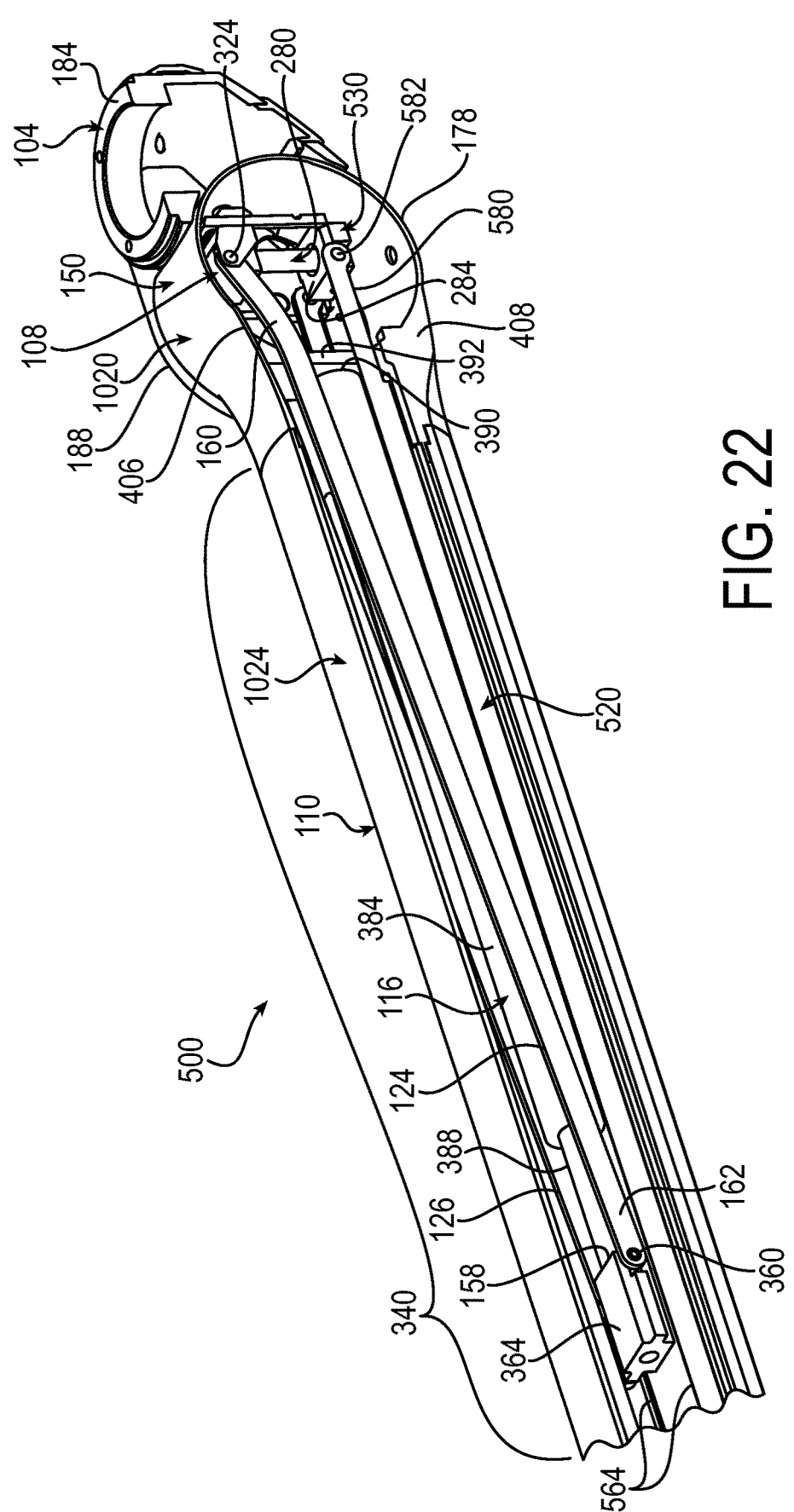

FIG. 22 is a partial top perspective view of the FIG. 21 load balancing arm, shown in partial cross section to show internal components of the load balancing arm.

Figure 23:
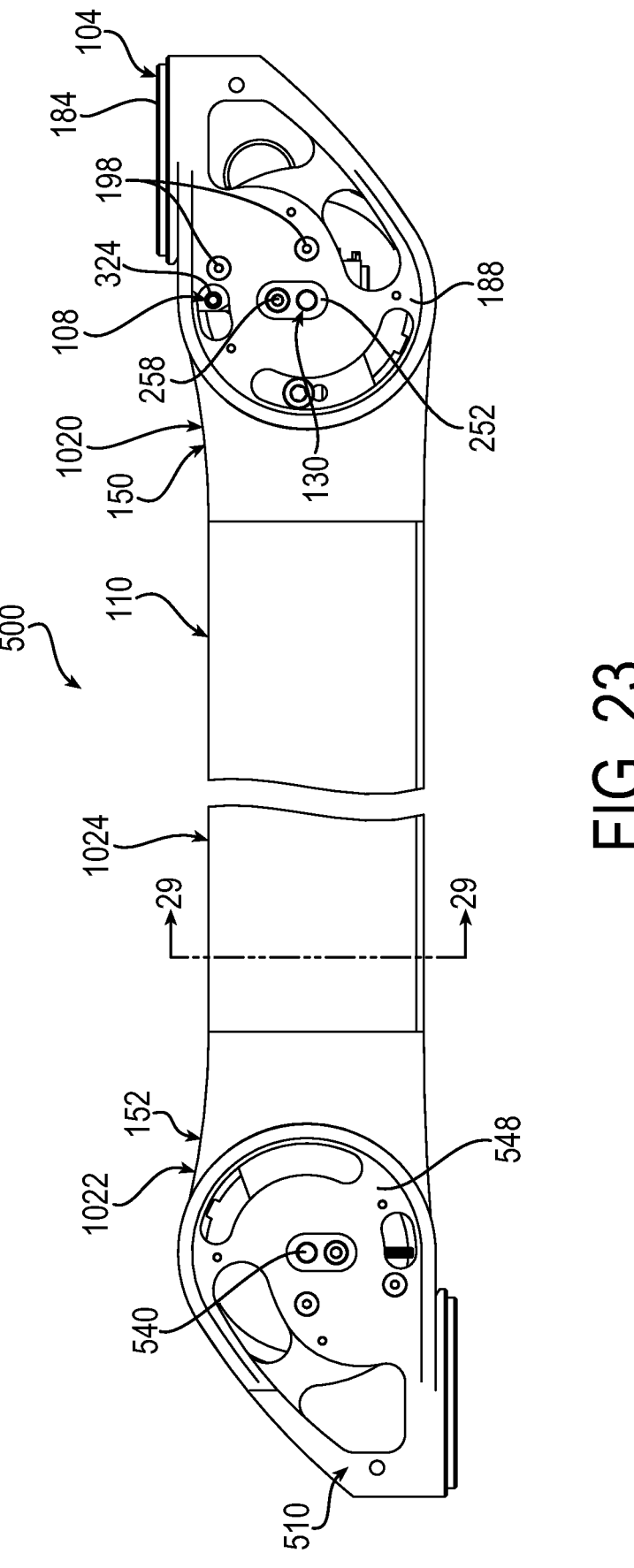

FIG. 23 is a side view of the FIG. 21 load balancing arm, enlarged to show the proximal and distal ends in more detail.

Figure 24:
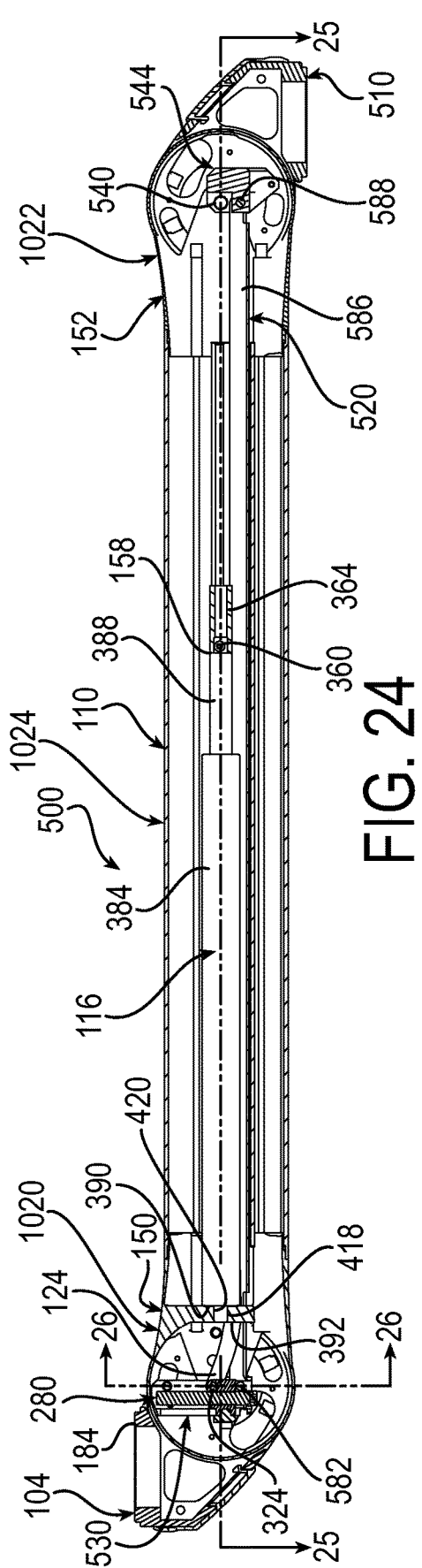
Figure 25:
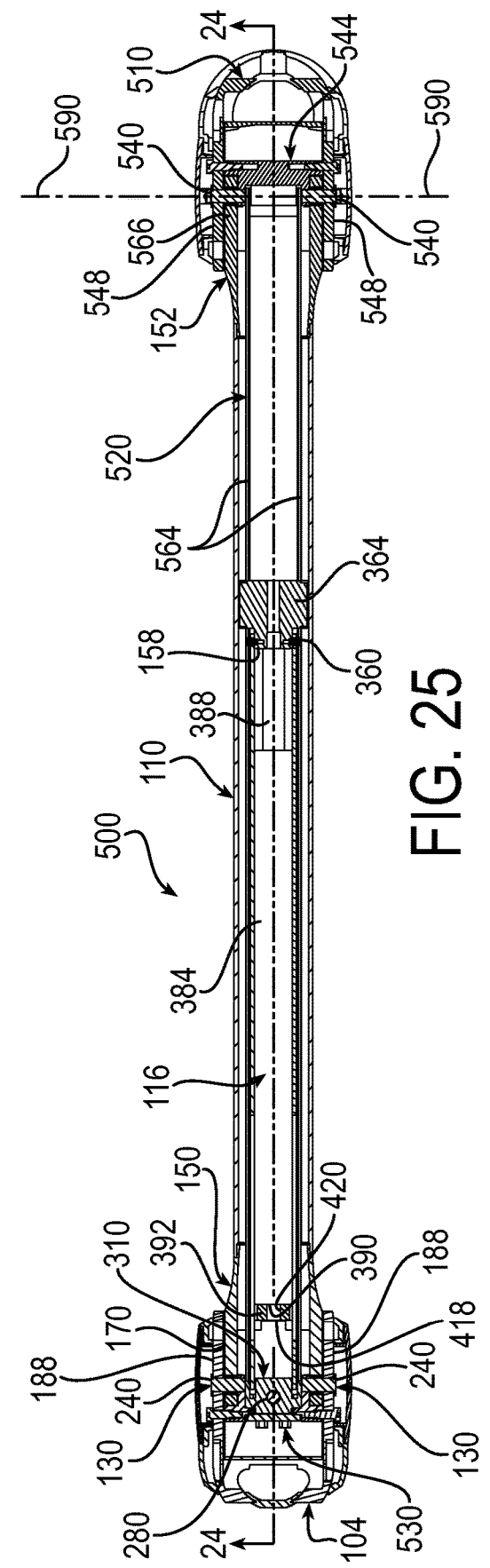

FIG. 24 is a side cross section view of the FIG. 21 load balancing arm as viewed from the plane 24-24 in FIG. 25, as though the load balancing arm in FIG. 25 were whole.

FIG. 25 is a top cross section side view of the FIG. 21 load balancing arm as viewed from the plane 25-25 in FIG. 24, as though the load balancing arm in FIG. 24 were whole.

Figure 26:
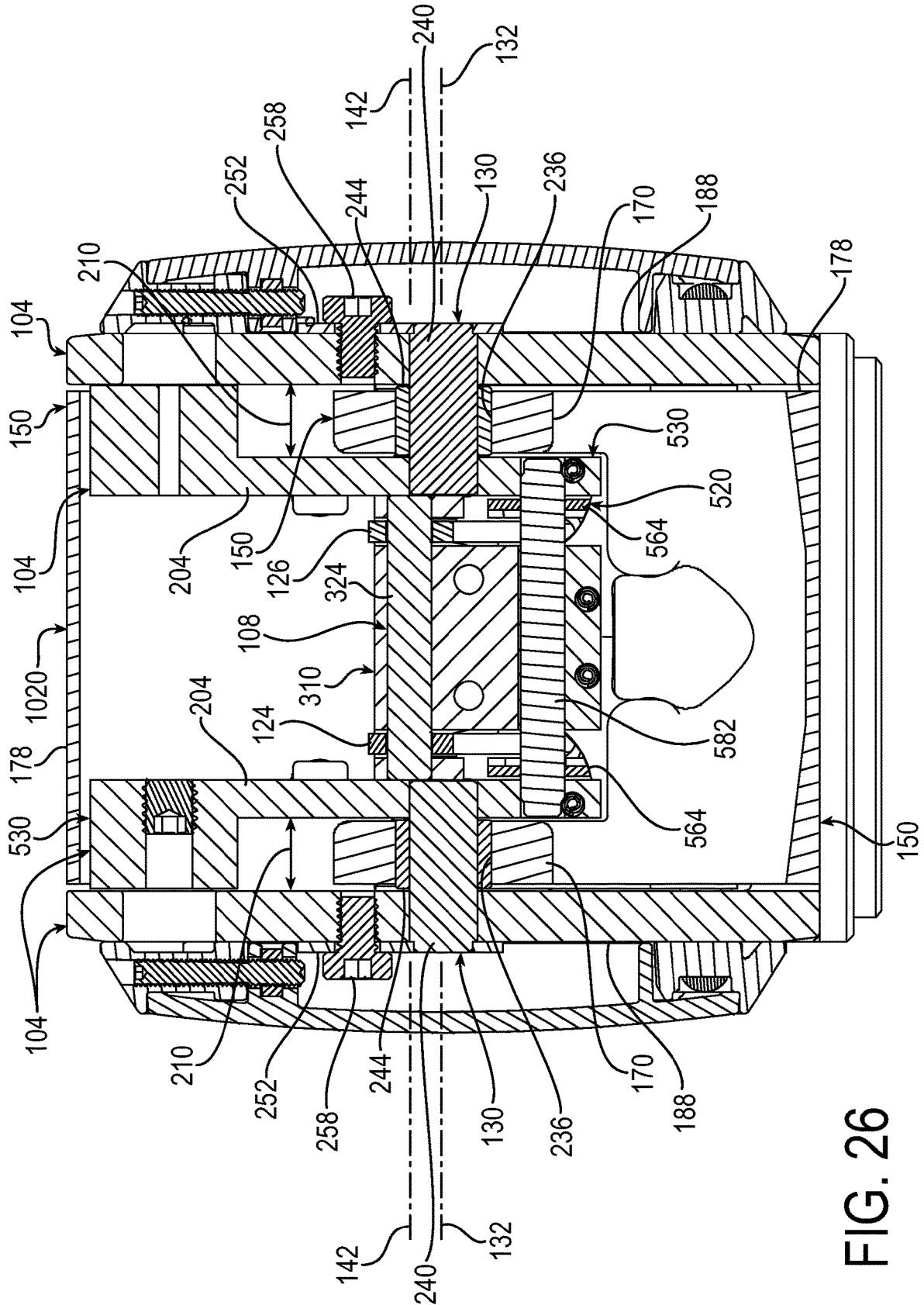

FIG. 26 is an end cross section view of the FIG. 21 load balancing arm as viewed from the plane 26-26 in FIG. 24, as though the load balancing arm in FIG. 24 were whole.

Figure 27:
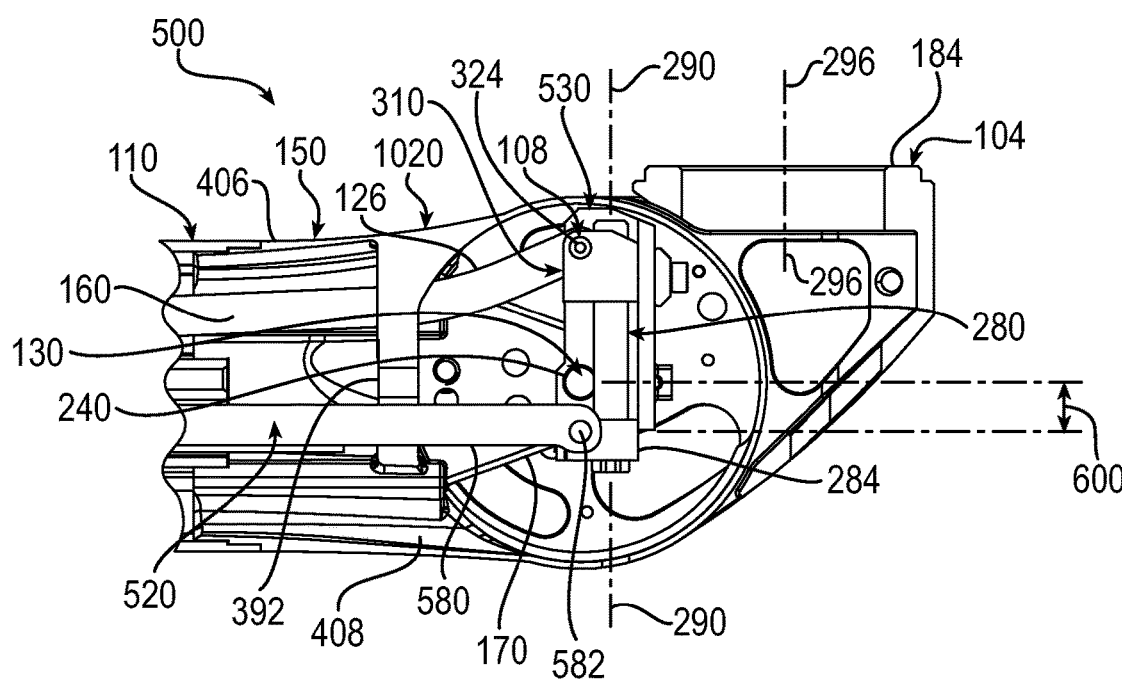

FIG. 27 is a side cross section view of a proximal end of the FIG. 21 load balancing arm, showing internal components of the load balancing arm.

Figure 28:
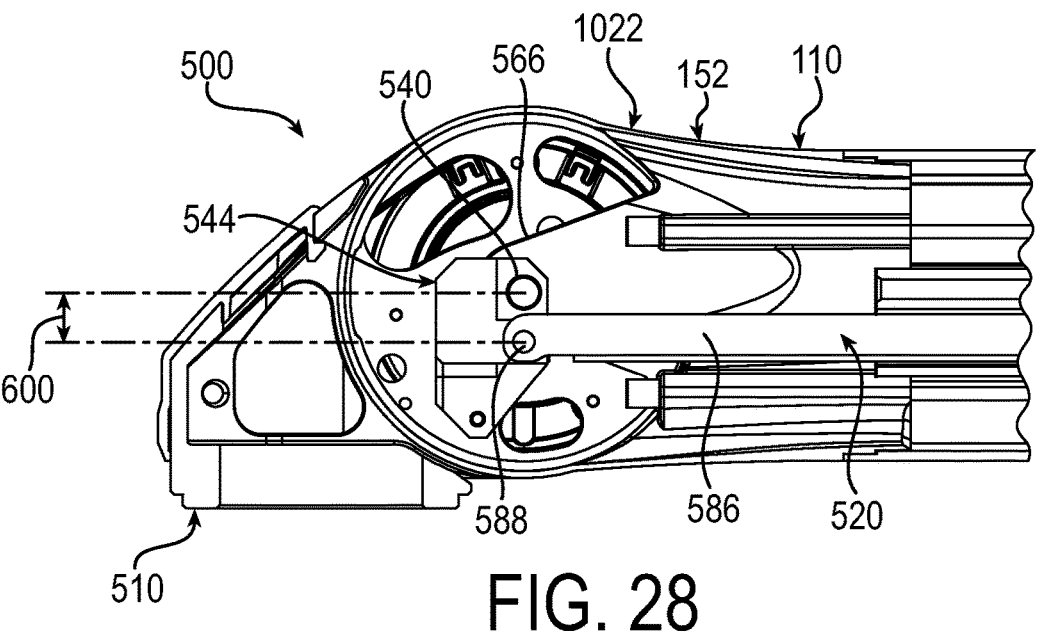

FIG. 28 is a side cross section view of a distal end of the FIG. 21 load balancing arm, showing internal components of the load balancing arm.

Figure 29:
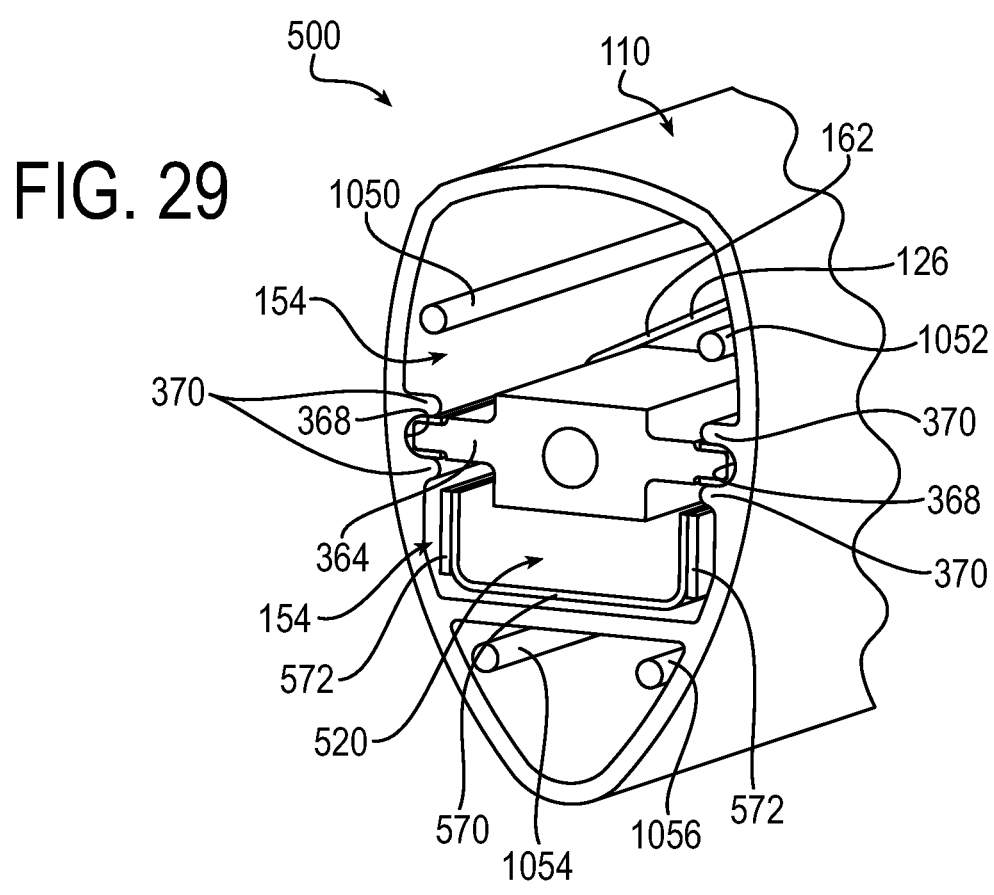

FIG. 29 is cross section view of the FIG. 21 load balancing arm as viewed from the plane 29-29 in FIG. 23.

Figure 30:
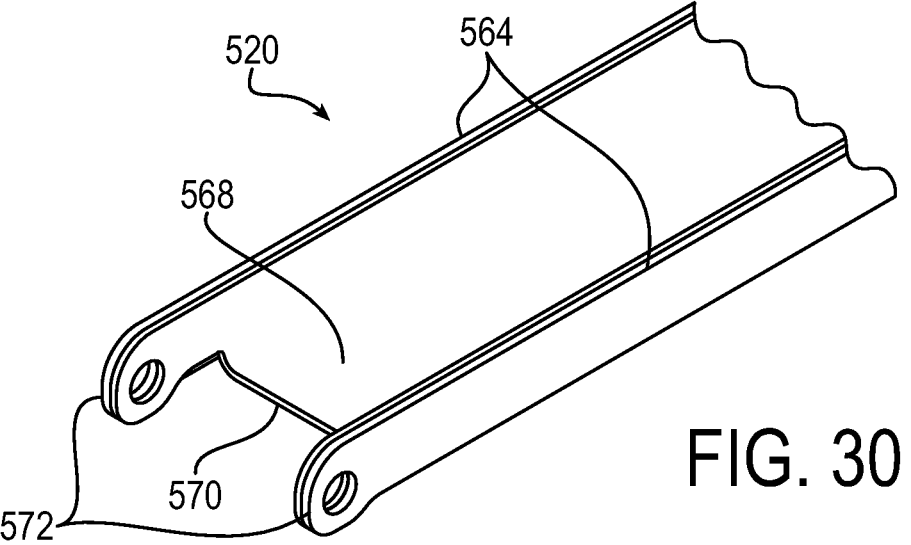

FIG. 30 is a perspective view of an end portion of a parallel link of the FIG. 21 load balancing arm.

Figure 31:
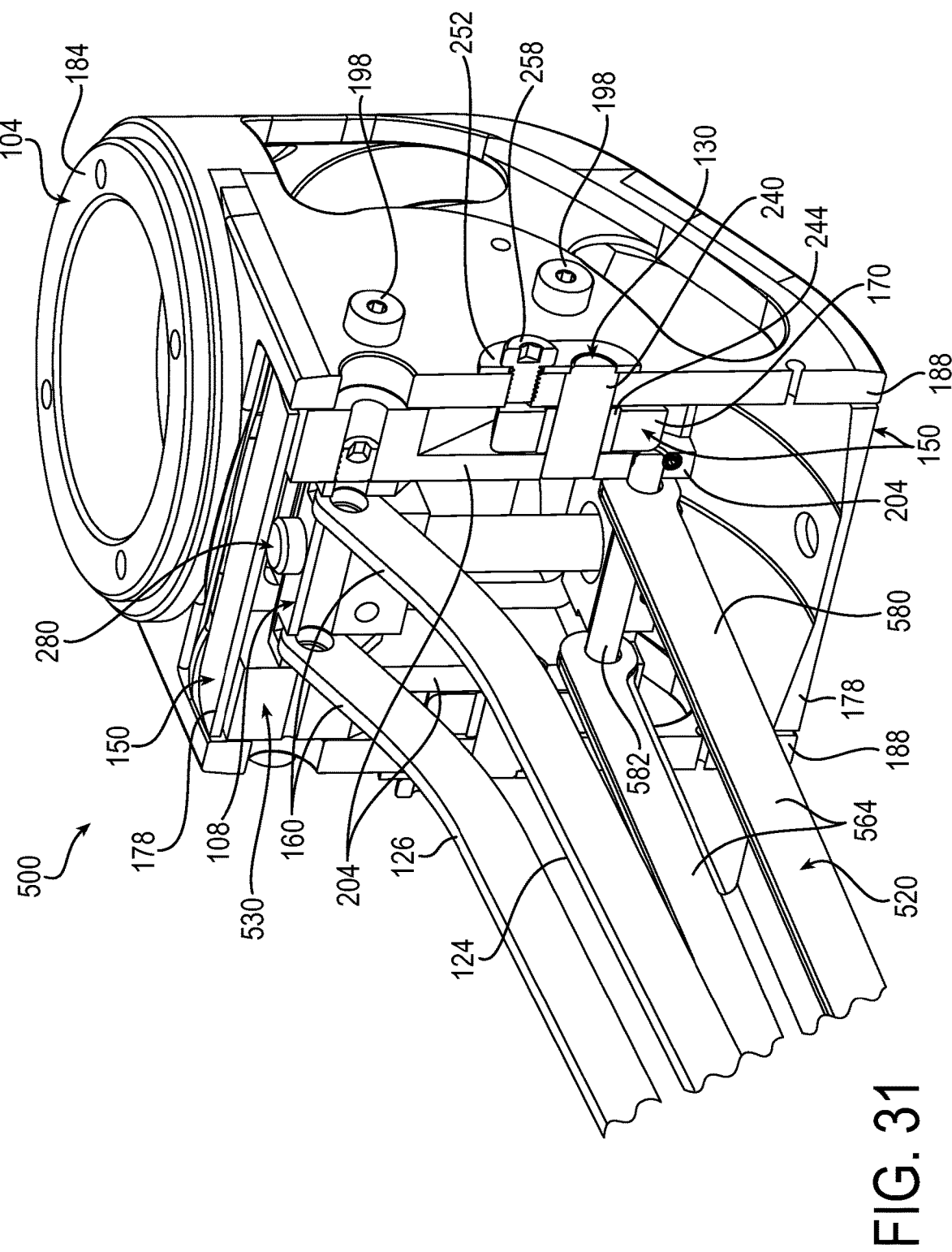

FIG. 31 is a partial cross section perspective view of a proximal end of the FIG. 21 load balancing arm, showing internal components of the load balancing arm.

Figure 32:
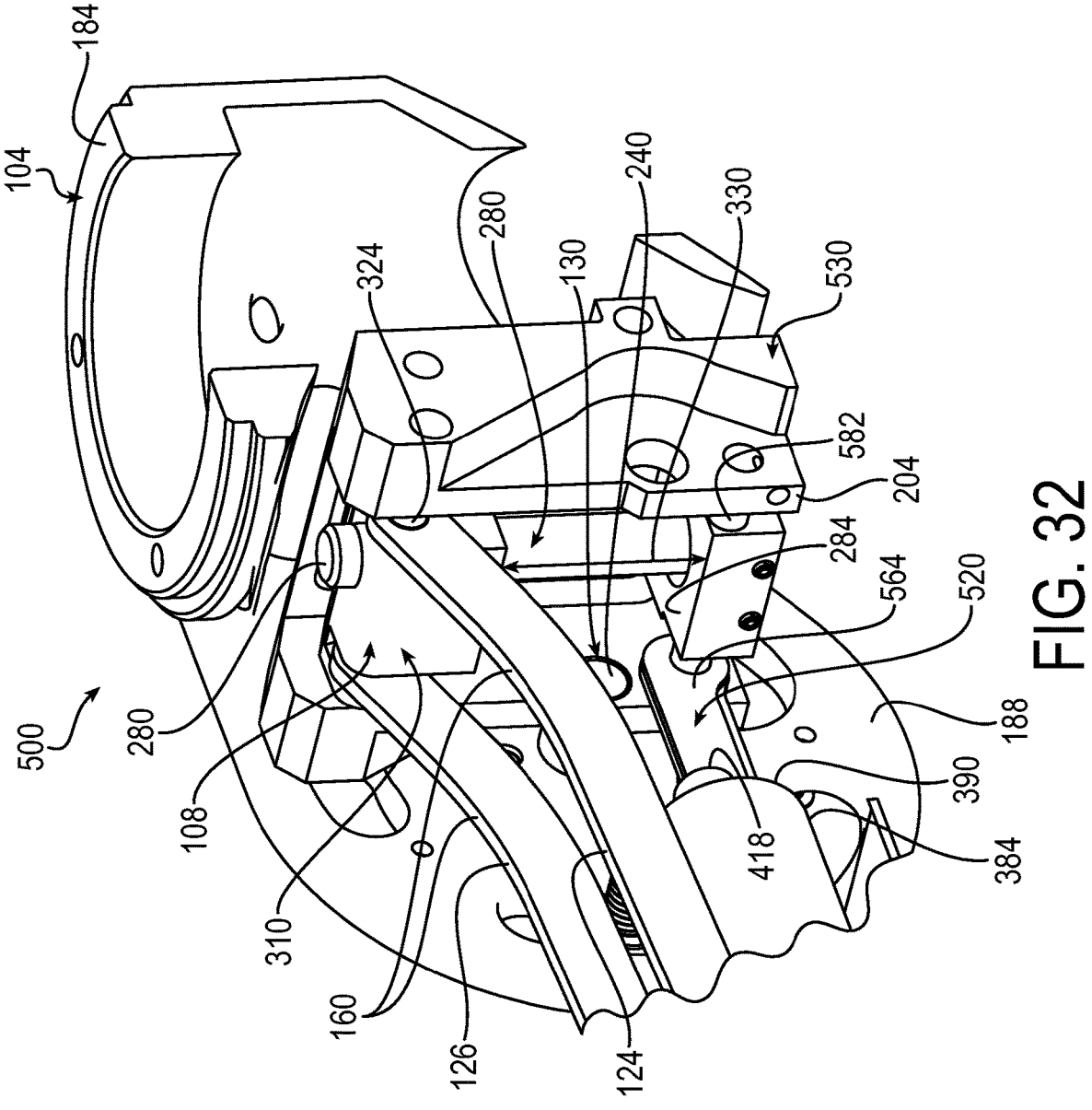

FIG. 32 is a partial cross section perspective view of a proximal end of the FIG. 21 load balancing arm, showing internal components of the load balancing arm.

Figure 33:
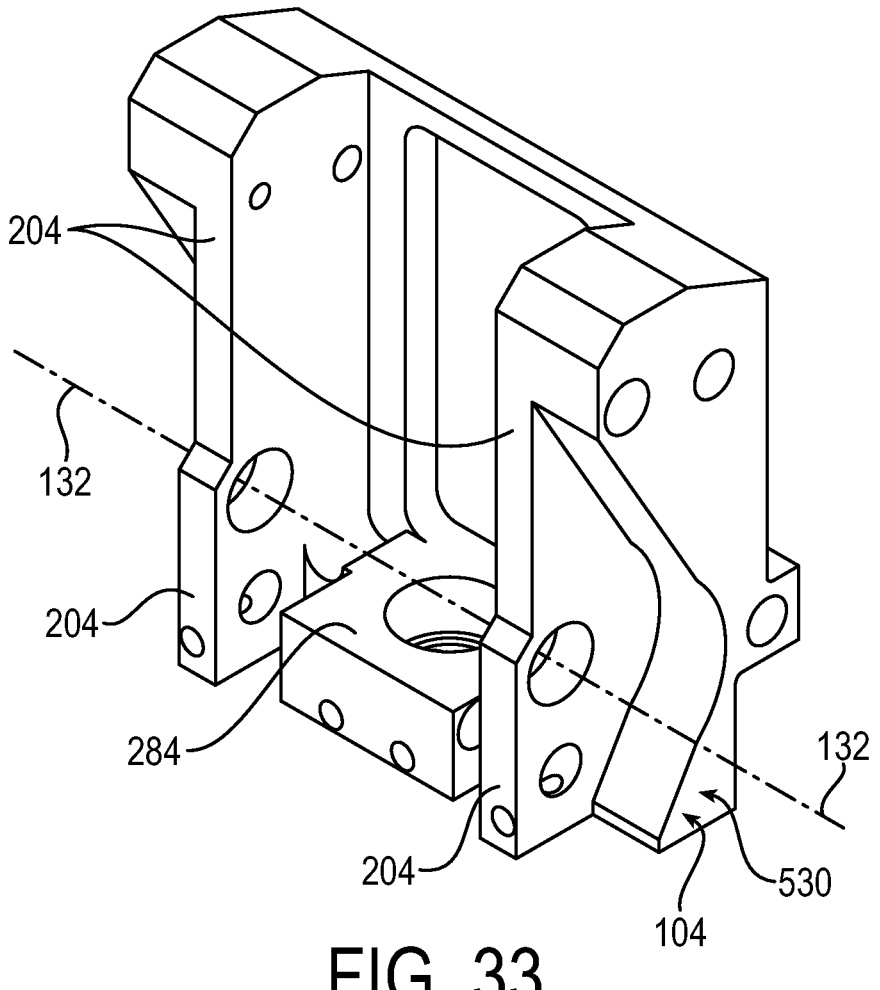

FIG. 33 is a side perspective view of a load adjustment block of a proximal hub of the FIG. 21 load balancing arm.

Figure 34:
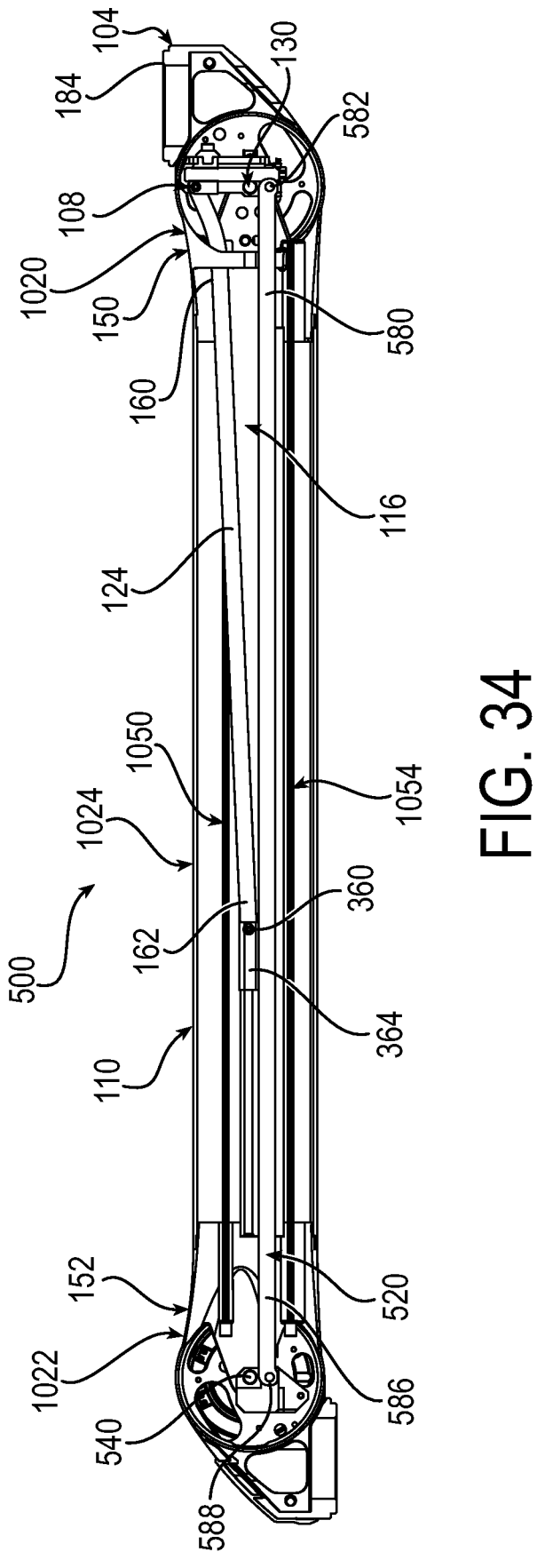

FIG. 34 is a side cross section view of the FIG. 21 load balancing arm in a substantially horizontal position, showing internal components of the load balancing arm.

Figure 35:
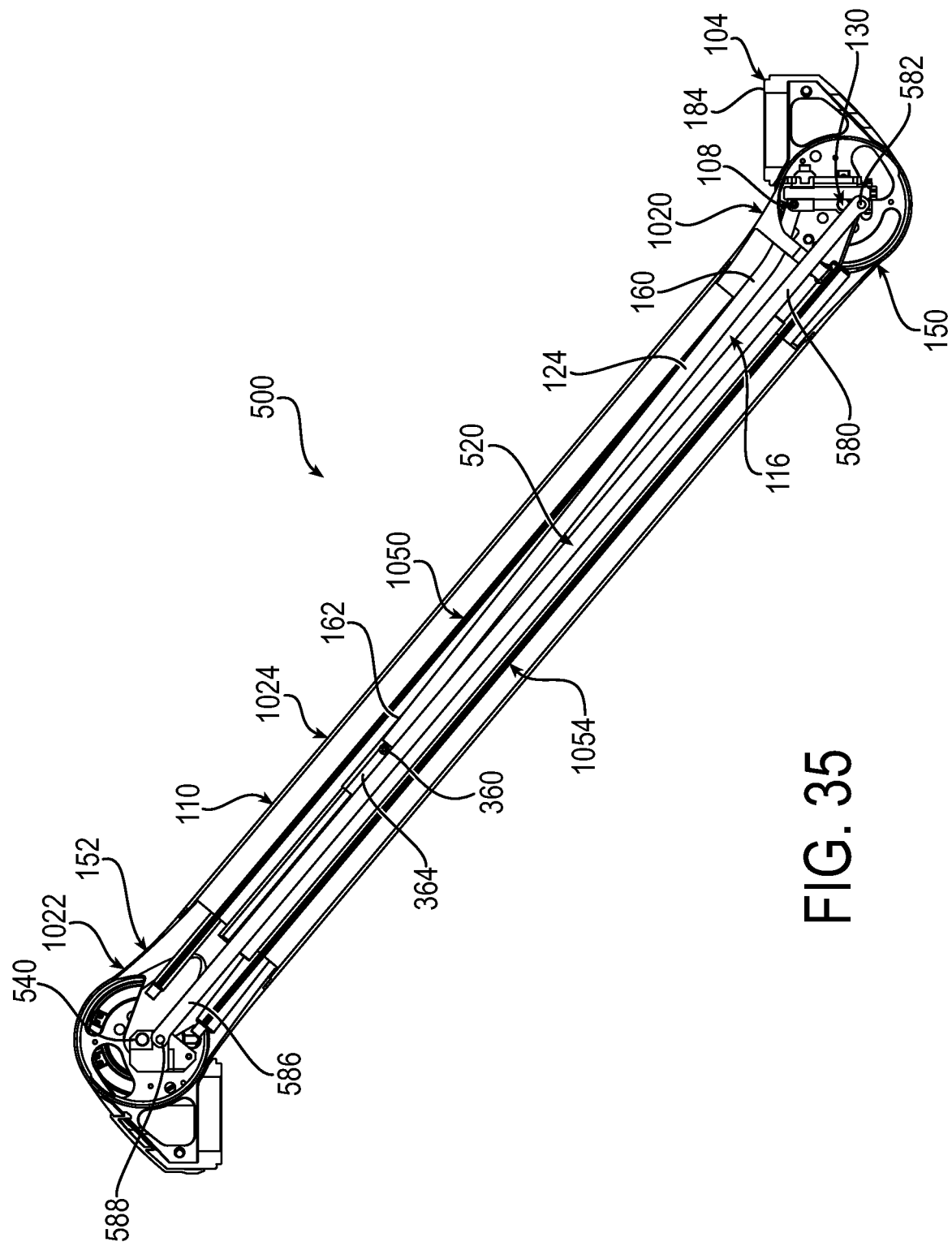

FIG. 35 is a side cross section view of the FIG. 21 load balancing arm in a position upward from horizontal, showing internal components of the load balancing arm.

Figure 36:
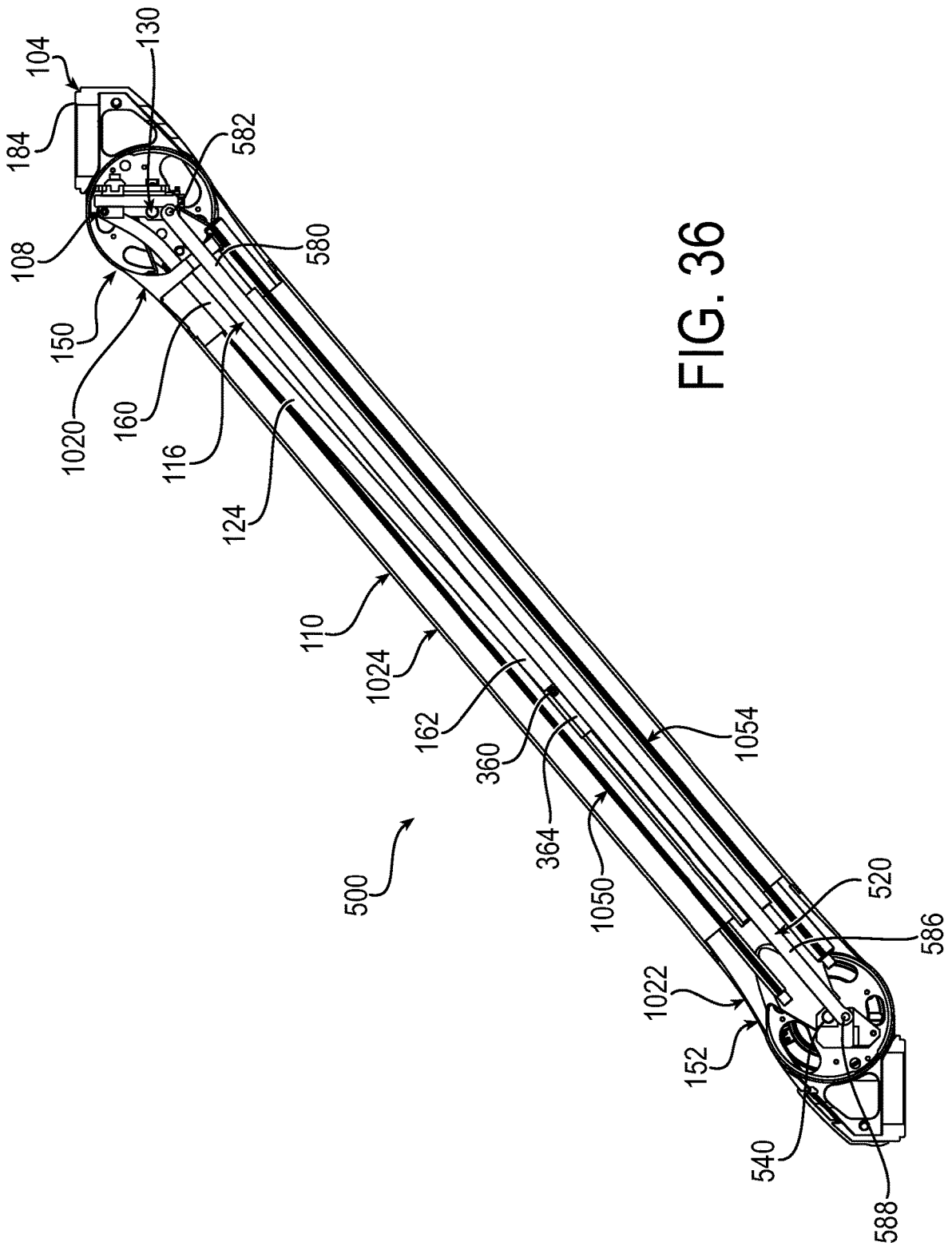

FIG. 36 is a side cross section view of the FIG. 21 load balancing arm in a position downward from horizontal, showing internal components of the load balancing arm.

Figure 37:
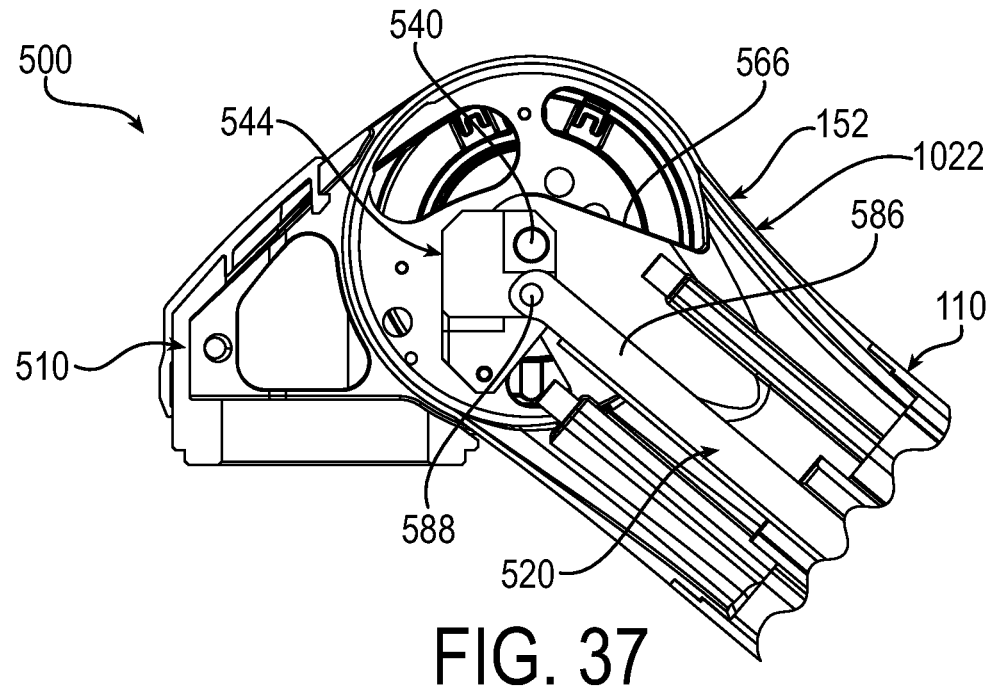

FIG. 37 is a side cross section view of the distal end of the FIG. 21 load balancing arm in a position upward from horizontal, showing internal components of the load balancing arm.

Figure 38:
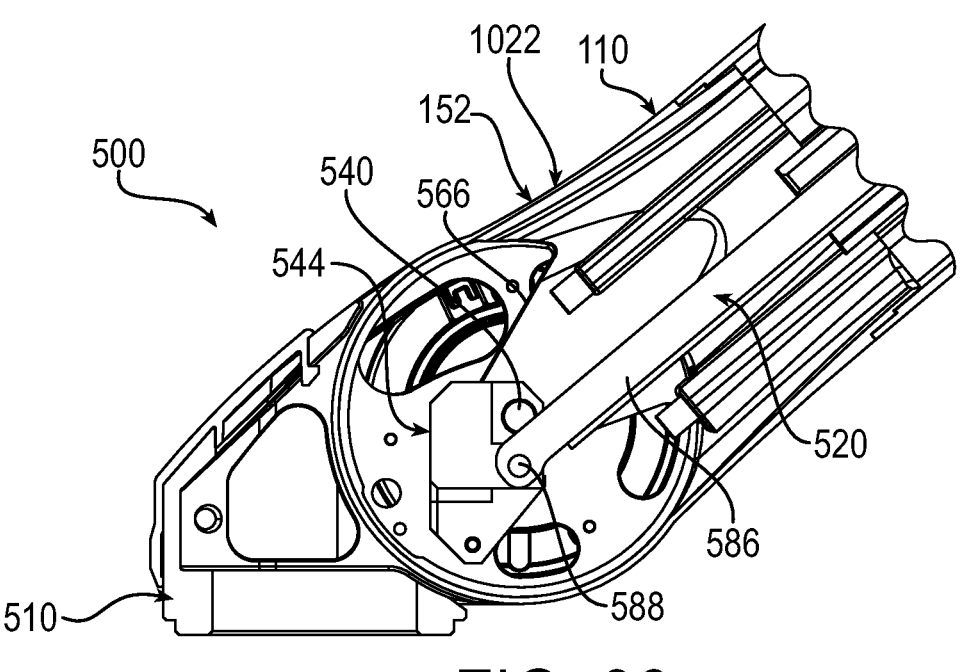

FIG. 38 is a side cross section view of the distal end of the FIG. 21 load balancing arm in a position downward from horizontal, showing internal components of the load balancing arm.

Figure 39:
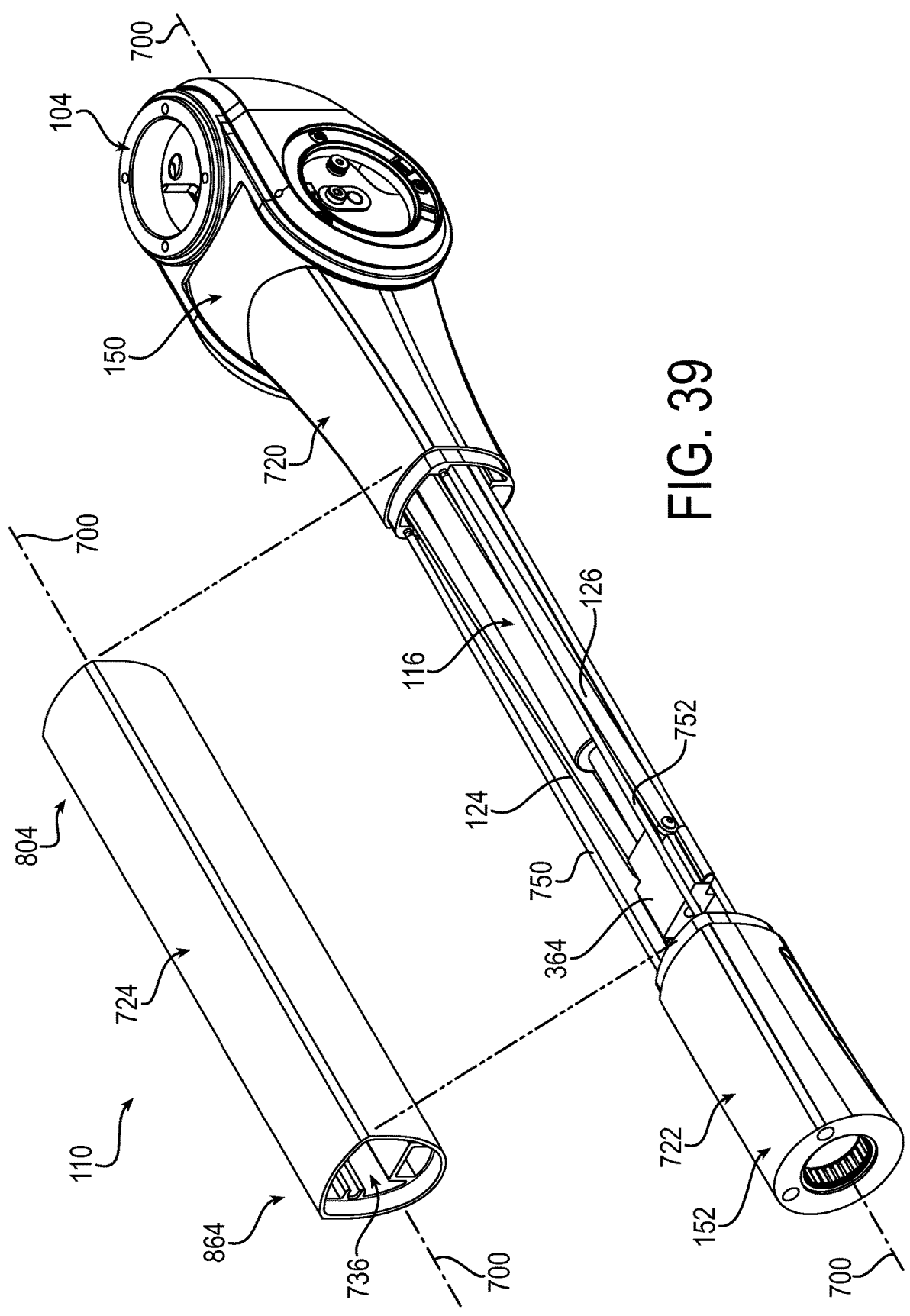

FIG. 39 is a top perspective view of the FIG. 2 load balancing arm, showing in greater detail a support arm thereof in accordance with an embodiment of the invention, with an intermediate beam displaced to show internal components of the support arm.

Figure 40:
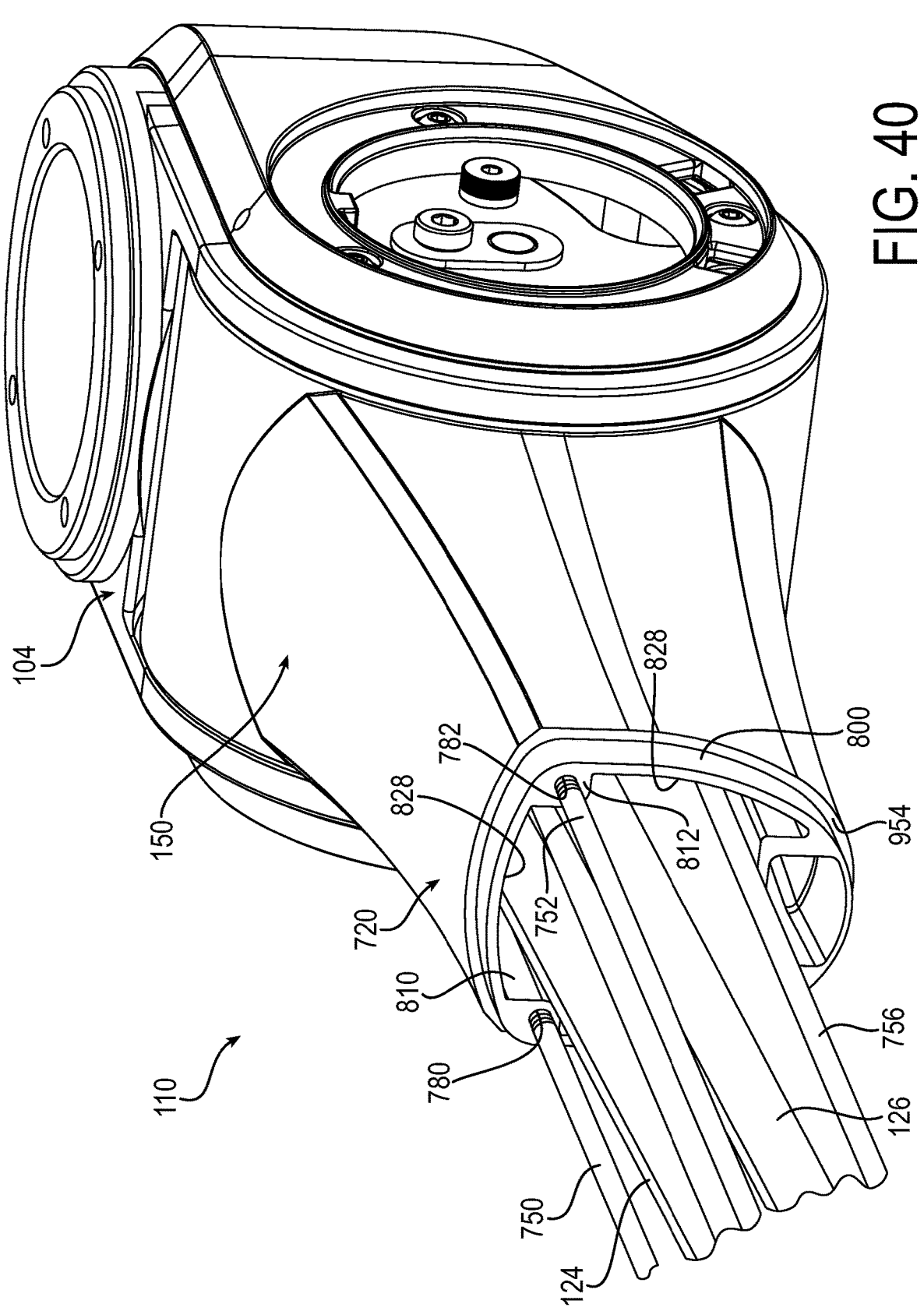

FIG. 40 is a front perspective view of a proximal hub of the FIG. 39 support arm, showing an end wall of the proximal hub, and portions of tension members.

Figure 41:
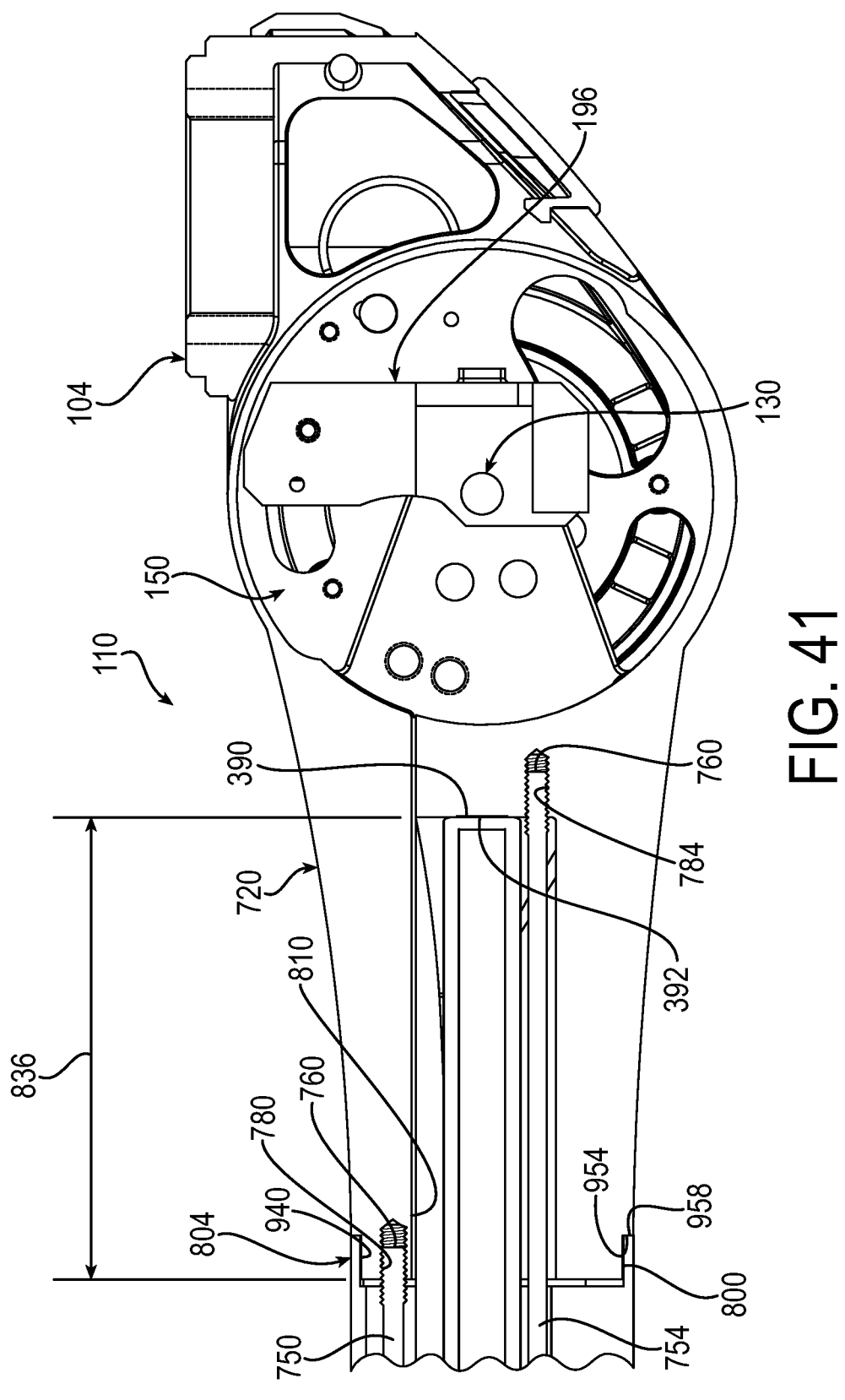

FIG. 41 is a side cross section view of a proximal end of the FIG. 39 support arm, showing a proximal hub of the support arm, and portions of an intermediate beam and tension members.

Figure 42:
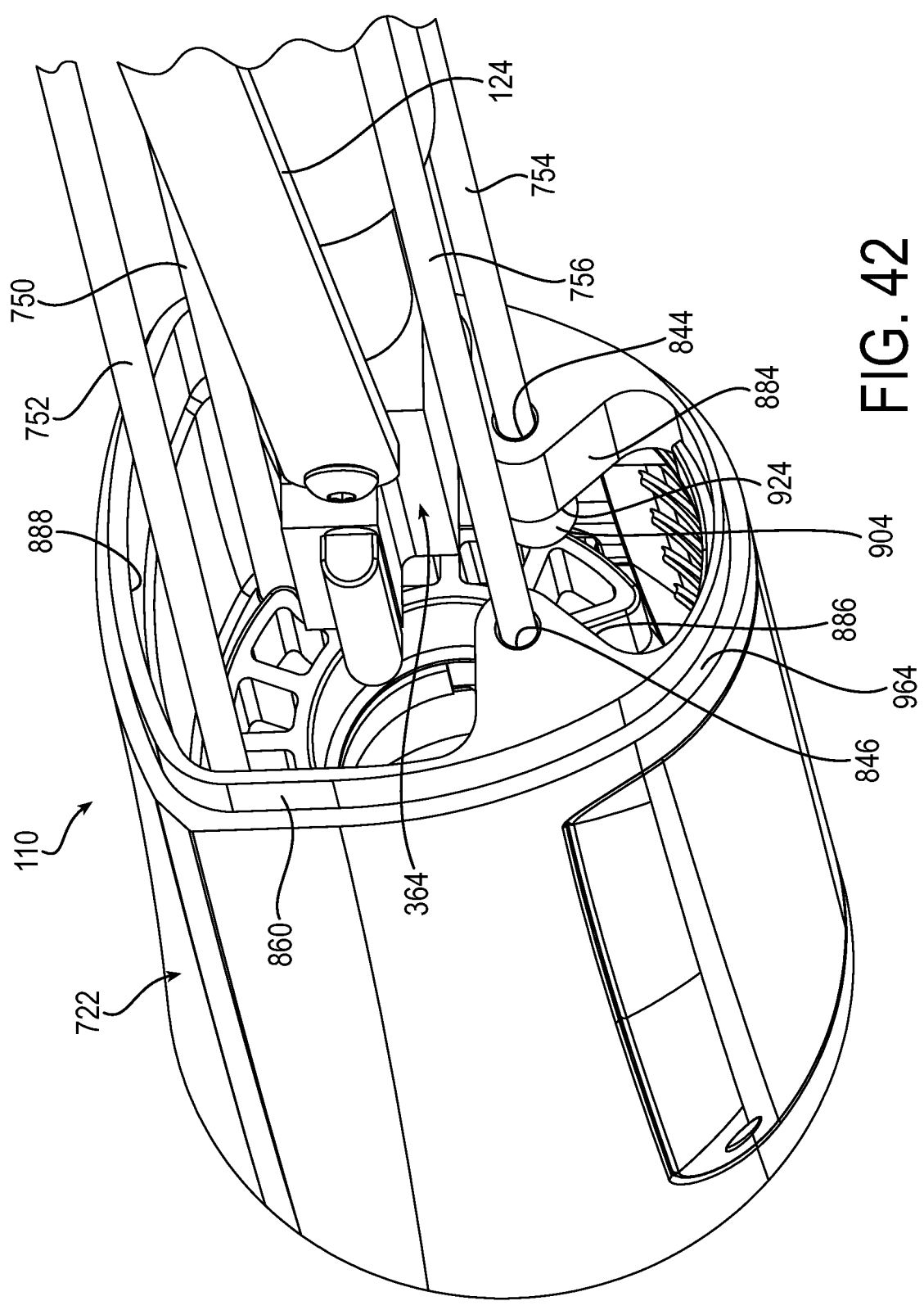

FIG. 42 is a rear perspective view of a distal hub of the FIG. 39 support arm, showing an end wall of the distal hub, and portions of tension members.

Figure 43:
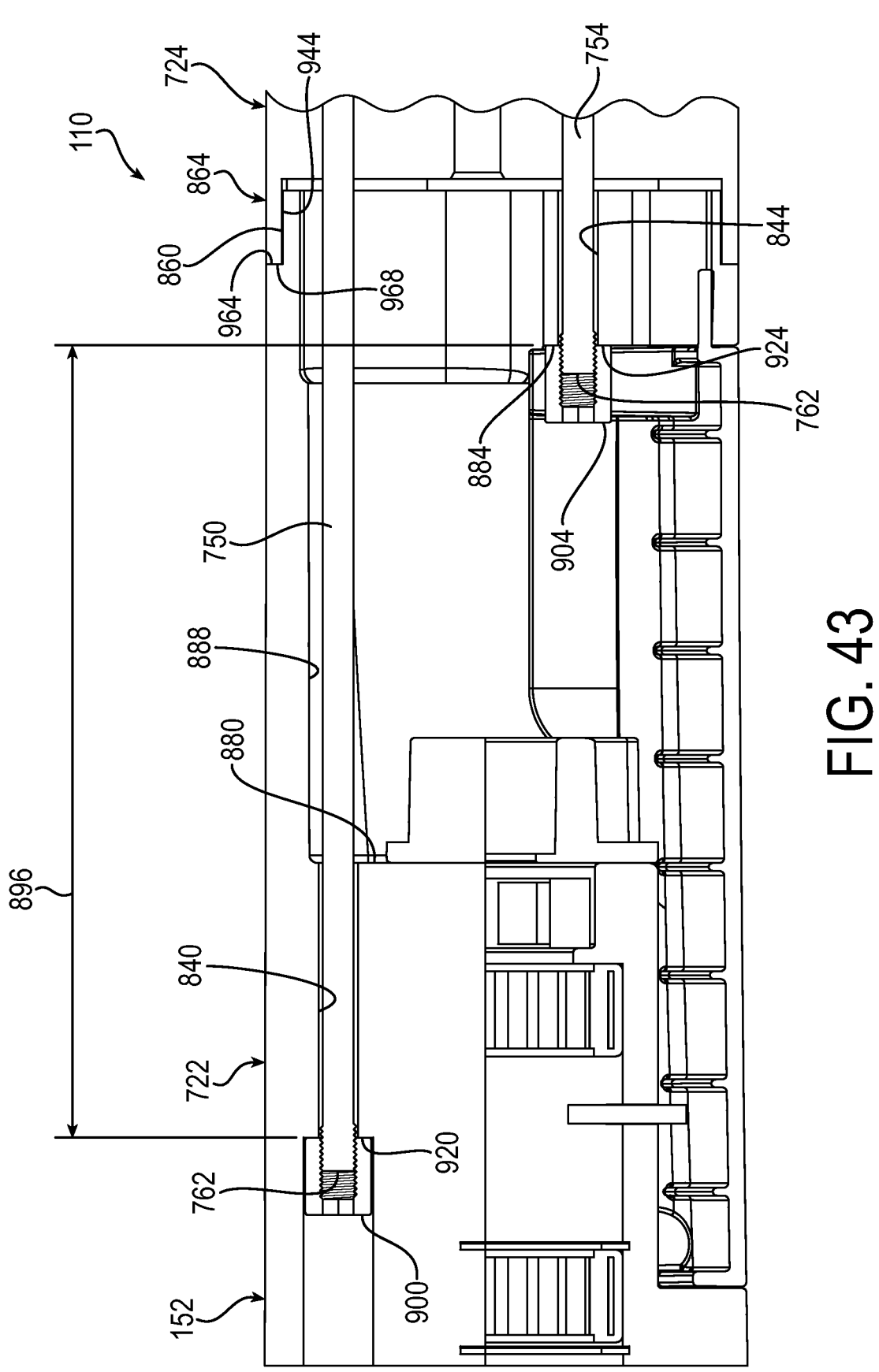

FIG. 43 is a side cross section view of a distal end of the FIG. 39 support arm, showing a distal hub of the support arm, and portions of an intermediate beam and tension members.

Figure 44:
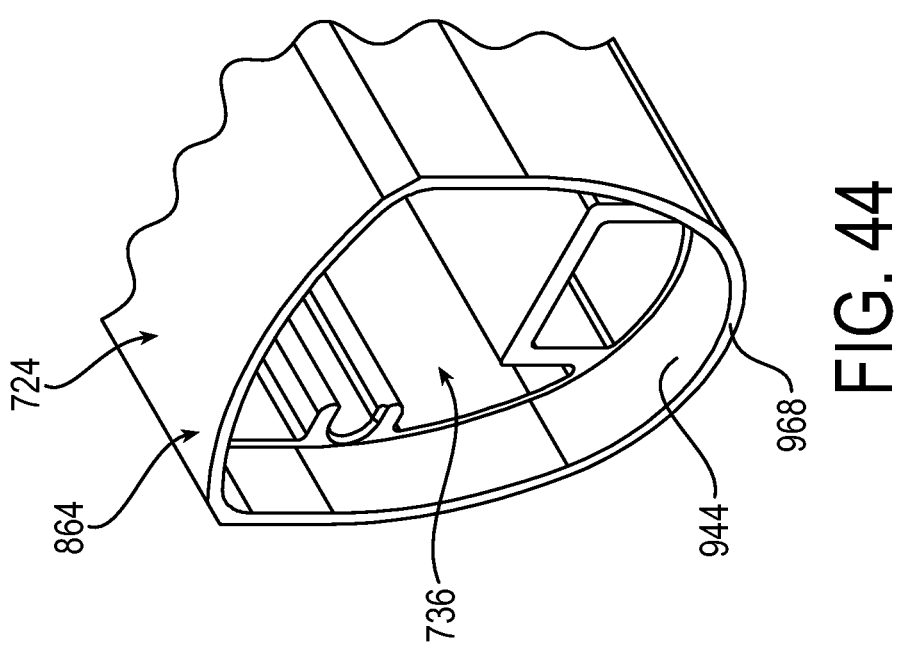

FIG. 44 is a perspective view of a distal end of an intermediate beam of the FIG. 39 support arm.

Figure 45:
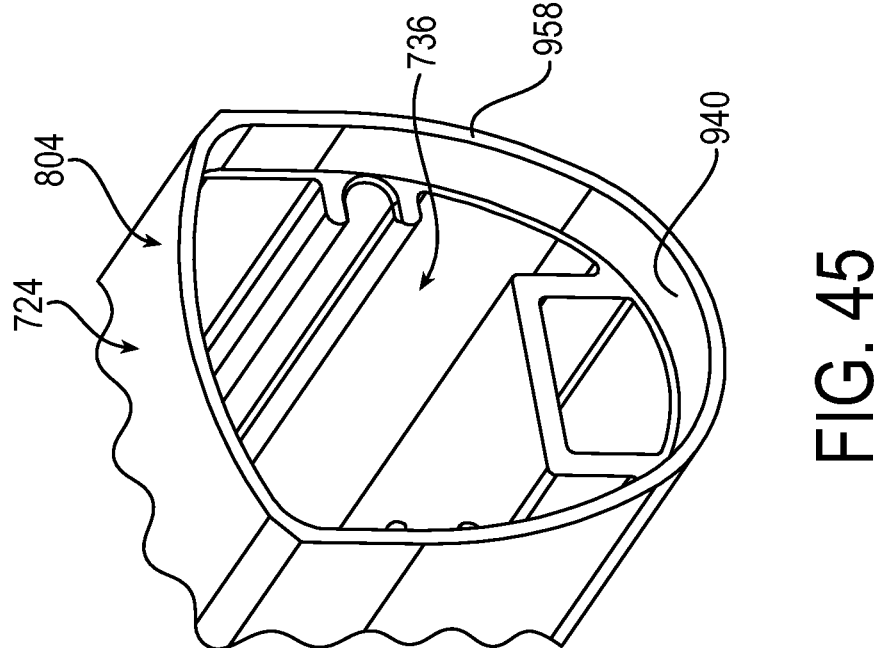

FIG. 45 is a perspective view of a proximal end of an intermediate beam of the FIG. 39 support arm.

Figure 46:
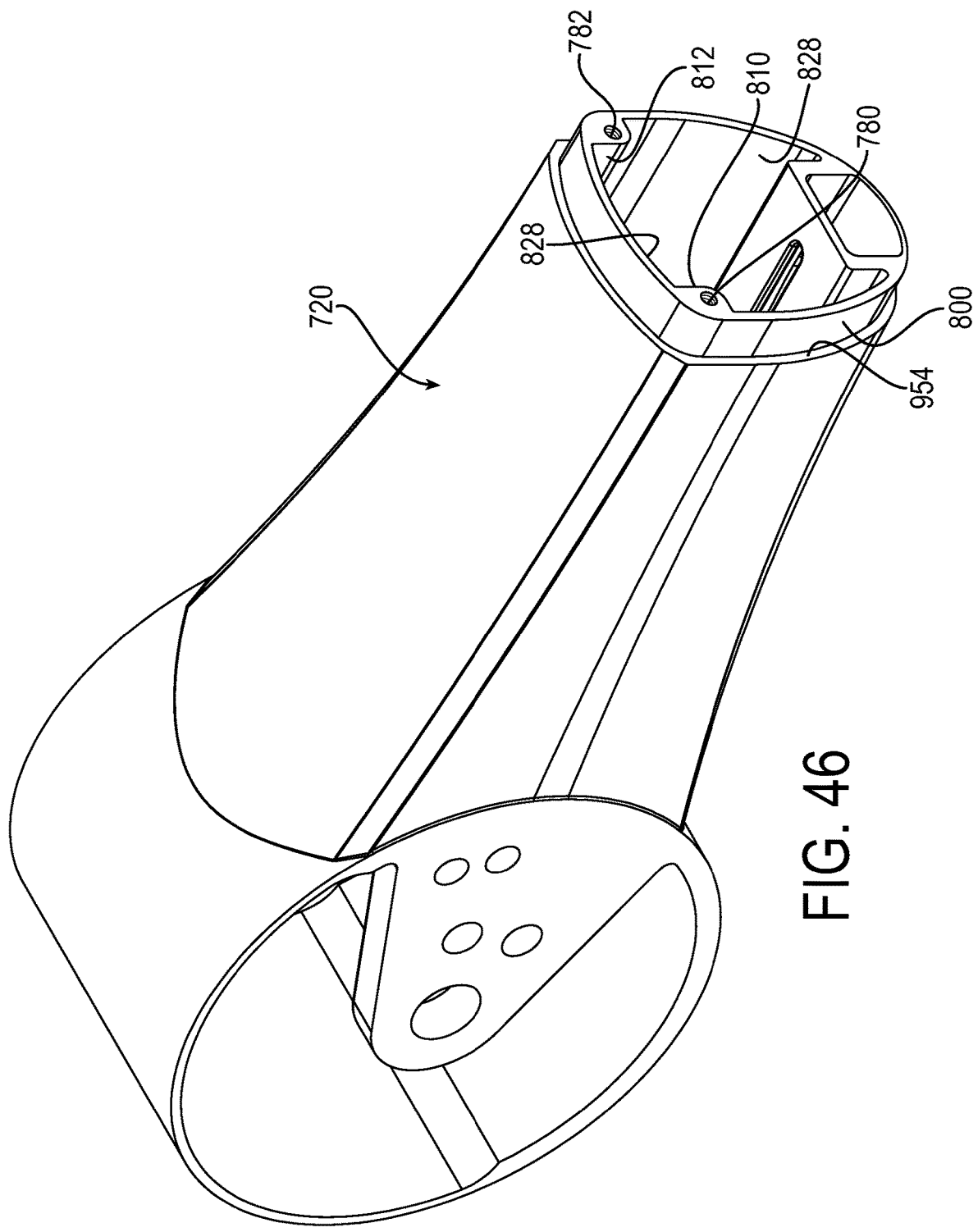

FIG. 46 is a front perspective view of an inner proximal hub of the FIG. 39 support arm, shown in isolation.

Figure 47:
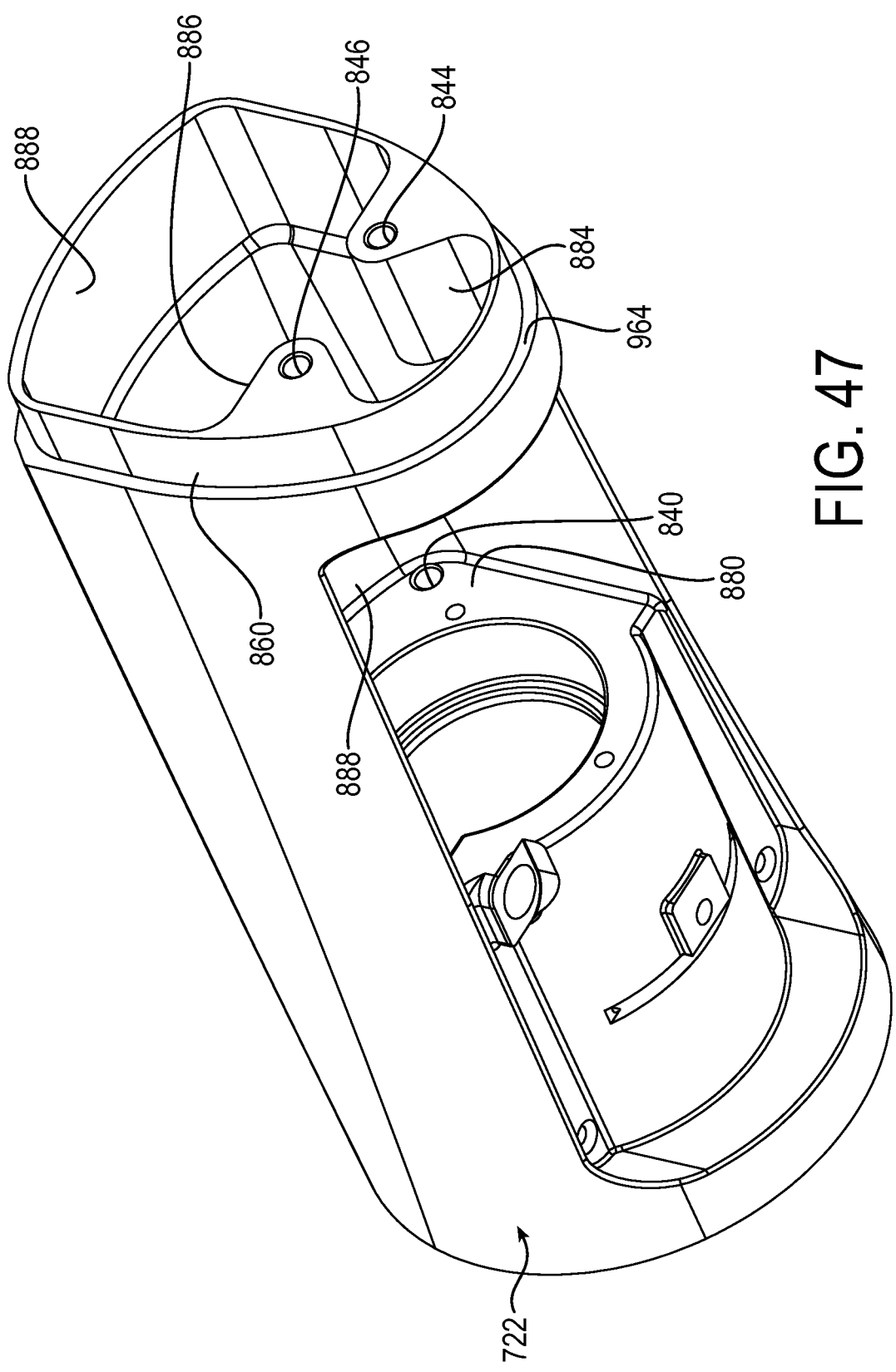

FIG. 47 is a rear perspective view of a distal hub of the FIG. 39 support arm, shown in isolation.

Figure 48:
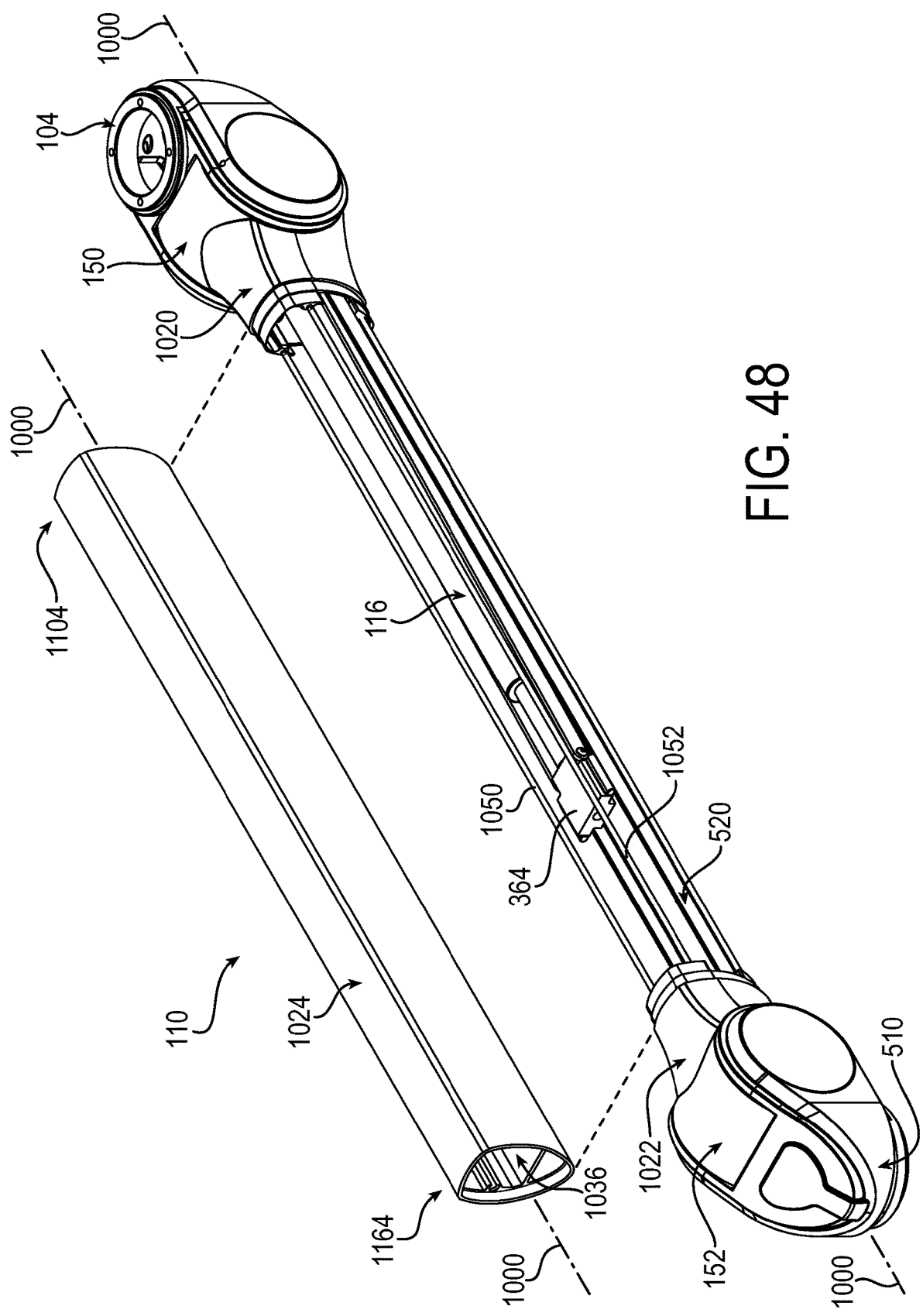

FIG. 48 is a top perspective view of the FIG. 21 load balancing arm, showing in greater detail a support arm thereof in accordance with an embodiment of the invention, with an intermediate beam displaced to show internal components of the support arm.

Figure 49:
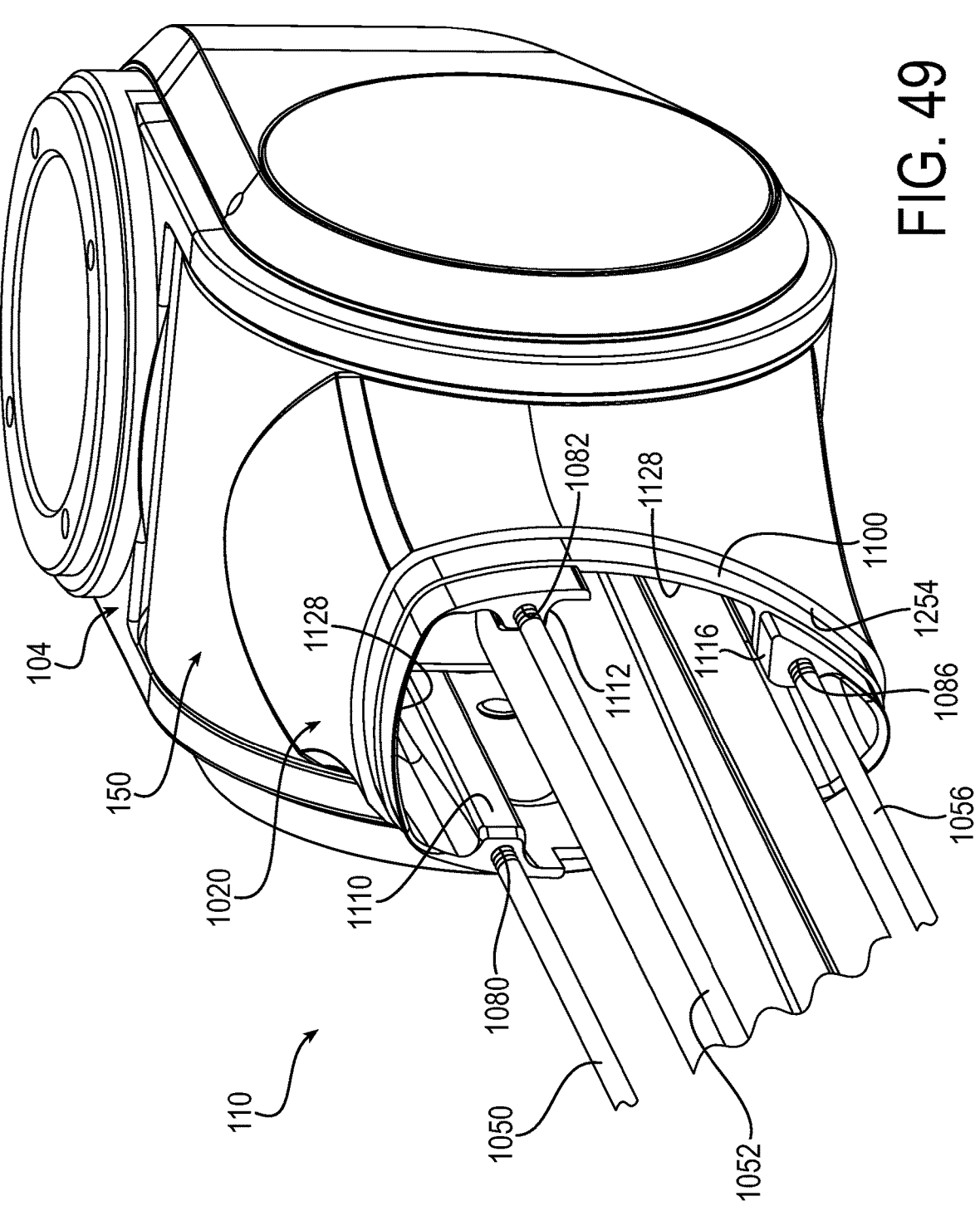

FIG. 49 is a front perspective view of a proximal hub of the FIG. 48 support arm, showing an end wall of the proximal hub, and portions of tension members.

Figure 50:
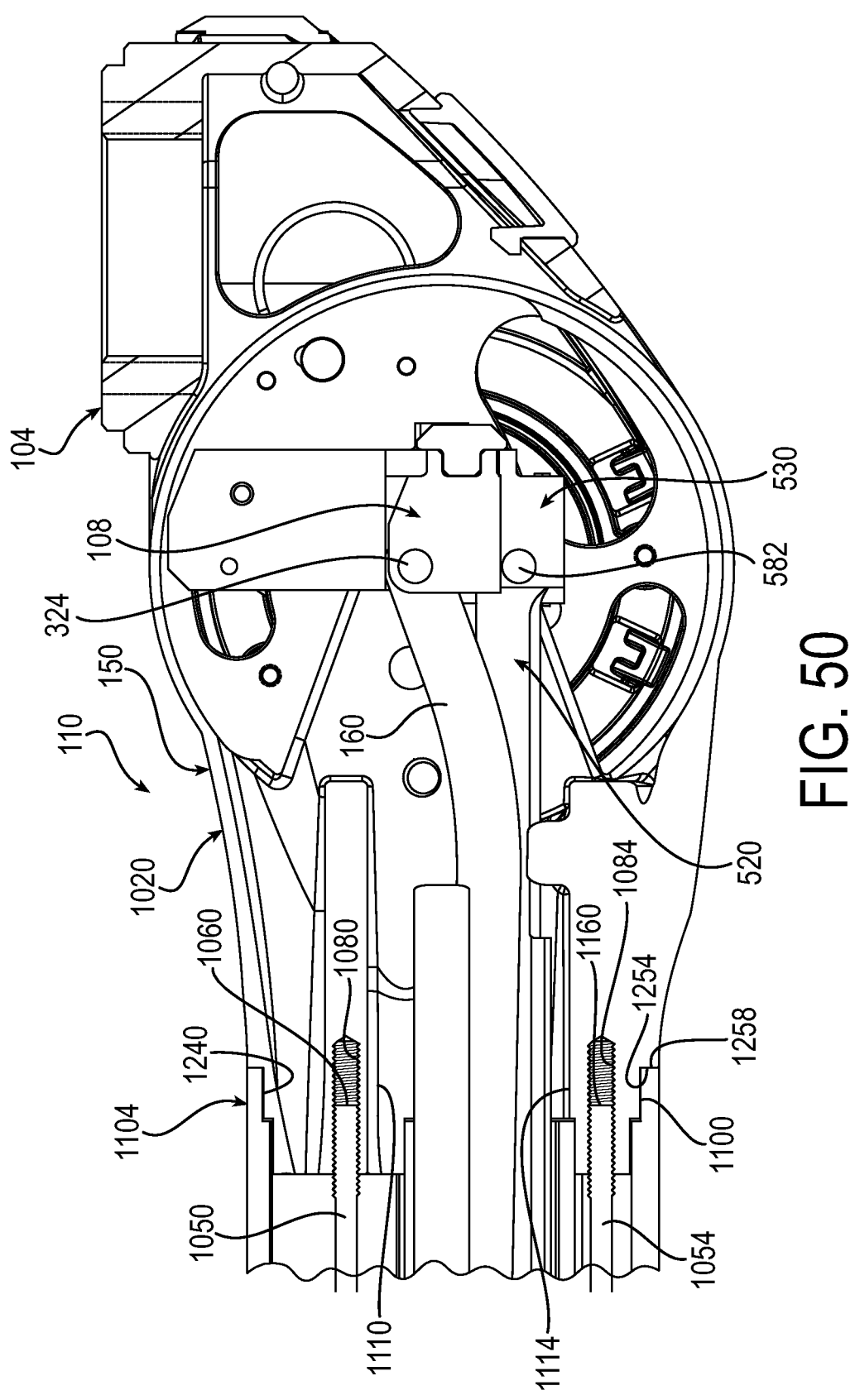

FIG. 50 is a side cross section view of a proximal end of the FIG. 48 support arm, showing a proximal hub of the support arm, and portions of an intermediate beam and tension members.

Figure 51:
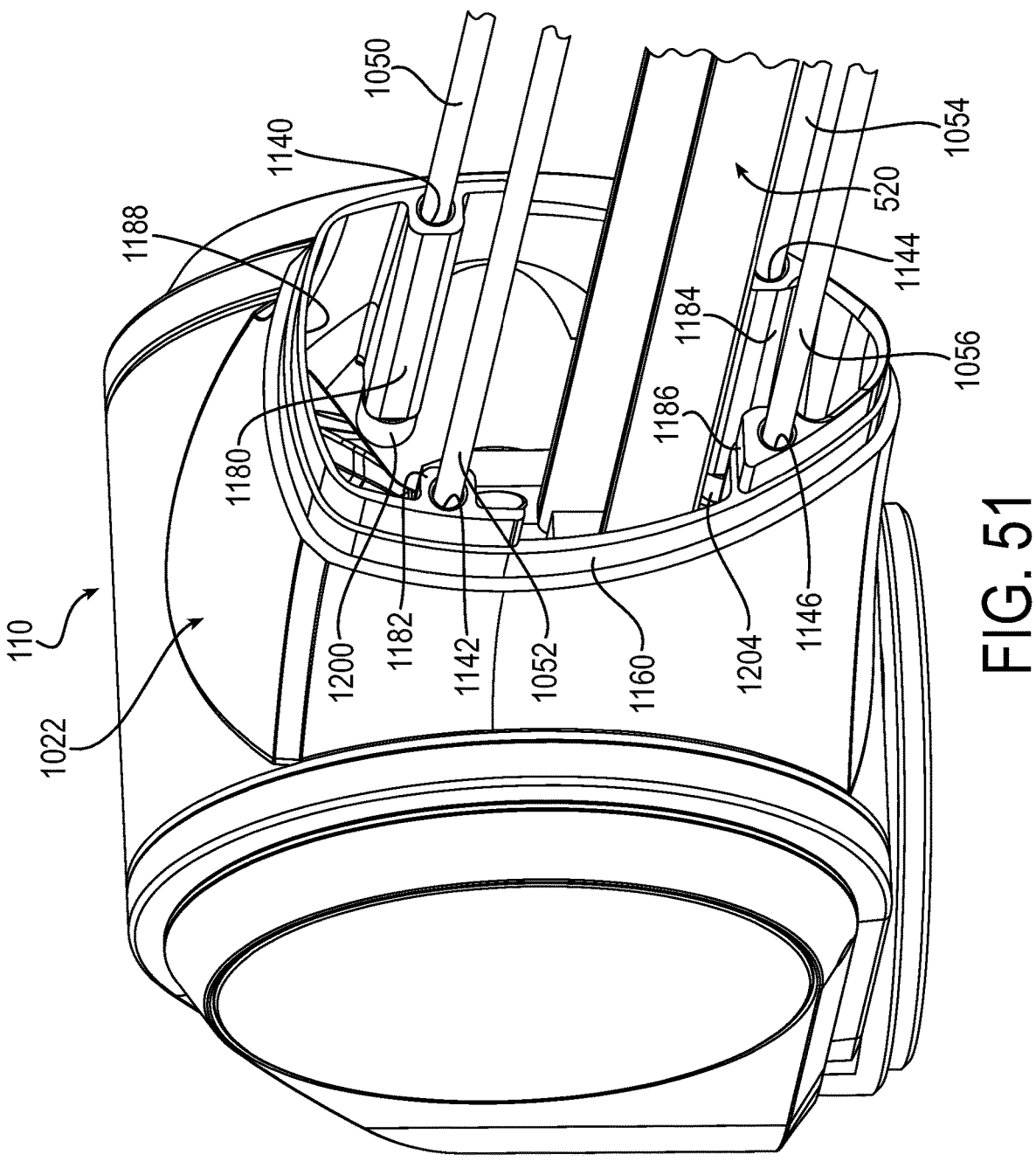

FIG. 51 is a rear perspective view of a distal hub of the FIG. 48 support arm, showing an end wall of the distal hub, and portions of tension members.

Figure 52:
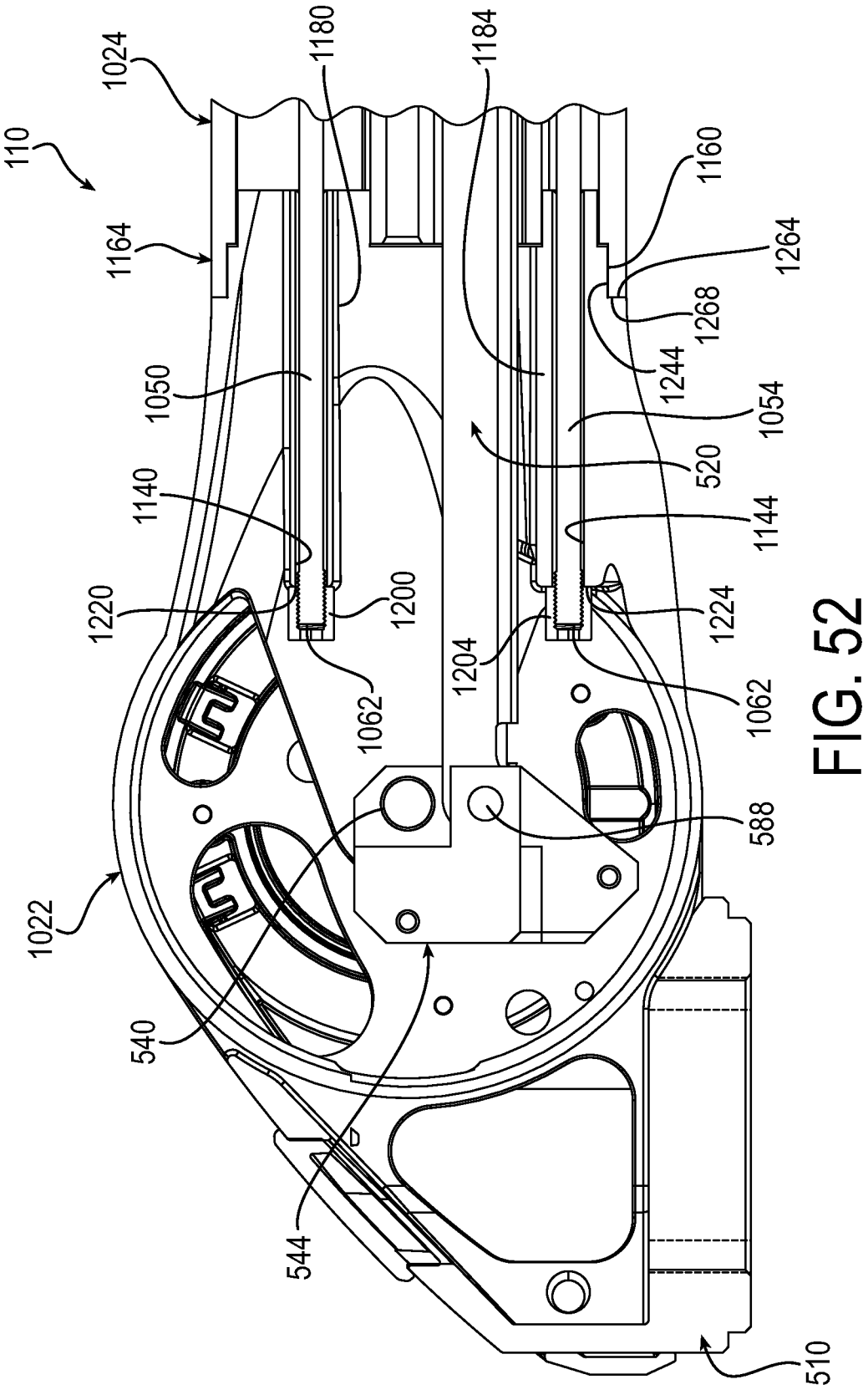

FIG. 52 is a side cross section view of the distal end of the FIG. 48 support arm, showing a distal hub of the support arm, and portions of an intermediate beam and tension members.

Figures 53, 54:
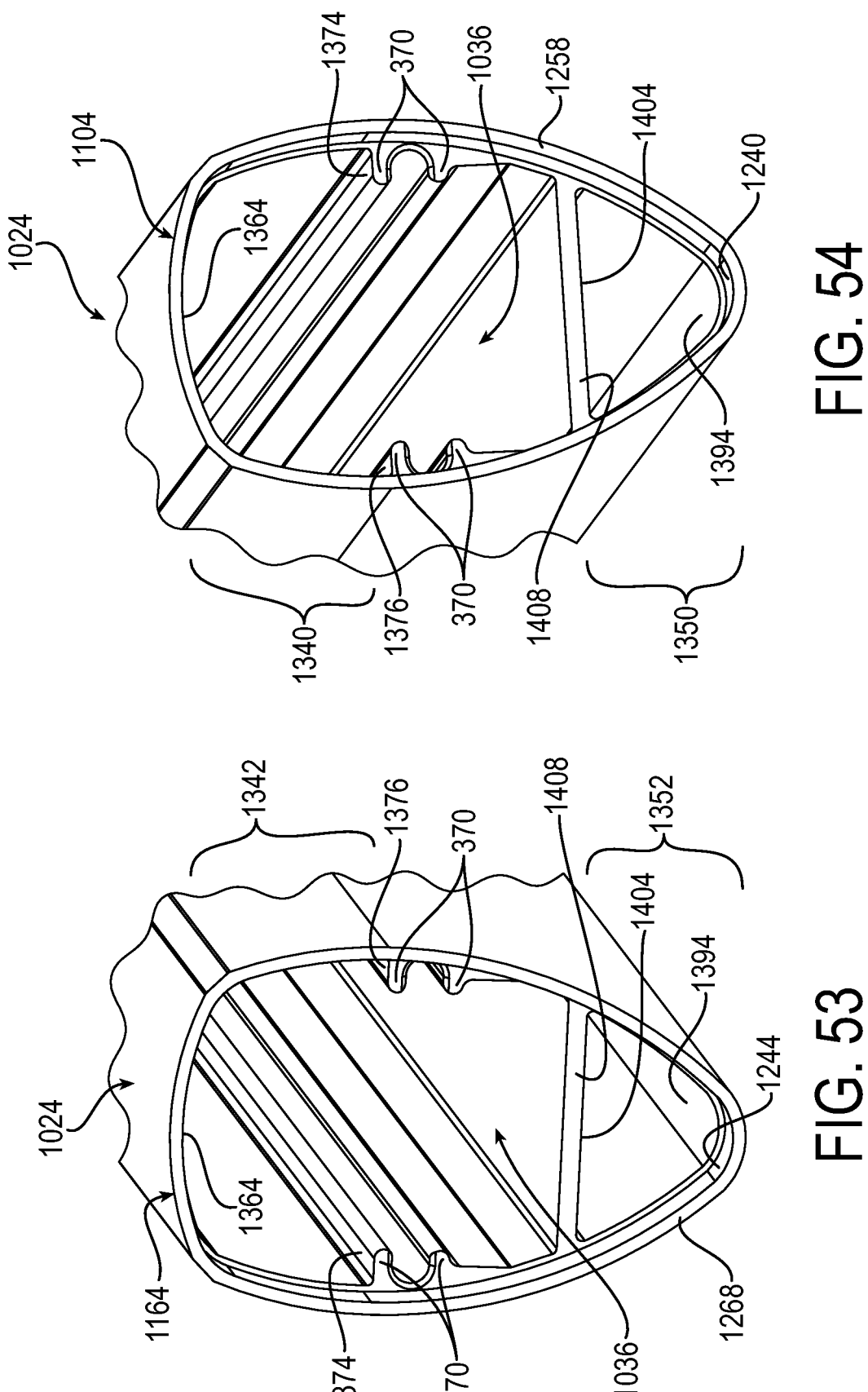

FIG. 53 is a perspective view of a distal end of an intermediate beam of the FIG. 48 support arm.

FIG. 54 is a perspective view of a proximal end of an intermediate beam of the FIG. 48 support arm.

Figure 55:
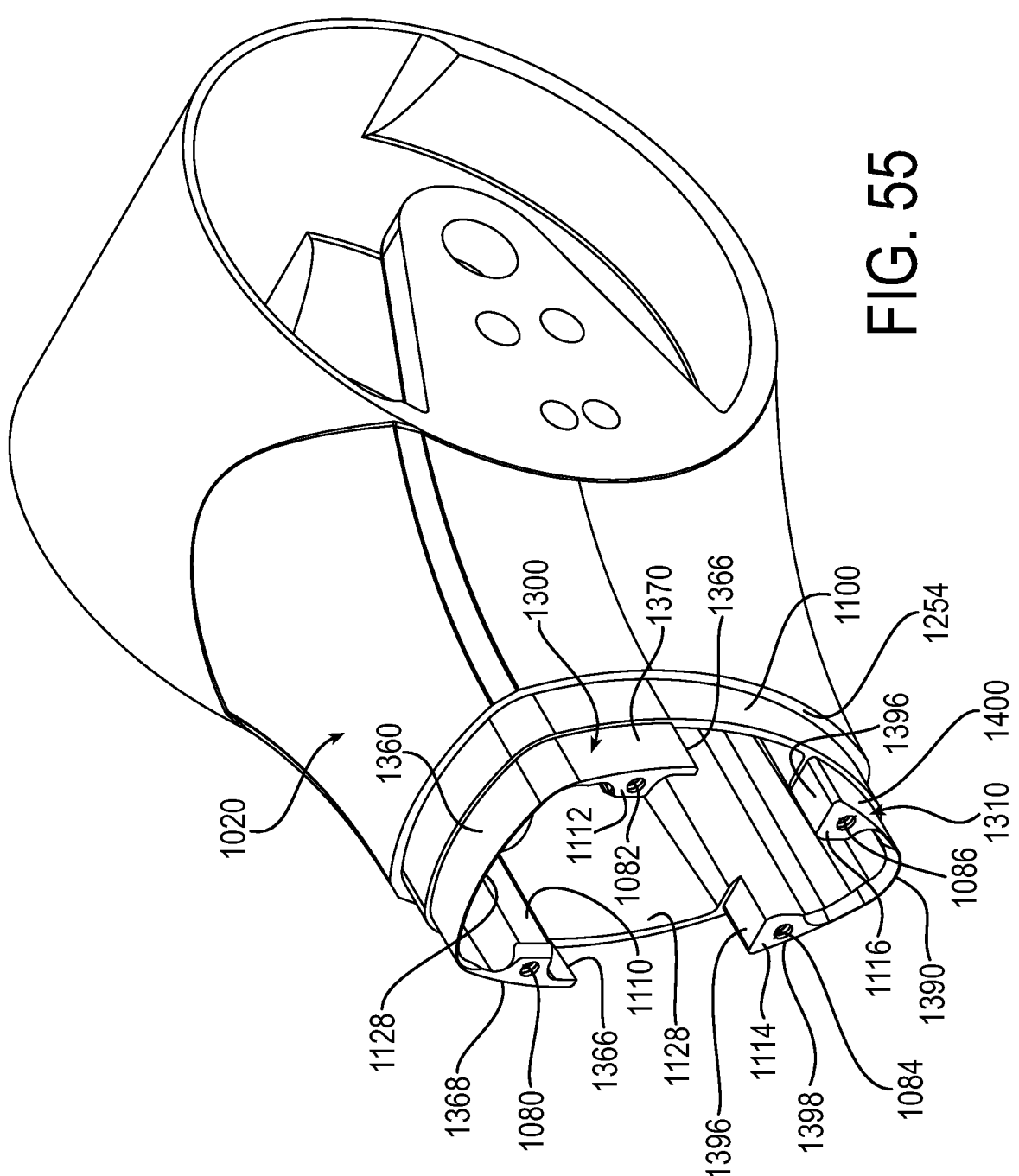

FIG. 55 is a front perspective view of an inner proximal hub of the FIG. 48 support arm, shown in isolation.

Figure 56:
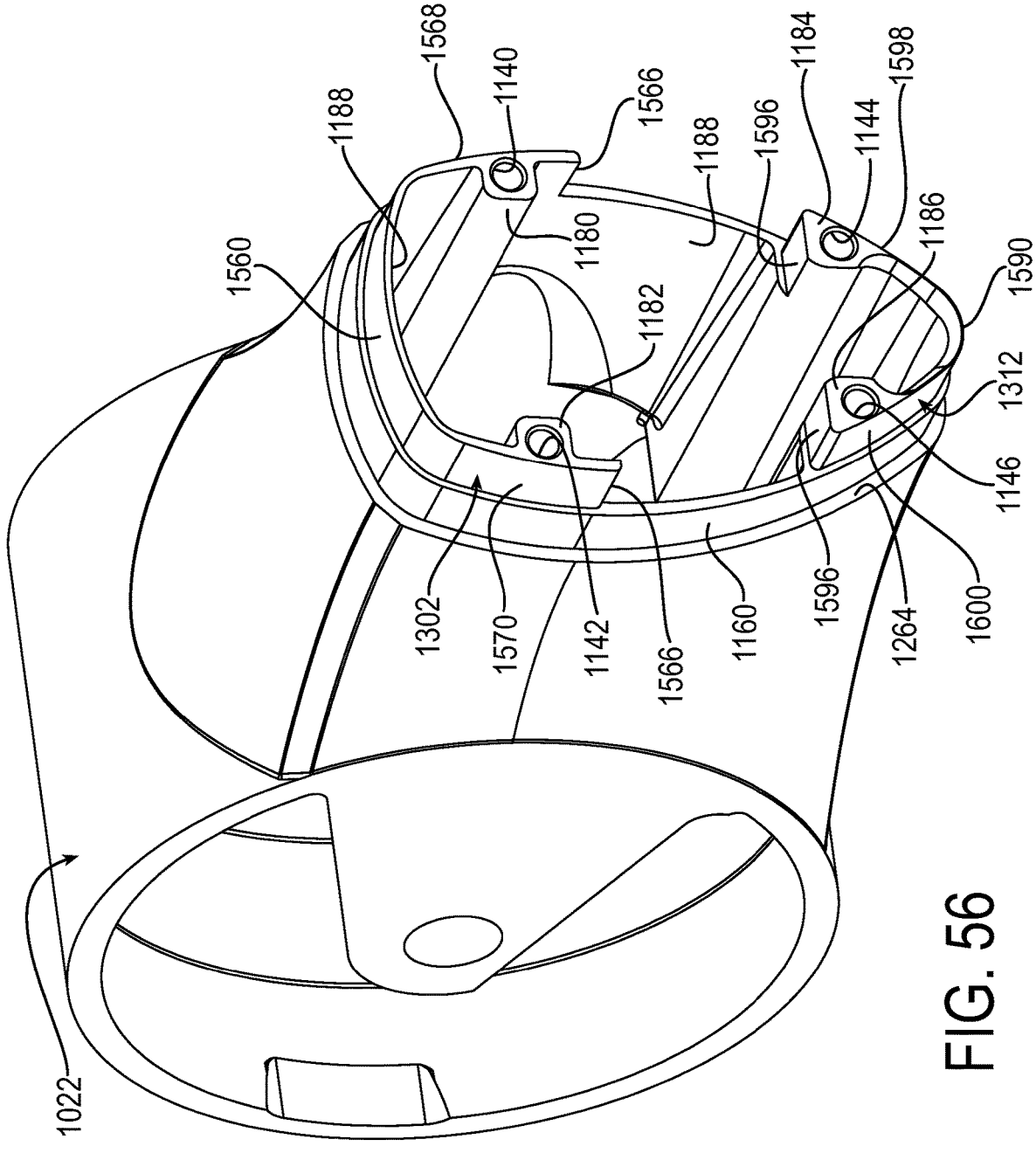

FIG. 56 is a rear perspective view of an inner distal hub of the FIG. 48 support arm, shown in isolation.

FIG. 57 shows a flowchart of a method of assembling a support arm of a medical device support system in accordance with an embodiment of the invention.

DETAILED DESCRIPTION

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates.

Figure 1:
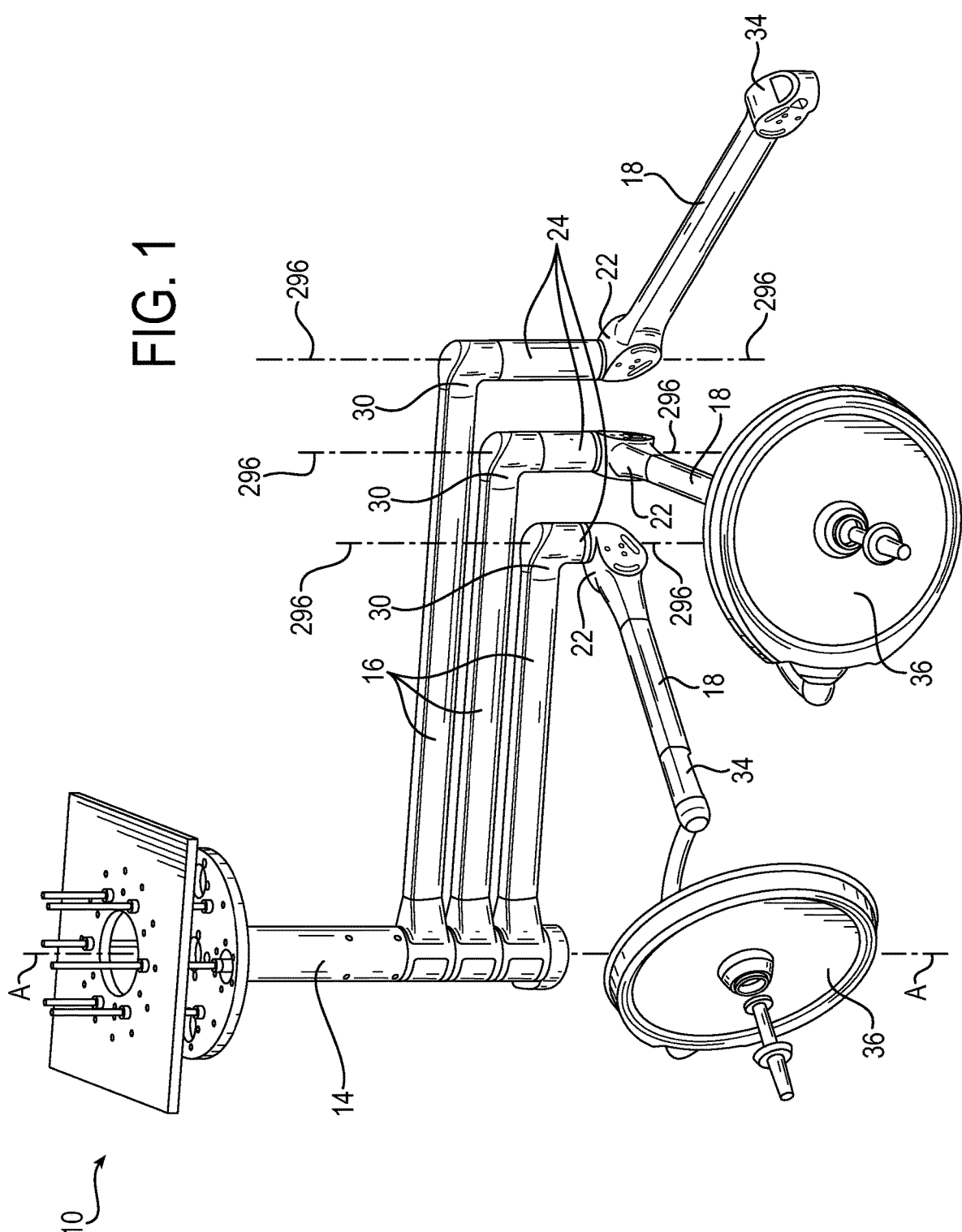
FIG. 1 is a perspective view of a medical device support system in accordance with an embodiment of the invention.

FIG. 1 shows a medical device support system 10 in accordance with an embodiment of the invention. The medical device support system 10 includes a central shaft or support column 14 that is suspended from the ceiling, and three generally horizontal extension arms 16 mounted to the shaft 14 for rotational movement about the shaft 14. The central shaft 14 could be mounted to a wall or stand rather than the ceiling. Three load balancing arms 18, which are also referred to as counterbalancing arms, are mounted to the respective extension arms 16. The extension arms 16 and load balancing arms 18 each include a support arm structure or housing, or more generally a support arm. In the FIG. 1 embodiment, a proximal hub 22 of the load balancing arm 18 includes a support structure 24, for example the illustrative drop tube 24, that is rotatably connectable to a receptacle at the distal end 30 of the extension arm 16. The distal end of each load balancing arm 18 is configured with a suitable support hub 34 to support a medical device load 36. The medical device load 36 may include a surgical light as shown, or a supply console, a patient monitor, a camera detector head, a medical instrument, a ventilator system, a suction device, among others. A control console, if provided, may provide controls for navigation of a medical instrument that is either coupled to or remote from the load balancing arm 18. The load balancing arm 18 enables positioning of the medical device 36 to a proper orientation relative to for example a patient operating table and healthcare professionals in the operating room.

Figure 3:
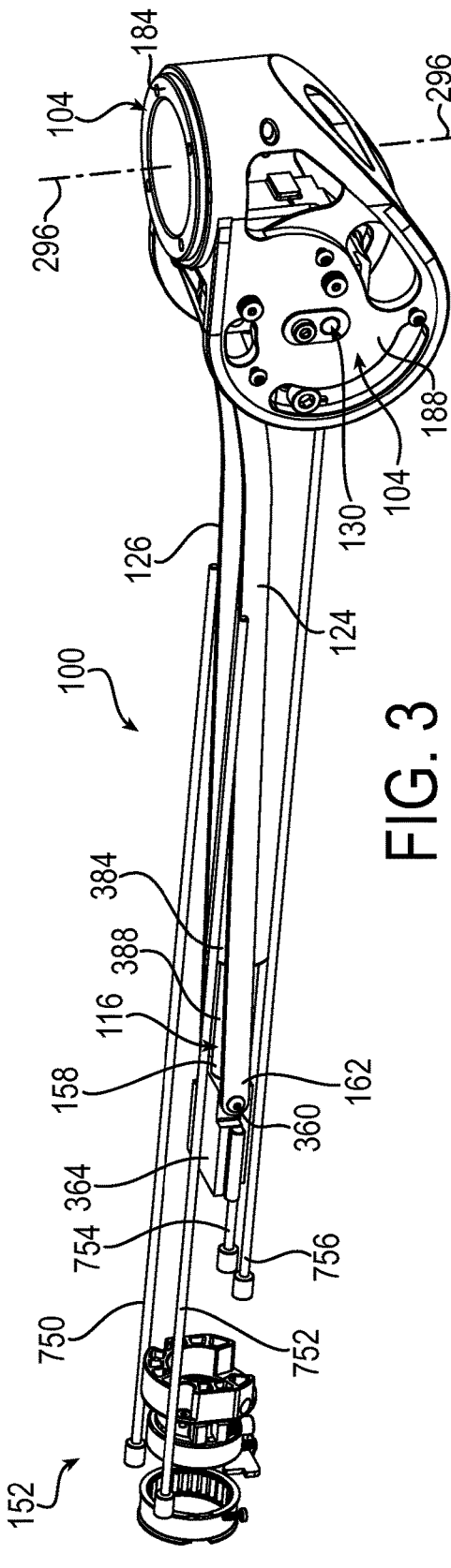
FIG. 3 is a view similar to FIG. 2 with a support arm structure removed to show internal components of the load balancing arm.

Turning now to FIGS. 2-20, there is shown a load balancing arm 100 of the medical device support system 10 in accordance with an embodiment of the invention. The load balancing arm 100 includes a proximal hub 104, an adjustable bearing element 108, a support arm 110, a spring 116, and one or more links, two such links 124, 126 in the illustrative embodiment, as shown in FIGS. 3 and 12. The proximal hub 104 may include a support structure 24 such as the drop tube 24 (see FIG. 1). The proximal hub 104 includes a main bearing element 130 that defines a main pivot axis 132. The adjustable bearing element 108 defines an adjustable pivot axis 142 that is adjustable relative to the main pivot axis 132. The support arm 110 has a proximal end 150 and a distal end 152. The distal end 152 is configured to support a medical device load 36 (see FIG. 1) and the proximal end 150 is pivotably mounted to the main bearing element 130 for pivotable movement about the main pivot axis 132. Pivotable movement about the main pivot axis 132 raises and lowers the height of the medical device load 36 at the distal end 152.

The spring 116 extends within a cavity 154 of the support arm 110 and is mounted to exert a biasing force between the main pivot axis 132 and a distal end 158 of the spring 116. The links 124, 126 each have a proximal end 160 and a distal end 162. The proximal end 160 is pivotably mounted to the adjustable bearing element 108 for pivotable movement about the adjustable pivot axis 142. The distal ends 162 of the links 124, 126 are pivotably mounted to the distal end 158 of the spring 116 such that the biasing force exerted by the spring 116 is transmitted through the links 124, 126 to the adjustable bearing element 108 thereby to generate a moment about the main pivot axis 132 of the proximal hub 104 that counters a moment generated by the medical device load 36 at the distal end 152 of the support arm 110, thereby balancing the medical device load 36.

Thus, in the load balancing arm 100 according to the present embodiment, the links 124, 126 connect at their proximal ends 160 to an adjustment bearing element 108 and at their distal ends 162 to the distal end 158 of the spring 116. As will be described in greater detail below, the attachment at the distal end 158 of the spring 116 allows for a relatively longer link than if connected to the proximal end of the spring 116. The inventors have found that this allows for a better force transmission and less spring travel resulting in a more balanced load balancing arm 100 throughout the pivotable range of travel of the arm 100.

Figure 5:
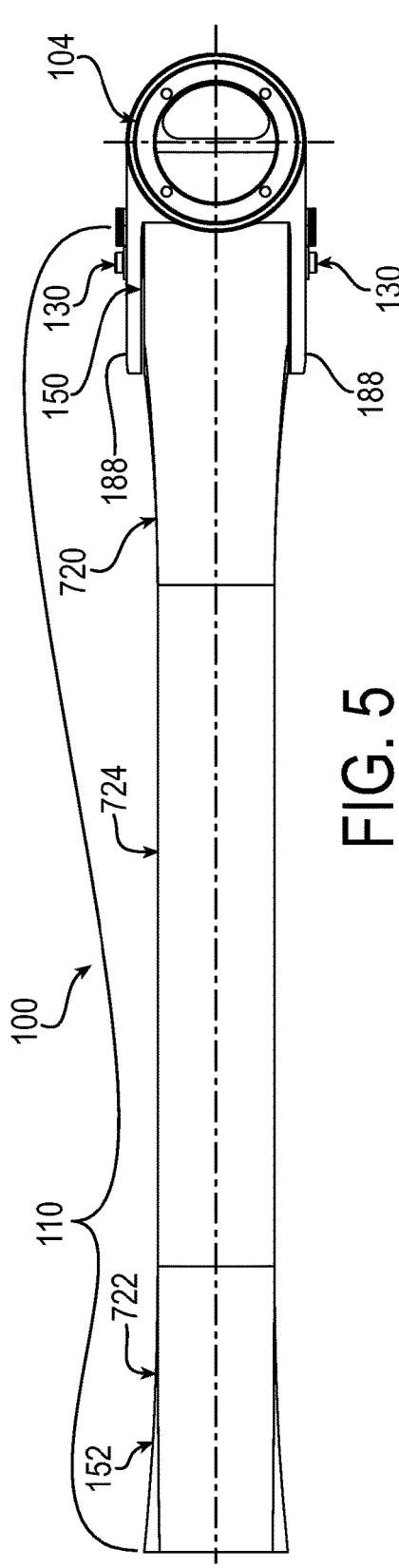
FIG. 5 is a top view of the FIG. 2 load balancing arm.
Figure 6:
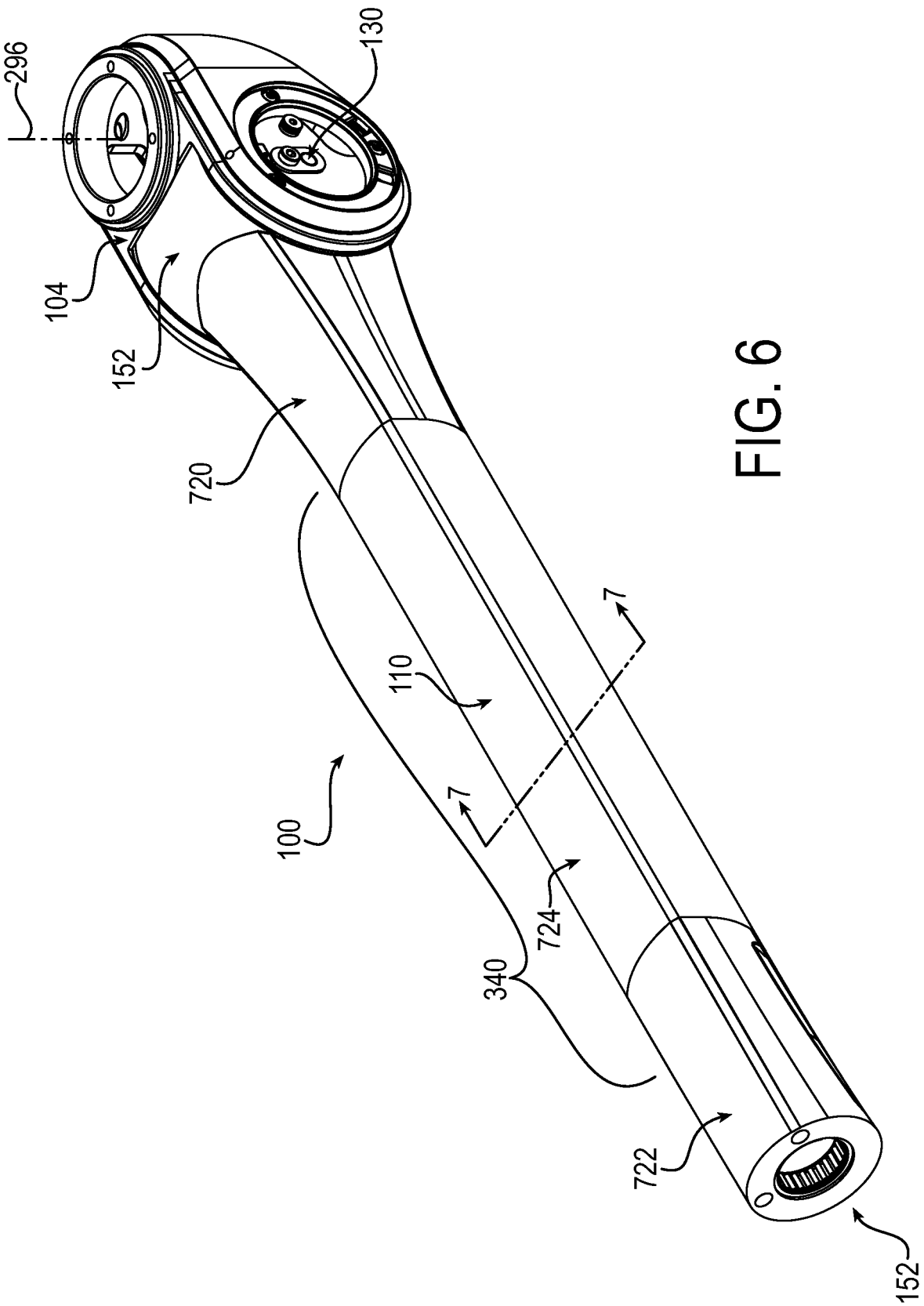
FIG. 6 is an end perspective view of the FIG. 2 load balancing arm, showing at a distal end thereof a connection receptacle for receipt of a medical device.

Reference is now made to FIGS. 2-6 and 15-20 which show greater detail of the support arm 110, the proximal hub 104, and the interface between the support arm 110 and proximal hub 104. As shown in FIGS. 2, 5 and 6, the proximal end 150 of the support arm 110 has a relatively smaller width than the proximal hub 104 and fits within the proximal hub 104. In the illustrated embodiment, the proximal end 150 of the support arm 110 includes a pair of vertically oriented laterally spaced protrusions or tongue portions 170 and a circular portion 178 substantially surrounding the tongue portions 170. As shown in FIGS. 3 and 4, the proximal hub 104 includes a mounting surface 184 for mounting the proximal hub 104 and thus the load balancing arm 100 to, for example, the distal end of an extension arm 16. The proximal hub 104 includes a pair of vertically oriented side walls 188 alongside which the tongue portions 170 of the support arm 110 slide during adjusting of the support arm 110. In side profile, the side walls 188 have a circular shape that corresponds in diameter to the circular portion 178 of the proximal end 150 of the support arm 110.

The proximal hub 104 also includes a load adjustment base 196 that extends width-wise between the pair of vertically oriented side walls 188 and that, as shown in FIGS. 15-20, extends vertically downward from a location just below the vertically uppermost portion of the circular portion 178 of the proximal end 150 of the support arm 110 downward approximately three fourths the distance across the circular portion 178. Details of one example of the load adjustment base 196 are shown in FIGS. 9, 10, 12-14 and 18-20. As shown in FIG. 10, the load adjustment base 196 may be fastened to the side walls 188 by fasteners 198. As shown in FIGS. 12-14, the load adjustment base 196 has a pair of laterally spaced flanges 204 that are recessed inward from the outer width of the load adjustment base 196. Referring to FIG. 9, the recessed flanges 204 form respective gaps 210 with the side walls 188 within which the tongue portions 170 of the support arm 110 are received. As shown in FIGS. 9, 12 and 18-20, the tongue portions 170 of the proximal end 150 of the support arm 110 have through holes 236 and the main bearing element 130 of the proximal hub 104 includes a pair of laterally spaced pins 240. The central axis of these pins 240 defines or coincides with the main pivot axis 132. The through holes 236 receive the pins 240 thereby to pivotably mount the proximal end 150 of the support arm 110 to the main bearing element 130 of the proximal hub 104 for pivotable movement of the support arm 110 about the main pivot axis 132.

In the illustrative embodiment, bushings 244 are provided on the pins 240 to promote smooth pivotable operation and serviceability. As shown in FIGS. 8, 10 and 12, the pins 240 are fixedly connected, for example by welding, to a retainer plate 252, which, in turn, is fastened to the side walls 188 of the proximal hub 104 by fasteners 258.

As shown in FIGS. 8 and 10, a load adjustment screw 280 is rotatably mounted in a bottom wall 284 of the load adjustment base 196. The load adjustment screw 280 is fixed in a vertical orientation in the proximal hub 104 and rotates about its own central axis 290. Referring to FIGS. 1-4 and 6, in the present embodiment, the axis 290 of the load adjustment screw 280 is parallel to an axis 296 of rotation of the load balancing arm 100 extending centrally through the support structure 24 and perpendicular to horizontal. As shown in FIGS. 9 and 12, the adjustable bearing element 108 includes a load adjustment nut 310 that threadably engages the load adjustment screw 280 to adjust the adjustable pivot axis 142 relative to the main pivot axis 132. The load adjustment nut 310 moves in the vertical direction as the load adjustment screw 280 is rotated, which vertical movement adjusts the adjustable pivot axis 142 relative to the main pivot axis 132. As shown in FIG. 9, the adjustable bearing element 108 includes a pin 324 that is carried by the load adjustment nut 310. The central axis of the pin 324 defines or coincides with the adjustable pivot axis 142. As shown in FIGS. 9 and 12, the proximal ends 160 of the links 124, 126 are pivotably mounted to the pin 324 at respective opposite ends of the pin 324. The adjustable pivot axis 142 is adjustable relative to the main pivot axis 132 over a range of adjustment 330, defined in the illustrative embodiment by the uppermost and lowermost vertical position of the load adjustment nut 310.

The vertical movement of the load adjustment nut 310 adjusts the load capacity of the load balancing arm 100. As will be appreciated, the distance between the adjustable pivot axis 142 of the pin 324 and the main pivot axis 132 of the proximal hub 104 provides the mechanical advantage, or moment, that allows the load balancing arm 100 to balance a medical device load 36 at the distal end 152 of the arm 100.

With reference to FIG. 12, the laterally spaced pins 240 split the main pivot axis 132 thereby enabling the adjustable bearing element 108 to be moved vertically across the main pivot axis 132 into a position between the laterally spaced pins 240. Accordingly, the adjustable bearing element 108 and the proximal ends 160 of the respective pair of links 124, 126 are movable between the pair of pins 240 over a portion of the range of adjustment 330. As will be appreciated, this provides greater adjustment range in the proximal ends 160 of the links 124, 126 pivotably mounted to the pin 324 of the adjustable bearing element 108 than if the pins 240 were a single pin member and the main pivot axis 132 was not split. As shown in FIGS. 17 and 20, the split main pivot axis 132, i.e. laterally spaced pins 240, also enables the proximal ends 160 of the links 124, 126 to move between the pins 240 for example when the load balancing arm 100 is pivoted to lower positions.

Referring to FIG. 4, the adjustable pivot axis 142 of the adjustable bearing element 108 is horizontally offset from the main pivot axis 132 of the main bearing element 130 in a direction toward the portion of the proximal hub 104 that includes the support structure 24. This offset allows for better balancing of the spring arm when a lighthead or other medical device is attached. It also slightly changes the dynamics of the load balancing arm 100 so that when above horizontal there is slightly more mechanical advantage about the main pivot axis 132 and when below horizontal there is slightly less mechanical advantage about the main pivot axis 132. As such, this allows the load balancing arm 100 to compensate for the spring force increasing as the arm 100 is moved to lower vertical positions, for example.

Turning now to FIGS. 6, 9 and 15-17, the support arm 110 includes an intermediate portion 340 between the proximal end 150 and distal end 152 of the support arm 110. The intermediate portion 340 has a relatively narrower height span than the circular portion 178 of the proximal end 150 of the support arm 110. The links 124, 126 (only link 124 is in view in FIGS. 15-17) have at least one bend that corresponds to the difference in height span between the intermediate portion 340 and the circular portion 178 of the proximal end 150 of the support arm 110. In the illustrative embodiment, the links 124, 126 have one bend and consequently have a J-shape in side view. Other shapes such as S-shape (two bends) are also contemplated. The bend in the links 124, 126 aids in the load balancing arm 100 having a smaller size and lower overall cross section profile than if the links 124, 126 were straight. The smaller size and lower overall cross section profile make the load balancing arm 100 less obstructive in the operating room and improve the laminar airflow around the surface of the load balancing arm 100.

Figure 7:
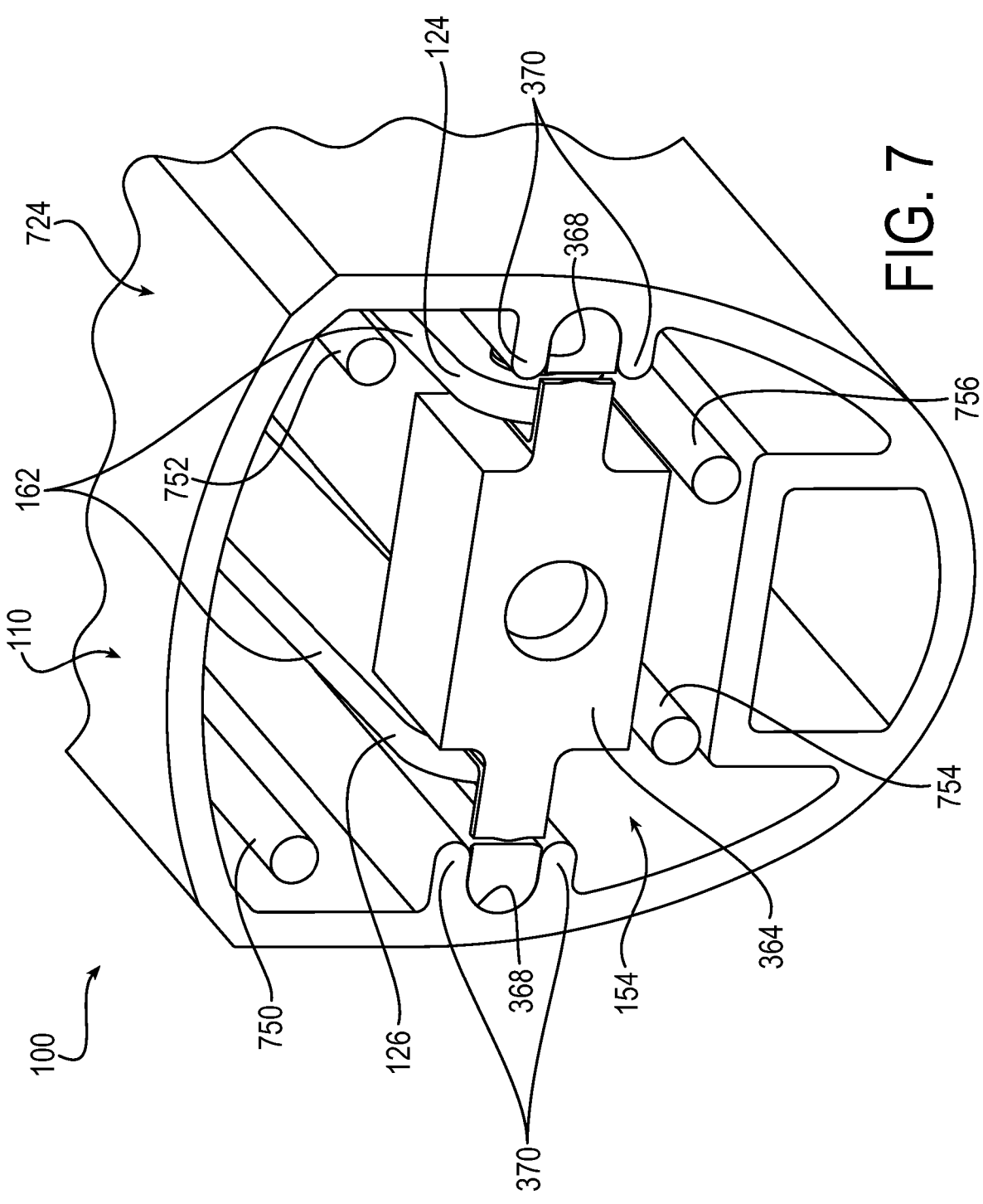
FIG. 7 is cross section view of the FIG. 2 load balancing arm as viewed from the plane 7-7 in FIG. 6.

The distal ends 162 of the links 124, 126 are pivotably mounted to the distal end 158 of the spring 116 via a carriage slide 364 that is slidable relative to the support arm 110. The pivotable connection may be facilitated by, for example, a pin 360 mounted within the carriage slide 384. As shown in FIG. 7, the carriage slide 364 is slidable within at least one groove 368 in the support arm 110, wherein in the illustrative embodiment there are two such grooves 368 at laterally opposite sides of the support arm 110. The grooves 368 are oriented along an axis that extends radially from and perpendicular to the main pivot axis 132. The grooves 368 are formed by parallel ribs 370 in the inward facing walls of the support arm 110. The ribs 370, along with a box shape member in the lower portion of the support arm 110, also serve as stiffening members.

The spring 116 of the load balancing arm 100 may be any type of counterbalancing member, and in the illustrative embodiment is a compression gas spring 116. Like the grooves 368, the spring 116 is oriented along an axis that extends radially from and perpendicular to the main pivot axis 132. The spring 116 has a cylinder 384 and a rod 388. Referring to FIGS. 11, 12 and 15-17, the cylinder 384 has a proximal end wall 390 that is coupled to a vertical beam 392 of the support arm 110. As shown in FIG. 11, the vertical beam 392 extends from a top wall 406 to a bottom wall 408 of the support arm 110 and is sufficiently narrow that the links 124, 126 straddle the vertical beam 392 on opposite lateral sides thereof throughout the pivotable range of the load balancing arm 100. The proximal end wall 390 of the cylinder 384 may be coupled to the vertical beam 392 in any suitable manner, for example as by a protrusion 418, shown in FIG. 12, that fits within an opening 420 in the vertical beam 392, shown in FIG. 11. The rod 388 is pivotably mounted to the distal ends 162 of the links 124, 126 via the pin 360 of the afore described carriage slide 364. In operation, the links 124, 126 straddle the spring 116 on laterally opposite sides of the spring 116 throughout the pivotable range of the load balancing arm 100.

Reference is now made to FIGS. 15-17, which show the load balancing arm 100 in three different vertical positions, and FIGS. 18-20, which show the links 124, 126 and the proximal end 150 of the support arm 110 relative to the proximal hub 104 in the three respective vertical positions. The links 124, 126 are shown adjusted to their maximum height in FIGS. 15-20, thereby maximizing the moment, or mechanical advantage, of the load balancing arm 100. In FIGS. 15 and 18, the support arm 110 is in a substantially horizontal position. In FIGS. 16 and 19, the support arm 110 is shown pivoted about the main pivot axis 132 about 30 degrees upward relative to horizontal. In FIGS. 17 and 20, the support arm 110 is shown pivoted about the main pivot axis 132 about 85 degrees downward from horizontal. As will be appreciated, then, the support arm 110 has an angle of rotation about the main pivot axis 132 of about 30 degrees upward from horizontal to about 85 degrees downward from horizontal.

FIGS. 21-38 show a load balancing arm 500 according to another embodiment of the invention. The load balancing arm 500 is in many respects similar to the above-referenced load balancing arm 100, and consequently the same reference numerals are used to denote structures corresponding to similar structures in the load balancing arm 100. In addition, the foregoing description of the load balancing arm 100 is equally applicable to the load balancing arm 500 except as noted below. Moreover, it will be appreciated upon reading and understanding the specification that aspects of the load balancing arms 100, 500 may be substituted for one another or used in conjunction with one another where applicable.

Turning then to FIGS. 21-38, there is shown a load balancing arm 500 of the medical device support system 10 in accordance with an embodiment of the invention. The load balancing arm 500 includes a proximal hub 104, an adjustable bearing element 108, a support arm 110, a spring 116, and one or more links, two such links 124, 126 in the illustrative embodiment, as shown in FIGS. 21-22 and 31-32. The load balancing arm 500 also includes a distal hub 510 shown in FIGS. 21, 23-25, 28 and 37-38, a parallel link 520 shown in FIGS. 22, 25, 27-32 and 34-38, and a load adjustment base 530 shown in FIGS. 22 and 31-33. The proximal hub 104 may include a support structure 24 such as the drop tube 24 (see FIG. 1). The proximal hub 104 includes a main bearing element 130 that defines a main pivot axis 132. The adjustable bearing element 108 defines an adjustable pivot axis 142 that is adjustable relative to the main pivot axis 132. The support arm 110 has a proximal end 150 and a distal end 152. The distal end 152 is pivotably mounted to the distal hub 510, which, in turn, is configured to support a medical device load 36 (see FIG. 1). The proximal end 150 is pivotably mounted to the main bearing element 130 for pivotable movement about the main pivot axis 132. The pivotable movement raises and lowers the height of the medical device load 36 at the distal end 152.

The spring 116 extends within a cavity 154 of the support arm 110 and is mounted to exert a biasing force between the main pivot axis 132 and a distal end 158 of the spring 116. The links 124, 126 each have a proximal end 160 and a distal end 162. The proximal end 160 is pivotably mounted to the adjustable bearing element 108 for pivotable movement about the adjustable pivot axis 142. The distal ends 162 of the links 124, 126 are pivotably mounted to the distal end 158 of the spring 116 such that the biasing force exerted by the spring 116 is transmitted through the links 124, 126 to the adjustable bearing element 108 thereby to generate a moment about the main pivot axis 132 of the proximal hub 104 that counters a moment generated by the medical device load 36 at the distal end 152 of the support arm 110, thereby balancing the medical device load 36.

Thus, in the load balancing arm 500 according to the present embodiment, the links 124, 126 connect at their proximal ends 160 to an adjustment bearing element 108 and at their distal ends 162 to the distal end 158 of the spring 116. As will be described in greater detail below, the attachment at the distal end 158 of the spring 116 allows for a relatively longer link than if connected to the proximal end of the spring 116. The inventors have found that this allows for a better force transmission and less spring travel resulting in a more balanced load balancing arm 500 throughout the pivotable range of travel of the arm 500.

Reference is now made to FIGS. 21-27, 31 and 34-36, which show greater detail of the support arm 110, the proximal hub 104, and the interface between the support arm 110 and proximal hub 104. As shown in FIGS. 21-22 and 31, the proximal end 150 of the support arm 110 has a relatively smaller width than the proximal hub 104 and fits within the proximal hub 104. In the illustrated embodiment, the proximal end 150 of the support arm 110 includes a pair of vertically oriented laterally spaced protrusions or tongue portions 170 and a circular portion 178 substantially surrounding the tongue portions 170. As shown in FIGS. 22, 26 and 31, the proximal hub 104 includes a mounting surface 184 for mounting the proximal hub 104 and thus the load balancing arm 100 to, for example, the distal end of an extension arm 16. The proximal hub 104 includes a pair of vertically oriented side walls 188 alongside which the tongue portions 170 of the support arm 110 slide during adjusting of the support arm 110. In side profile, the side walls 188 have a circular shape that corresponds in diameter to the circular portion 178 of the proximal end 150 of the support arm 110.

The proximal hub 104 also includes a load adjustment base 530 that extends width-wise between the pair of vertically oriented side walls 188 and that, as shown in FIGS. 22, 27 and 34-36 extends vertically downward from a location just below the vertically uppermost portion of the circular portion 178 of the proximal end 150 of the support arm 110 downward approximately three fourths the distance across the circular portion 178. Details of one example of the load adjustment base 530 are shown in FIGS. 22, 24-27 and 31-36. As shown in FIGS. 26 and 31, the load adjustment base 530 may be fastened to the side walls 188 by fasteners 198. As shown in FIGS. 26 and 31-33, the load adjustment base 530 has a pair of laterally spaced flanges 204 that are recessed inward from the outer width of the load adjustment base 530. Referring to FIG. 26, the recessed flanges 204 form respective gaps 210 with the side walls 188 within which the tongue portions 170 of the support arm 110 are received. As shown in FIG. 26, the tongue portions 170 of the proximal end 150 of the support arm 110 have through holes 236 and the main bearing element 130 of the proximal hub 104 includes a pair of laterally spaced pins 240. The central axis of these pins 240 defines or coincides with the main pivot axis 132. The through holes 236 receive the pins 240 thereby to pivotably mount the proximal end 150 of the support arm 110 to the main bearing element 130 of the proximal hub 104 for pivotable movement of the support arm 110 about the main pivot axis 132.

In the illustrative embodiment, bushings 244 are provided on the pins 240 to promote smooth pivotable operation and serviceability. As shown in FIGS. 23, 26 and 31, the pins 240 are fixedly connected, for example by welding, to a retainer plate 252, which, in turn, is fastened to the side walls 188 of the proximal hub 104 by fasteners 258.

As shown in FIGS. 22, 27, 32 and 33, a load adjustment screw 280 is rotatably mounted in a bottom wall 284 of the load adjustment base 530. The load adjustment screw 280 is fixed in a vertical orientation in the proximal hub 104 and rotates about its own central axis 290. Referring to FIGS. 1 and 27, in the present embodiment, the axis 290 of the load adjustment screw 280 is parallel to an axis 296 of rotation of the load balancing arm 500 extending centrally through the support structure 24 and perpendicular to horizontal. As shown in FIGS. 25-27 and 32, the adjustable bearing element 108 includes a load adjustment nut 310 that threadably engages the load adjustment screw 280 to adjust the adjustable pivot axis 142 relative to the main pivot axis 132. The load adjustment nut 310 moves in the vertical direction as the load adjustment screw 280 is rotated, which vertical movement adjusts the adjustable pivot axis 142 relative to the main pivot axis 132. As shown in FIGS. 26 and 27, the adjustable bearing element 108 includes a pin 324 that is carried by the load adjustment nut 310. The central axis of the pin 324 defines or coincides with the adjustable pivot axis 142. As shown in FIGS. 26, 27 and 32, the proximal ends 160 of the links 124, 126 are pivotably mounted to the pin 324 at respective opposite ends of the pin 324. The adjustable pivot axis 142 is adjustable relative to the main pivot axis 132 over a range of adjustment 330, defined in the illustrative embodiment by the uppermost and lowermost vertical position of the load adjustment nut 310, as shown in FIG. 32.

The vertical movement of the load adjustment nut 310 adjusts the load capacity of the load balancing arm 500. As will be appreciated, the distance between the adjustable pivot axis 142 of the pin 324 and the main pivot axis 132 of the proximal hub 104 provides the mechanical advantage, or moment, that allows the load balancing arm 500 to balance a medical device load 36 at the distal end 152 of the arm 500.

With reference to FIG. 26, the laterally spaced pins 240 split the main pivot axis 132 thereby enabling the adjustable bearing element 108 to be moved vertically across the main pivot axis 132 into a position between the laterally spaced pins 240. Accordingly, the adjustable bearing element 108 and the proximal ends 160 of the respective pair of links 124, 126 are movable between the pair of pins 240 over a portion of the range of adjustment 330. As will be appreciated, this provides greater adjustment range in the proximal ends 160 of the links 124, 126 pivotably mounted to the pin 324 of the adjustable bearing element 108 than if the pins 240 were a single pin member and the main pivot axis 132 was not split.

Referring to FIGS. 26 and 27, the adjustable pivot axis 142 of the adjustable bearing element 108 and the main pivot axis 132 of the main bearing element 130 are horizontally offset the same distance from the axis 296 of rotation of the load balancing arm 500 extending centrally through the support structure 24.

Turning now to FIGS. 22, 27 and 34-36, the support arm 110 includes an intermediate portion 340 between the proximal end 150 and distal end 152 of the support arm 110. The intermediate portion 340 has a relatively narrower height span than the circular portion 178 of the proximal end 150 of the support arm 110. The links 124, 126 (only link 124 is in view in FIGS. 34-36) have at least one bend that corresponds to the difference in height span between the intermediate portion 340 and the circular portion 178 of the proximal end 150 of the support arm 110. In the illustrative embodiment, the links 124, 126 have one bend and consequently have a J-shape in side view. Other shapes such as S-shape (two bends) are also contemplated. The bend in the links 124, 126 aids in the load balancing arm 500 having a smaller size and lower overall cross section profile than if the links 124, 126 were straight. The smaller size and lower overall cross section profile make the load balancing arm 500 less obstructive in the operating room and improve the laminar airflow around the surface of the load balancing arm 100.

The distal ends 162 of the links 124, 126 are pivotably mounted to the distal end 158 of the spring 116 via a carriage slide 364 that is slidable relative to the support arm 110. The pivotable connection may be facilitated by, for example, a pin 360 mounted within the carriage slide 384. As shown in FIG. 29, the carriage slide 364 is slidable within at least one groove 368 in the support arm 110, wherein in the illustrative embodiment there are two such grooves 368 at laterally opposite sides of the support arm 110. The grooves 368 are oriented along an axis that extends radially from and perpendicular to the main pivot axis 132. The grooves 368 are formed by parallel ribs 370 in the inward facing walls of the support arm 110. The ribs 370, along with a horizontal cross beam in the bottom portion of the support arm 110, also serve as stiffening members.

The spring 116 of the load balancing arm 500 may be any type of counterbalancing member, and in the illustrative embodiment is a compression gas spring 116. Like the grooves 368, the spring 116 is oriented along an axis that extends radially from and perpendicular to the main pivot axis 132. The spring 116 has a cylinder 384 and a rod 388. Referring to FIGS. 22, 24, 27 and 32, the cylinder 384 has a proximal end wall 390 that is coupled to a vertical beam 392 of the support arm 110. As shown in FIG. 22, the vertical beam 392 extends from a top wall 406 to a bottom wall 408 of the support arm 110 and is sufficiently narrow that the links 124, 126 straddle the vertical beam 392 on opposite lateral sides thereof throughout the pivotable range of the load balancing arm 500. The proximal end wall 390 of the cylinder 384 may be coupled to the vertical beam 392 in any suitable manner, for example as by a protrusion 418, shown in FIG. 32, that fits within an opening 420 in the vertical beam 392, shown in FIGS. 24 and 25. The rod 388 is pivotably mounted to the distal ends 162 of the links 124, 126 via the pin 360 of the afore described carriage slide 364. In operation, the links 124, 126 straddle the spring 116 on laterally opposite sides of the spring 116 throughout the pivotable range of the load balancing arm 500.

FIGS. 21, 23-25, 28 and 37-38 show detail of the distal hub 510 of the load balancing arm 500. The distal hub 510 is pivotably connected to the distal end 152 of the support arm 110 via a pair of laterally spaced pins 540 held in flanges of a vertical block 544 of the distal hub 510. The vertical block 544 can be fixedly connected to a pair of vertically oriented side walls 548 of the distal hub 510 in a similar manner that the load adjustment base 530 is connected to the side walls 188 of the proximal hub 104. Likewise, the distal end 152 of the support arm 110 can include laterally spaced protrusions 566 that pivotably connect to the respective laterally spaced pins 540 in a similar manner that the proximal end protrusions 170 pivotably connect to the laterally spaced pins 240 of the proximal hub 104.

FIGS. 22, 25, 27-32 and 34-38 show detail of the parallel link 520 of the load balancing arm 500. The illustrative parallel link 520 is a single U-shape link with two vertically oriented laterally spaced parallel side walls 564 and a lower bridge member 568 connecting the bottom edges of the side walls 564. It will be appreciated that the parallel link 520 may comprise two parallel links in the form of the two parallel side walls 564 with the lower bridge member 568 omitted. Referring to FIGS. 29 and 30, in the present embodiment, the parallel link 520 is made up of two pieces, a U-shape stainless steel member 570 and a pair of relatively harder stainless steel side braces 572 tack welded to the U-shape stainless steel member 570.

The parallel link 520 is pivotably connected at its proximal end 580 to a pin 582 supported by the load adjustment base 530 of the proximal hub 104 and at its distal end 586 to a pin 588 supported by the vertical block 544 of the distal hub 510. As shown in FIG. 35, the split main pivot axis 132, i.e. the laterally spaced pins 240, enable the proximal end 580 of the parallel link 520 to move between the pins 240 for example when the load balancing arm 500 is pivoted to upper positions. Likewise, as shown in FIGS. 25 and 36, the split pivot axis 590, i.e. the laterally spaced pins 540, enable the distal end 586 of the parallel link 520 to move between the pins 540 for example when the load balancing arm 500 is pivoted to lower positions.

As shown in FIGS. 27 and 28, the pin 582 is oriented vertically below the pins 240 a distance 600 and the pin 588 is oriented vertically below the pins 540 by the same distance 600. Also, the horizontal distance between the pins 540 and the pins 240 at opposite ends of the support arm 110 is equal to the horizontal distance between the pin 588 and the pin 582 at opposite ends of the parallel link 520. In this way, a parallelogram is formed by the structure of the support arm 110 between the pins 540 and the pins 240, the portion of the load adjustment base 530 between the pins 240 and the pin 582, the parallel link 520 between the pin 582 and the pin 588, and the portion of the vertical block 544 between the pin 588 and the pins 540. Referring to FIGS. 34-38, owing to this parallelogram linkage, the vertically aligned pins 540, 588 at the distal end 152 remain parallel to the vertically aligned pins 240, 582 at the proximal end 150 throughout the pivotable range of the load balancing arm 500 about the main pivot axis 132. This permits a medical device load 36 such as a monitor to remain properly oriented regardless of its vertical displacement from the ceiling of the operating room.

Referring now to FIGS. 22, 25, 26, 31 and 32, the side walls 564 of the parallel link 520 straddle the vertically lower portion of the gas spring 116 on laterally opposite sides thereof. The side walls 564 also straddle the links 124, 126 on laterally opposite sides of the links 124, 126 over at least a portion of the pivotable range of the load adjustment arm 500, particularly when the adjustable bearing element 108 is in lower positions as shown in FIG. 24.

Reference is now made to FIGS. 34-36, which show the load balancing arm 500 in three different vertical positions, and FIGS. 37 and 38, which show the parallel link 520 and the distal end 152 of the support arm 110 relative to the distal hub 510 in the respective uppermost and lowermost vertical positions. The links 124, 126 are shown adjusted to their maximum height in FIGS. 34-36, thereby maximizing the moment, or mechanical advantage, of the load balancing arm 500. In FIG. 34, the support arm 110 is in a substantially horizontal position. In FIGS. 35 and 37, the support arm 110 is shown pivoted about the main pivot axis 132 about 40 degrees upward relative to horizontal. In FIGS. 36 and 38, the support arm 110 is shown pivoted about the main pivot axis 132 about 40 degrees downward from horizontal. As will be appreciated, then, the support arm 110 has an angle of rotation about the main pivot axis 132 of about 40 degrees upward from horizontal to about 40 degrees downward from horizontal.

Turning now to FIGS. 39-47, there is shown greater detail of the support arm 110, or support arm structure or housing, of the FIG. 2 load balancing arm 100 in accordance with an embodiment of the invention. The support arm 110 has a longitudinal axis 700 and along that axis 700 the support arm 110 includes a proximal hub 720 at its proximal end 150, a distal hub 722 at its distal end 152, and an intermediate beam 724 between the proximal hub 720 and the distal hub 722. In relation to the proximal hub 104, the proximal hub 720 may be referred to as an inner proximal hub 720 while the proximal hub 104 may be referred to as an outer proximal hub 104. A cavity 736 extends longitudinally through the intermediate beam 724 the entire length of the intermediate beam 724. At least one tension member, four such tension members 750, 752, 754, 756 (collectively 750-756) in the illustrative embodiment, extend through the cavity 736 of the intermediate beam 724. The tension members 750-756 are secured at their proximal ends 760 to the proximal hub 720 and at their distal ends 762 to the distal hub 722. The tension members 750-756 are in a state of tension and the intermediate beam 724 is in a state of compression. Thus, the intermediate beam 724 can be said to be "sandwiched" between the proximal hub 720 and distal hub 722. As will be described in greater detail below, the tension members 750-756 allow for a more compact and lighter weight support arm 110, and thus load balancing arm 100, than what was heretofore provided, and a support arm 110 that has no visible fasteners. The tension members 750-756 extend through the intermediate beam 724 without contacting or engaging the intermediate beam 724. This can be seen for example in FIG. 7. It will be appreciated that although the illustrative tension members 750-756 have the same length, in alternative embodiments the tension members 750-756 may have different lengths as the case may be. As shown in FIGS. 39-41, the proximal ends 760 of the tension members 750-756 connect to the inner proximal hub 720. The inner proximal hub 720, in turn, fits within and is pivotally connected to the outer proximal hub 104, as earlier described. As shown in FIGS. 39, 42 and 43, the distal ends 762 of the tension members 750-756 connect to the distal hub 722. The distal hub 722, in turn, supports a medical device load 36, as shown in FIG. 1.

FIGS. 40 and 41 show greater detail of the connection between the proximal hub 720 and the intermediate beam 724. The proximal hub 720 has two threaded holes 780, 782 in an upper portion of the proximal hub 720 and two threaded holes 784, 786 in a lower portion of the proximal hub 720. In the illustrative embodiment, the proximal hub 720 includes a tubular end wall 800 that mates with a proximal end 804 of the intermediate beam 724, and the two upper threaded holes 780, 782 are in bosses 810, 812 that project radially inwardly from an inward facing wall 828 of the tubular end wall 800. The two lower threaded holes 784, 786 are in the vertical beam 392 that extends from the top wall 406 to the bottom wall 408 of the proximal hub 720. Thus, and with reference to FIGS. 11, 15-17 and 41, the two lower threaded holes 784, 786 are horizontally offset a distance 836 from the two upper threaded holes 780, 782 along the longitudinal axis 700 in a direction toward the main pivot axis 132 or axis 296 of rotation of the load balancing arm 100.

The two upper tension members 750, 752 are threaded at their proximal ends 760 for threaded engagement with the threaded holes 780, 782 in the bosses 810, 812. Similarly, the two lower tension members 754, 756 are threaded at their proximal ends 760 for threaded engagement with the threaded holes 784, 786 in the vertical beam 392. The proximal ends 760 of the tension members 750-756 are threaded into the respective threaded holes 780-786 to secure or fixedly connect the tension members 750-756 to the proximal hub 720.

FIGS. 42 and 43 show greater detail of the connection between the distal hub 722 and the intermediate beam 724. The distal hub 722 has two clearance holes 840, 842 in an upper portion of the distal hub 722 and two clearance holes 844, 846 in a lower portion of the distal hub 722. In the illustrative embodiment, the distal hub 722 includes a tubular end wall 860 that mates with a distal end 864 of the intermediate beam 724, and the two upper clearance holes 840, 842 and two lower clearance holes 844, 846 are in bosses 880, 882, 884, 886 that project radially inwardly from an inward facing wall 888 of the tubular end wall 860. With reference to FIGS. 15-17 and 43, the two lower clearance holes 844, 846 are horizontally offset a distance 896 from the two upper clearance holes 840, 842 along the longitudinal axis 700 in a direction toward the main pivot axis 132 or axis 296 of rotation of the load balancing arm 100.

The two upper tension members 750, 752 pass through the clearance holes 840, 842 in the bosses 880, 882 such that their distal ends 762 are exposed. Similarly, the two lower tension members 754, 756 pass through the clearance holes 844, 846 in the bosses 884, 886 such that their distal ends 762 are exposed. The exposed distal ends 762 of the tension members 750-756 are threaded. Retainers 900, 902, 904, 906 such as the illustrative cylindrical nuts 900, 902, 904, 906 thread onto the exposed distal ends 762 of the tension members 750-756 such that the retainers 900, 902, 904, 906 abut respective flats 920, 922, 924, 926 of the bosses 880-886.

As the retainers 900-906 are tightened against the flats 920-926 of the bosses 880-886, the retainers 900-906 draw the tension members 750-756 through the clearance holes 840-846, urging the proximal hub 720 and the distal hub 722 toward one another. As the proximal hub 720 and distal hub 722 are urged toward one another, the proximal hub 720 and distal hub 722 compress the intermediate beam 724 therebetween, generating a tensile load in the tension members 750-756 and a compressive load in the intermediate beam 724. The tensile loaded tension members 750-756 and compressively loaded intermediate beam 724 hold the proximal hub 720, distal hub 722 and intermediate beam 724 together along the longitudinal axis 700. As will be appreciated, the retainers 900-906 are tightened to a specific torque rating suitable for maintaining the proximal hub 720, distal hub 722 and intermediate beam 724 secured together.

FIGS. 44-47 show examples of mating walls of the proximal hub 720, distal hub 722 and intermediate beam 724. The proximal hub 720 includes a tubular end wall 800 that mates with a tubular end wall 940 at the proximal end 804 of the intermediate beam 724. Similarly, the distal hub 722 includes a tubular end wall 860 that mates with a tubular end wall 944 at the distal end 864 of the intermediate beam 724. In the illustrative embodiment, the tubular end walls 800, 860, 940, 944 have a noncircular shape in axial cross section. The tubular end wall 800 of the proximal hub 720 has an outer periphery that is slightly smaller than the inner periphery of the tubular end wall 940 of the intermediate beam 724. Accordingly, tubular end wall 800 of the proximal hub 720 fits into the tubular end wall 940 of the intermediate beam 724 such that the tubular end walls 800, 940 overlap along the longitudinal axis 700. The tubular end wall 860 of the distal hub 722 has an outer periphery that is slightly smaller than the inner periphery of the tubular end wall 944 of the intermediate beam 724. Accordingly, tubular end wall 860 of the distal hub 722 fits into the tubular end wall 944 of the intermediate beam 724 such that the tubular end walls 860, 944 overlap along the longitudinal axis 700. As their cross section shapes are noncircular, torsional loading is transferred from the tubular end wall 800 to the tubular end wall 940 and vice versa, and from the tubular end wall 860 to the tubular end wall 944 and vice versa. This substantially eliminates or minimizes torsional loading on the tension members 750-756.

As shown in FIGS. 45 and 46, the tubular end wall 800 of the proximal hub 720 has a shoulder 954 and the tubular end wall 940 of the intermediate beam 724 has a stop face 958 that abuts the shoulder 954 when the proximal hub 720 is connected to the intermediate beam 724. Similarly, as shown in FIGS. 44 and 47, the tubular end wall 860 of the distal hub 722 has a shoulder 964 and the tubular end wall 944 of the intermediate beam 724 has a stop face 968 that abuts the shoulder 954 when the proximal hub 720 is connected to the intermediate beam 724. The thickness of the shoulders 954, 964 is the same as that of the stop faces 958, 968 to provide a smooth transition in the outer surfaces of the proximal hub 720, the distal hub 722, and the intermediate beam 724 along the longitudinal axis 700, which improves the laminar airflow around the surface of the load balancing arm 100.

The tension members 750-756 can be made of any suitable tensile load bearing member, including for example a threaded rod, a steel cable, a plastic cable, among others. In the present embodiment, the intermediate beam 724 is an extruded member and the proximal hub 720 and distal hub 722 are cast members. It will be appreciated, of course, that other manufacturing processes may be used such as pultrusion and additive manufacturing techniques.

FIGS. 48-56 show greater detail of the support arm 110, or support arm structure or housing, of the FIG. 21 load balancing arm 500 in accordance with an embodiment of the invention. The FIG. 48 support arm 110 is in many respects similar to the above-referenced FIG. 39 support arm 110, and consequently the same reference numerals are used to denote structures corresponding to similar structures in the FIG. 39 support arm 110. In addition, the foregoing description of the FIG. 39 support arm 110 is equally applicable to the FIG. 48 support arm 110 except as noted below. Moreover, it will be appreciated upon reading and understanding the specification that aspects of the FIG. 39 and FIG. 48 supports arms 110 may be substituted for one another or used in conjunction with one another where applicable.

Turning then to FIGS. 48-56, there is shown greater detail of the support arm 110, or support arm structure or housing, of the FIG. 21 load balancing arm 500 in accordance with an embodiment of the invention. The support arm 110 has a longitudinal axis 1000 and along that axis 1000 the support arm 110 includes a proximal hub 1020 at its proximal end 150, a distal hub 1022 at its distal end 152, and an intermediate beam 1024 between the proximal hub 1020 and the distal hub 1022. In relation to the proximal hub 104, the proximal hub 1020 may be referred to as an inner proximal hub 1020 while the proximal hub 104 may be referred to as an outer proximal hub 104. Similarly, in relation to the distal hub 510, the distal hub 1022 may be referred to as an inner distal hub 1022 while the distal hub 510 may be referred to as an outer distal hub 510. A cavity 1036 extends longitudinally through the intermediate beam 1024 the entire length of the intermediate beam 1024. At least one tension member, four such tension members 1050, 1052, 1054, 1056 (collectively 1050-1056) in the illustrative embodiment, extend through the cavity 1036 of the intermediate beam 1024. The tension members 1050-1056 are secured at their proximal ends 1060 to the proximal hub 1020 and at their distal ends 1062 to the distal hub 1022. The tension members 1050-1056 are in a state of tension and the intermediate beam 1024 is in a state of compression. Thus, the intermediate beam 1024 can be said to be "sandwiched" between the proximal hub 1020 and distal hub 1022. As will be described in greater detail below, the tension members 1050-1056 allow for a more compact and lighter weight support arm 110, and thus load balancing arm 500, than what was heretofore provided, and a support arm 110 that has no visible fasteners.

The tension members 1050-1056 extend through the intermediate beam 1024 without contacting or engaging the intermediate beam 1024. This can be seen for example in FIG. 29. It will be appreciated that although the illustrative tension members 1050-1056 have the same length, in alternative embodiments the tension members 1050-1056 may have different lengths as the case may be. As shown in FIGS. 48-50, the proximal ends 1060 of the tension members 1050-1056 connect to the inner proximal hub 1020. The inner proximal hub 1020, in turn, fits within and is pivotably connected to the outer proximal hub 104, as earlier described. As shown in FIGS. 48, 51 and 52, the distal ends 1062 of the tension members 1050-1056 connect to the distal hub 1022. The distal hub 1022, in turn, fits within and is pivotably connected to the outer distal hub 510, as earlier described. The outer distal hub 510, in turn, supports a medical device load 36, as was described with respect to FIG. 1.

FIGS. 49 and 50 show greater detail of the connection between the proximal hub 1020 and the intermediate beam 1024. The proximal hub 1020 has two threaded holes 1080, 1082 in an upper portion of the proximal hub 1020 and two threaded holes 1084, 1086 in a lower portion of the proximal hub 1020. In the illustrative embodiment, the proximal hub 1020 includes a tubular end wall 1100 that mates with a proximal end 1104 of the intermediate beam 1024, and the two upper threaded holes 1080, 1082 and the two lower threaded holes 1084, 1086 are in bosses 1110, 1112, 1114, 1116 that project radially inwardly from an inward facing wall 1128 of the tubular end wall 1100.

The two upper tension members 1050, 1052 are threaded at their proximal ends 1060 for threaded engagement with the threaded holes 1080, 1082 in the bosses 1110, 1112. Similarly, the two lower tension members 1054, 1056 are threaded at their proximal ends 1060 for threaded engagement with the threaded holes 1084, 1086 in the bosses 1114, 1116. The proximal ends 1060 of the tension members 1050-1056 are threaded into the respective threaded holes 1080-1086 to secure or fixedly connect the tension members 1050-1056 to the proximal hub 1020.

FIGS. 51 and 52 show greater detail of the connection between the distal hub 1022 and the intermediate beam 1024. The distal hub 1022 has two clearance holes 1140, 1142 in an upper portion of the distal hub 1022 and two clearance holes 1144, 1146 in a lower portion of the distal hub 1022. In the illustrative embodiment, the distal hub 1022 includes a tubular end wall 1160 that mates with a distal end 1164 of the intermediate beam 1024, and the two upper clearance holes 1140, 1142 and two lower clearance holes 1144, 1146 are in bosses 1180, 1182, 1184, 1186 that project radially inwardly from an inward facing wall 1188 of the tubular end wall 1160.

The two upper tension members 1050, 1052 pass through the clearance holes 1140, 1142 in the bosses 1180, 1182 such that their distal ends 1062 are exposed. Similarly, the two lower tension members 1054, 1056 pass through the clearance holes 1144, 1146 in the bosses 1184, 1186 such that their distal ends 1062 are exposed. The exposed distal ends 1062 of the tension members 1050-1056 are threaded. Retainers 1200, 1202, 1204, 1206 such as the illustrative cylindrical nuts 1200, 1202, 1204, 1206 thread onto the exposed distal ends 1062 of the tension members 1050-1056 such that the retainers 1200, 1202, 1204, 1206 abut respective flats 1220, 1222, 1224, 1226 of the bosses 1180-1186. As will be appreciated, the retainers 1200-1206 are tightened to a specific torque rating suitable for maintaining the proximal hub 1020, distal hub 1022 and intermediate beam 1024 secured together.

As the retainers 1200-1206 are tightened against the flats 1220-1226 of the bosses 1180-1186, the retainers 1200-1206 draw the tension members 1050-1056 through the clearance holes 1140-1146, urging the proximal hub 1020 and the distal hub 1022 toward one another. As the proximal hub 1020 and distal hub 1022 are urged toward one another, the proximal hub 1020 and distal hub 1022 compress the intermediate beam 1024 therebetween, generating a tensile load in the tension members 1050-1056 and a compressive load in the intermediate beam 1024. The tensile loaded tension members 1050-1056 and compressively loaded intermediate beam 1024 hold the proximal hub 1020, distal hub 1022 and intermediate beam 1024 together along the longitudinal axis 1000.

FIGS. 53-56 show examples of mating walls of the proximal hub 1020, distal hub 1022 and intermediate beam 1024. The proximal hub 1020 includes a tubular end wall 1100 that mates with a tubular end wall 1240 at the proximal end 1104 of the intermediate beam 1024. Similarly, the distal hub 1022 includes a tubular end wall 1160 that mates with a tubular end wall 1244 at the distal end 1164 of the intermediate beam 1024. In the illustrative embodiment, the tubular end walls 1100, 1160, 1240, 1244 have a noncircular shape in axial cross section. The tubular end wall 1100 of the proximal hub 1020 has an outer periphery that is slightly smaller than the inner periphery of the tubular end wall 1240 of the intermediate beam 1024. Accordingly, tubular end wall 1100 of the proximal hub 1020 fits into the tubular end wall 1240 of the intermediate beam 724 such that the tubular end walls 1100, 1240 overlap along the longitudinal axis 1000. The tubular end wall 1160 of the distal hub 1022 has an outer periphery that is slightly smaller than the inner periphery of the tubular end wall 1244 of the intermediate beam 1024. Accordingly, tubular end wall 1160 of the distal hub 1022 fits into the tubular end wall 1244 of the intermediate beam 1024 such that the tubular end walls 1160, 1244 overlap along the longitudinal axis 1000. As their cross section shapes are noncircular, torsional loading is transferred from the tubular end wall 1100 to the tubular end wall 1240 and vice versa, and from the tubular end wall 1160 to the tubular end wall 1244 and vice versa. This substantially eliminates or minimizes torsional loading on the tension members 1050-1056.

As shown in FIGS. 54 and 55, the tubular end wall 1100 of the proximal hub 1020 has a shoulder 1254 and the tubular end wall 1240 of the intermediate beam 1024 has a stop face 1258 that abuts the shoulder 1254 when the proximal hub 1020 is connected to the intermediate beam 1024. Similarly, as shown in FIGS. 53 and 56, the tubular end wall 1160 of the distal hub 1022 has a shoulder 1264 and the tubular end wall 1244 of the intermediate beam 1024 has a stop face 1268 that abuts the shoulder 1254 when the proximal hub 1020 is connected to the intermediate beam 1024. The thickness of the shoulders 1254, 1264 is the same as that of the stop faces 1258, 1268 to provide a smooth transition in the outer surfaces of the proximal hub 1020, the distal hub 1022, and the intermediate beam 1024 along the longitudinal axis 1000, which improves the laminar airflow around the surface of the load balancing arm 500.

Referring again to FIGS. 53-56, the proximal hub 1020 and distal hub 1022 include respective upper plugs 1300, 1302 and lower plugs 1310, 1312 that fit, or plug, into respective upper receptacles 1340, 1342 and lower receptacles 1350, 1352 in the proximal and distal ends 1104, 1164 of the intermediate beam 1024. In the illustrative embodiment, the upper bosses 1110, 1112 of the proximal hub 1020 form part of the upper plug 1300 of the proximal hub 1020; the lower bosses 1114, 1116 of the proximal hub 1020 form part of the lower plug 1310 of the proximal hub 1020; the upper bosses 1180, 1182 of the distal hub 1022 form part of the upper plug 1302 of the distal hub 1020; and the lower bosses 1184, 1186 of the distal hub 1022 form part of the lower plug 1312 of the distal hub 1022.

As shown in FIGS. 54 and 55, the upper plug 1300 of the proximal hub 1020 has an inverted U-shape in which the base 1360 abuts an upper inward facing wall 1364 of the intermediate beam 1024 and the distal ends 1366 of the legs 1368, 1370 abut respective upper surfaces 1374, 1376 of the parallel ribs 370 in the laterally opposite side walls of the intermediate beam 1024. The lower plug 1310 of the proximal hub 1020 has a U-shape in which the base 1390 abuts a lower inward facing wall 1394 of the intermediate beam 1024 and the distal ends 1396 of the legs 1398, 1400 abut a lower surface 1404 of a cross beam 1408 extending between laterally opposite side walls of the intermediate beam 1024. As will be appreciated, the abutting contact between the leg 1368 and the upper surface 1374 and the abutting contact between the leg 1400 and the lower surface 1404 further aid in transferring torsional loading from the proximal hub 1020 to the proximal end 1104 of the intermediate beam 1024 and vice versa in one torsional direction, and the abutting contact between the leg 1366 and upper surface 1376 and the abutting contact between the leg 1398 and the lower surface 1404 further aid in transferring torsional loading from the proximal hub 1020 to the proximal end 1104 of the intermediate beam 1024 and vice versa in an opposite torsional direction.

As shown in FIGS. 53 and 56, the upper plug 1302 of the distal hub 1022 has an inverted U-shape in which the base 1560 abuts the upper inward facing wall 1364 of the intermediate beam 1024 and the distal ends 1566 of the legs 1568, 1570 abut respective upper surfaces 1374, 1376 of the parallel ribs 370 in the laterally opposite side walls of the intermediate beam 1024. The lower plug 1312 of the distal hub 1022 has a U-shape in which the base 1590 abuts the lower inward facing wall 1394 of the intermediate beam 1024 and the distal ends 1596 of the legs 1598, 1600 abut the lower surface 1404 of the cross beam 1408 extending between laterally opposite side walls of the intermediate beam 1024. As will be appreciated, the abutting contact between the leg 1568 and the upper surface 1374 and the abutting contact between the leg 1600 and the lower surface 1404 further aid in transferring torsional loading from the distal hub 1022 to the distal end 1164 of the intermediate beam 1024 and vice versa in one torsional direction, and the abutting contact between the leg 1566 and upper surface 1376 and the abutting contact between the leg 1598 and the lower surface 1404 further aid in transferring torsional loading from the distal hub 1022 to the distal end 1164 of the intermediate beam 1024 and vice versa in an opposite torsional direction.

The tension members 1050-1056 can be made of any suitable tensile load bearing member, including for example a threaded rod, a steel cable, a plastic cable, among others. In the present embodiment, the intermediate beam 1024 is an extruded member and the proximal hub 1020 and distal hub 1022 are cast members. It will be appreciated, of course, that other manufacturing processes may be used such as pultrusion and additive manufacturing techniques.

Referring now to FIG. 57, there is shown a flowchart 1700 of a method of assembling a support arm of a medical device support system, such as a support arm 110 for an extension arm 16 or load balancing arm 18 in the medical device support system 10 of FIG. 1. At step 1710, a proximal hub 720 is provided that has at least one elongated tension member 750 fixed to the proximal hub 720 with a free end 762 extending away from the proximal hub 720. At step 1720, an intermediate beam 724 is provided that has a cavity 736. At step 1730, the free end 762 of the at least one elongated tension member 750 is inserted into and through the cavity 736 of the intermediate beam 724. At step 1740, the free end 762 is inserted into a distal hub 722 so that the intermediate beam 724 is between the proximal hub 720 and the distal hub 722. As step 1750, the free end 762 is tightened to the distal hub 722 so that the at least one tension member 750 is in a state of tension and the intermediate beam 724 is in a state of compression.

The free end 762 of the at least one tension member 750 may be a threaded end and the tightening may include tightening a threaded nut 900 onto the threaded end 762. The inserting may include inserting the free end 762 into a clearance hole 840 inside the distal hub 722.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A support arm for a medical device support system, comprising:

a proximal hub and a distal hub;

an intermediate beam between the proximal hub and the distal hub, the intermediate beam having inward facing walls defining a cavity and including parallel ribs that project into the cavity defined by the inward facing walls; and, at least one tension member extending through the cavity of the intermediate beam, the at least one tension member being secured at opposite ends to the proximal hub and the distal hub against relative pivotal movement between the intermediate beam and the proximal hub and against relative pivotal movement between the intermediate beam and the distal hub, wherein the at least one tension member is secured at opposite ends to the proximal hub and the distal hub to prevent axial movement of the at least one tension member relative to the proximal hub and the distal hub, the at least one tension member securing the proximal hub, the distal hub, and the intermediate beam together, wherein the proximal hub includes a noncircular tubular end wall and the intermediate beam includes a noncircular tubular end wall, and the noncircular tubular end wall of the proximal hub is configured to mate with the noncircular tubular end wall of the intermediate beam at a mating interface without fasteners between the noncircular tubular end wall of the proximal hub and the noncircular tubular end wall of the intermediate beam such that torsional loading is transferred from the noncircular tubular end wall of the proximal hub to the noncircular tubular end wall of the intermediate beam and vice versa.

2. The support arm of claim 1, wherein the at least one tension member is in a state of tension and the intermediate beam is in a state of compression.

3. The support arm of claim 1, wherein the at least one tension member does not contact or engage the intermediate beam.

4. The support arm of claim 1, wherein the at least one tension member comprises four tension members.

5. The support arm of claim 1, wherein the at least one tension member comprises at least two tension members that have different lengths.

6. The support arm of claim 1, wherein the proximal hub includes at least one threaded hole and the at least one tension member is a threaded tension member that threads into the at least one threaded hole.

7. The support arm of claim 1, wherein the distal hub includes at least one clearance hole and the least one tension member passes through the at least one clearance hole such that an end of the at least one tension member is exposed.

8. The support arm of claim 7, wherein the at least one tension member is a threaded tension member, and further comprising a retainer that threads onto the exposed end and abuts a flat of the distal hub.

9. The support arm of claim 1, wherein the at least one tension member is selected from the group consisting of a threaded rod, a steel cable, and a plastic cable.

10. The support arm of claim 1, wherein the noncircular tubular end wall of the proximal hub corresponds in shape to the noncircular tubular end wall of the intermediate beam, wherein the noncircular tubular end wall of the proximal hub is configured to fit into the corresponding shape noncircular tubular end wall of the intermediate beam such that the noncircular tubular end wall of the proximal hub overlaps with the corresponding shape noncircular tubular end wall of the intermediate beam.

11. The support arm of claim 10, wherein the noncircular tubular end wall of the proximal hub has a shoulder and the shape corresponding noncircular tubular end wall of the intermediate beam has a stop face that abuts the shoulder.

12. The support arm of claim 1, wherein the proximal hub includes an end wall with a shoulder and the intermediate beam includes an end wall with a stop face that abuts the shoulder.

13. The support arm of claim 1, wherein the intermediate beam has a noncircular tubular shape in axial cross section.

14. The support arm of claim 1, wherein the proximal hub includes upper and lower plugs that fit into respective upper and lower receptacles of the intermediate beam.

15. The support arm of claim 1, wherein the intermediate beam is an extruded member.

16. A method of assembling a support arm of a medical device support system, comprising:

providing a proximal hub having at least one elongated tension member fixed to the proximal hub with a free end extending away from the proximal hub;

providing an intermediate beam having inward facing walls defining a cavity and including parallel ribs that project into the cavity defined by the inward facing walls;

inserting the free end of the at least one elongated tension member into and through the cavity of the intermediate beam;

inserting the free end into a distal hub so that the intermediate beam is between the proximal hub and the distal hub; and, tightening the free end to the distal hub so that the at least one tension member is in a state of tension and the intermediate beam is in a state of compression and such that the at least one tension member is secured at opposite ends to the proximal hub and the distal hub against relative pivotal movement between the intermediate beam and the proximal hub and against relative pivotal movement between the intermediate beam and the distal hub, and further such that the at least one tension member is secured at opposite ends to the proximal hub and the distal hub to prevent axial movement of the at least one tension member relative to the proximal hub and the distal hub, the at least one tension member securing the proximal hub, the distal hub, and the intermediate beam together, wherein the proximal hub includes a noncircular tubular end wall and the intermediate beam includes a noncircular tubular end wall, and the noncircular tubular end wall of the proximal hub is configured to mate with the noncircular tubular end wall of the intermediate beam at a mating interface without fasteners between the noncircular tubular end wall of the proximal hub and the noncircular tubular end wall of the intermediate beam such that torsional loading is transferred from the noncircular tubular end wall of the proximal hub to the noncircular tubular end wall of the intermediate beam and vice versa.

17. The method of claim 16, wherein the free end of the at least one tension member is a threaded end and the tightening includes tightening a threaded nut onto the threaded end.

18. The method of claim 16, wherein the inserting the free end into the distal hub includes inserting the free end into a clearance hole inside the distal hub.

19. A support arm for a medical device support system, comprising:

a proximal hub and a distal hub;

an intermediate beam between the proximal hub and the distal hub, the intermediate beam having inward facing walls defining a cavity and including parallel ribs that project into the cavity defined by the inward facing walls; and, at least one tension member extending through the cavity of the intermediate beam, the at least one tension member being secured at opposite ends to the proximal hub and the distal hub against relative pivotal movement between the intermediate beam and the proximal hub and against relative pivotal movement between the intermediate beam and the distal hub, wherein the at least one tension member is secured at opposite ends to the proximal hub and the distal hub to prevent axial movement of the at least one tension member relative to the proximal hub and the distal hub, the at least one tension member securing the proximal hub, the distal hub, and the intermediate beam together, wherein the proximal hub includes a noncircular tubular end wall and the intermediate beam includes a noncircular tubular end wall, and the noncircular tubular end wall of the proximal hub is configured to mate with the noncircular tubular end wall of the intermediate beam such that torsional loading is transferred from the noncircular tubular end wall of the proximal hub to the noncircular tubular end wall of the intermediate beam and vice versa, and wherein the noncircular tubular end wall of the proximal hub and the noncircular tubular end wall of the intermediate beam each include a first arced portion having a first radius and a second arced portion having a second radius, wherein the first radius is different from second radius.

20. The support arm of claim 19, wherein the noncircular tubular end wall of the proximal hub and the noncircular tubular end wall of the intermediate beam each further include a third arced portion having a third radius that is different from the first radius and the second radius.

* * * * *